US012735410B2

(12) United States Patent
Gan et al.

(10) Patent No.: US 12,735,410 B2
(45) Date of Patent: Sep. 15, 2026

(54) N-PHENYLIMINE DERIVATIVE AND PREPARATION METHOD AND USE THEREOF

(71) Applicant: Guizhou University, Guiyang (CN)

(72) Inventors: Xiuhai Gan, Guiyang (CN); Wang Geng, Guiyang (CN); Gangyin Tai, Guiyang (CN); Qi Zhang, Guiyang (CN); Wei Zhang, Guiyang (CN); Chao Chen, Guiyang (CN); Mengfan Jiang, Guiyang (CN)

(73) Assignee: Guizhou University, Guiyang (CN)

( * ) Notice: Subject to any disclaimer, the term of this patent is extended or adjusted under 35 U.S.C. 154(b) by 383 days.

(21) Appl. No.: 18/221,881

(22) Filed: Jul. 14, 2023

(65) Prior Publication Data

US 2024/0300932 A1 Sep. 12, 2024

(30) Foreign Application Priority Data

Feb. 23, 2023 (CN) ......................... 202310152830.5
Jun. 6, 2023 (CN) ......................... 202310659084.9

(51) Int. Cl.

| | |
|---|---|
| ***C07D 413/14*** | (2006.01) |
| ***A01N 43/38*** | (2006.01) |
| ***A01N 43/82*** | (2006.01) |
| ***A01P 13/00*** | (2006.01) |
| ***C07D 209/48*** | (2006.01) |
| ***C07D 413/12*** | (2006.01) |

(52) U.S. Cl.
CPC ........... *C07D 413/12* (2013.01); *A01N 43/38* (2013.01); *A01N 43/82* (2013.01); *A01P 13/00* (2021.08); *C07D 209/48* (2013.01); *C07D 413/14* (2013.01)

(58) Field of Classification Search
CPC ................ C07D 413/12; C07D 209/48; C07D 413/14; A01N 43/38; A01N 43/82
See application file for complete search history.

(56) References Cited

U.S. PATENT DOCUMENTS 5,169,428 A * 12/1992 Tsuzuki ................. A01N 43/08 504/179

FOREIGN PATENT DOCUMENTS

CN 115093377 A 9/2022
EP 0323271 A1 7/1989

OTHER PUBLICATIONS

Silverman (The Organic Chemistry of Drug Design and Drug Action, Second Edition, Chapter 2, p. 7-120, 2004) (Year: 2004).*
Huang Ming-Zhi et al; "Synthesis and crystal structure of 3-chloro-N-(2-chloro-5-(1,3-dioxo-4,5,6,7-tetrahydro-1H isoindol-2(3H)-yl)-4-fluorophenyl)-2,2-dimethylpropanamide", Journal of Chemical Crystallography, vol. 35, No. 6, published in Jun. 2005, pp. 4.
Zhang, Haoa et al; "Synthesis and Herbicidal Activity of N-(4-Chloro-2-fluoro-5-substituted phenyl)isoindole-1,3-dione Derivatives", available at; http://sioc-journal.cn/, published in 2015, pp. 8. (Only Abstract Submitted).
First Office Action in the Chinese Application No. 202310659084.9 mailed on May 29, 2025, pp. 15.

* cited by examiner

*Primary Examiner* — Bethany P Barham
*Assistant Examiner* — Danielle Johnson
(74) *Attorney, Agent, or Firm* — Gearhart Law LLC

(57) ABSTRACT

Provided are an N-phenylimine derivative and a preparation method and use thereof. Provided is an N-phenylimine derivative, being selected from the group consisting of: a 1,2,4-oxadiazole-N-phenylimine derivative represented by formula 1, a 1,3,4-oxadiazole-N-phenylimine derivative represented by formula 2, an N-phenylimine amide (ester) derivative represented by formula 3, and an N-phenylimine benzoate derivative represented by formula 4.

formula 1

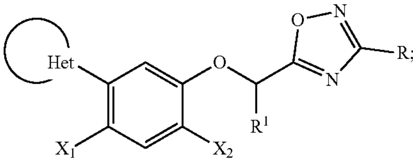

formula 2

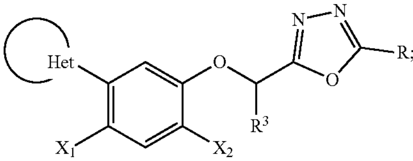

formula 3

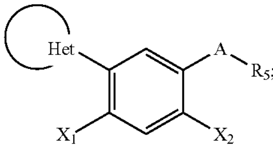

formula 4

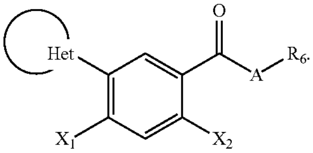

3 Claims, No Drawings

N-PHENYLIMINE DERIVATIVE AND PREPARATION METHOD AND USE THEREOF

CROSS REFERENCE TO RELATED APPLICATION

This patent application claims the benefits and priorities of Chinese Patent Application No. 2023101528305 filed with the China National Intellectual Property Administration on Feb. 23, 2023, and Chinese Patent Application No. 2023106590849 filed with the China National Intellectual Property Administration on Jun. 6, 2023, the disclosures of which are incorporated by reference herein in its entirety as part of the present application.

TECHNICAL FIELD

The present disclosure belongs to the technical field of chemical industry and pesticides, and specifically relates to an N-phenylimine derivative and a preparation method and use thereof.

BACKGROUND

Since the mid-20th century, synthetic organic herbicides have played an important role in weed control. However, the overuse of some herbicides has led to significant development of weed resistance and huge negative environmental impacts.

Protoporphyrinogen oxidase (PPO), one of the most important target enzymes, is the penultimate enzyme in the biosynthesis of chlorophyll and heme. The PPO belongs to a large family of enzymes containing flavin adenine dinucleotide (FAD). PPO could catalyze the conversion of protoporphyrinogen IX to protoporphyrin IX. On one hand, PPO inhibitors could inhibit PPO in plants. Inhibition of the PPO leads to toxic accumulation of protoporphyrin IX in plant cytoplasm. Under light illumination, the protoporphyrin IX reacts with oxygen to generate a large amount of reactive oxygen species (ROS), which damage cell membranes to cause rapid burn symptoms in plants. On the other hand, the PPO inhibitors have many advantages such as broad herbicidal spectrum, strong drug resistance, environmental friendliness, and low toxicity and usage rate.

N-phenylimine inhibitors are more easily absorbed by leaves and transferred throughout the plant due to hydrophobic groups on a structure of N-phenylimine. Moreover, the N-phenylimine inhibitors have an improved binding affinity with plant PPOs, thus showing a wider application space.

However, N-phenylimine inhibitors currently have a poor inhibitory effect on broad-leaf weeds, and cannot effectively inhibit the broad-leaf weeds.

SUMMARY

An object of the present disclosure is to provide an N-phenylimine derivative and a preparation method and use thereof. The N-phenylimine derivative has a relatively high inhibitory effect on broad-leaf weeds (including *Abutilon theophrasti, Amaranthus retroflexus*, and *Portulaca oleracea*) at a dosage of 10 a.i.g/mu (i.e. 10 available ingredient gram/666.7 $m^2$), and shows broad application prospects.

The present disclosure provides an N-phenylimine derivative, where the N-phenylimine derivative is selected from the group consisting of: a 1,2,4-oxadiazole-N-phenylimine derivative represented by formula 1, a 1,3,4-oxadiazole-N-phenylimine derivative represented by formula 2, an N-phenylimine amide (ester) derivative represented by formula 3, and an N-phenylimine benzoate derivative represented by formula 4. In the present disclosure, structures of oxadiazoles, amides, esters, and phenoxyethyls are introduced into N-phenylimine compounds. Using different phthalimide derivatives as a core skeleton, structural active units of the oxadiazoles, amides, esters, and phenoxyethyls are introduced based on the principle of active substructure splicing. In this way, a series of N-phenylphthalimide derivatives represented by formula 1, formula 2, formula 3, or formula 4 are synthesized. Based on the structure of phthalimides, with different substituted "imines" as pharmacophores, N-phenylimine herbicides with a simple structure and an excellent herbicidal activity have been created. At a dosage of 10 a.i.g/mu, the N-phenylimine derivative has a post-emergence inhibition rate of 28% to 50% on *Echinochloa crusgalli*, a post-emergence inhibition rate of 34% to 56% on *Digitaria sanguinalis*, a post-emergence inhibition rate of 50% to 70% on *Setaria viridis*, a post-emergence inhibition rate of 100% on *Abutilon theophrasti*, a post-emergence inhibition rate of 100% on *Portulaca oleracea*, and a post-emergence inhibition rate of 100% on *Amaranthus retroflexus*. In contrast, a control drug, flumioxazin, at 10 a.i.g/mu, has a post-emergence inhibition rate of 40% to 90% against gramineous weeds, and a control effect of 100% against broad-leaf weeds. Moreover, some compounds have a control effect of 100% on *Abutilon theophrasti, Amaranthus retroflexus*, and *Portulaca oleracea* at 2.5 a.i.g/mu, showing that the N-phenylimine derivative provided by the present disclosure has an excellent control effect on the broad-leaf weeds. Therefore, the present disclosure provides a feasible basis for the creation of high-efficiency, broad-spectrum, green, and low-toxicity herbicides and provides a potential lead structure for the development of new PPO inhibitors.

The present disclosure further provides a preparation method of the N-phenylimine derivative. The preparation method has simple steps, low production cost, and wide application prospects.

DETAILED DESCRIPTION OF THE EMBODIMENTS

The present disclosure provides an N-phenylimine derivative, where the N-phenylimine derivative is selected from the group consisting of: a 1,2,4-oxadiazole-N-phenylimine derivative represented by formula 1, a 1,3,4-oxadiazole-N-phenylimine derivative represented by formula 2, an N-phenylimine amide (ester) derivative represented by formula 3, and an N-phenylimine benzoate derivative represented by formula 4;

formula 1

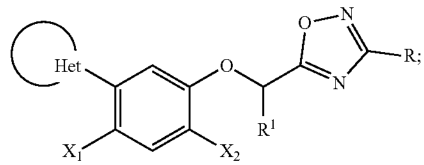

formula 2

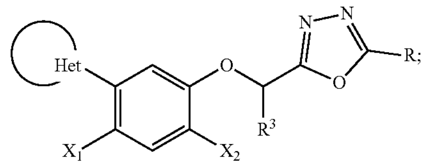

-continued
formula 3
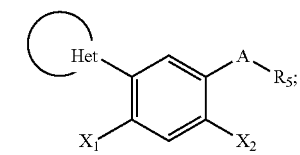
formula 4
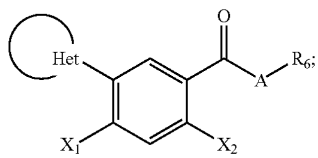
where in formula 1, formula 2, formula 3, and formula 4,
Het is selected from the group consisting of:
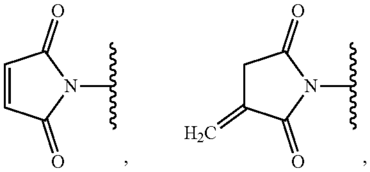
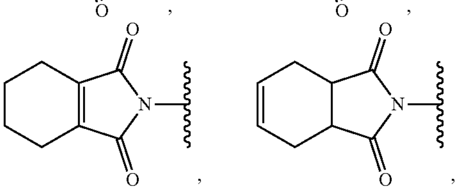
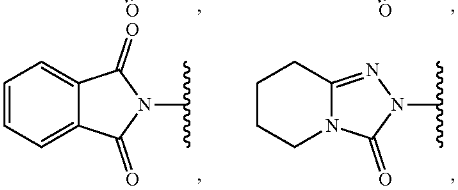
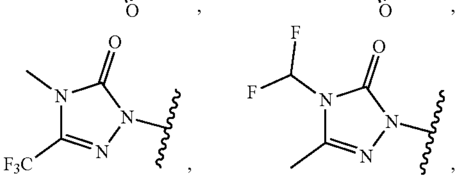
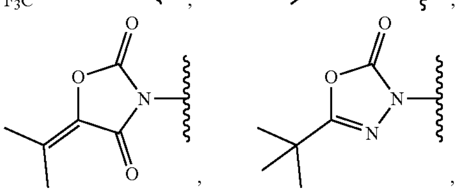
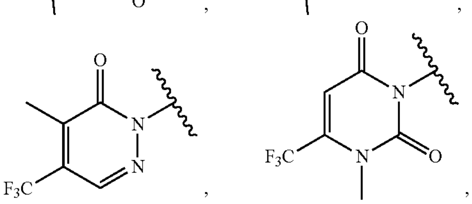
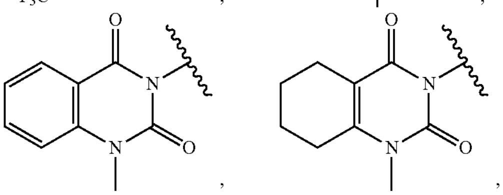
-continued
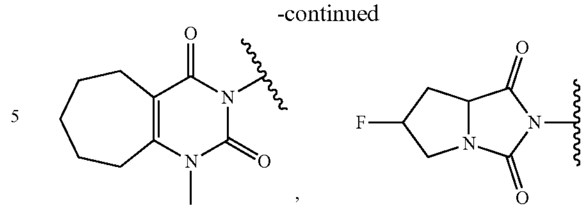
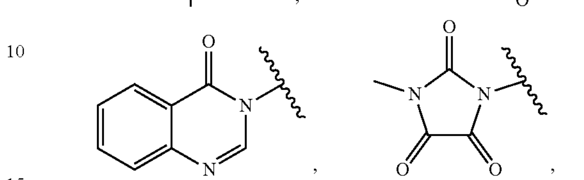
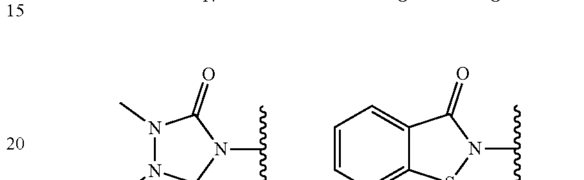
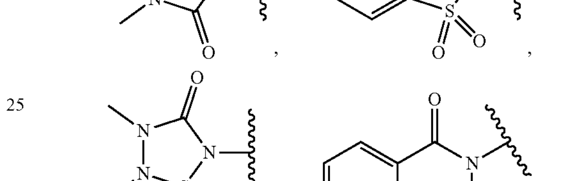
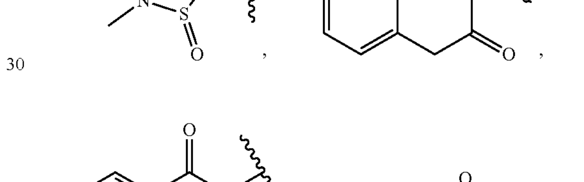
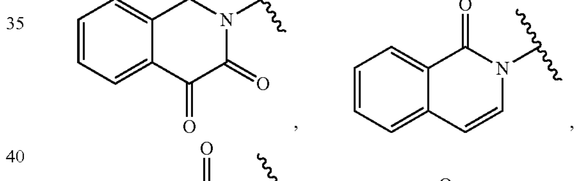
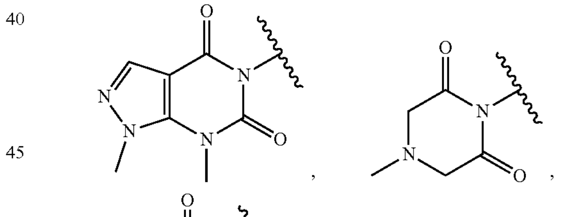
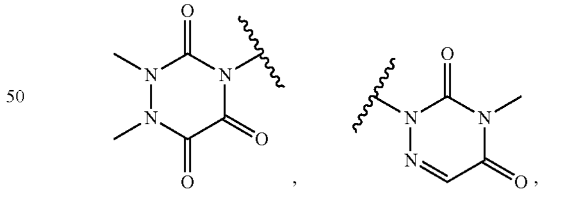
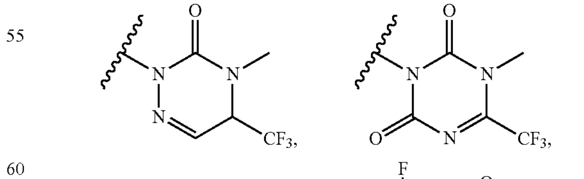
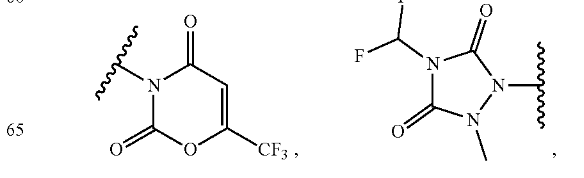
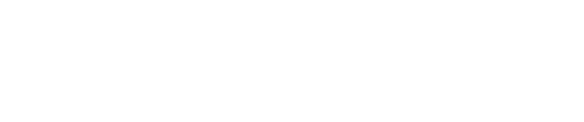

-continued

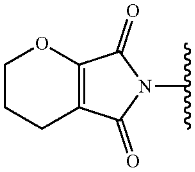,
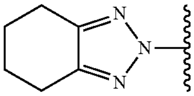,
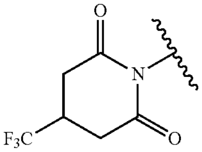,
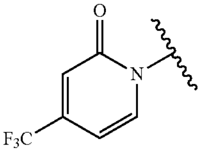,
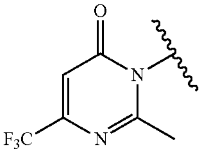,
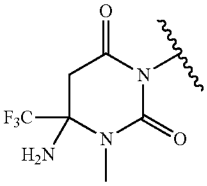,
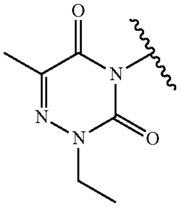,
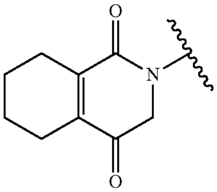,
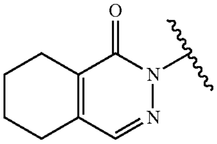,
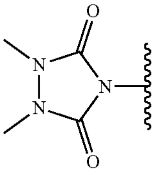,
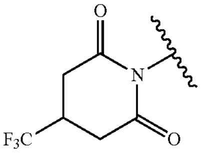,
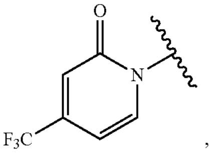,
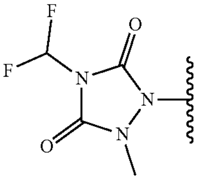,
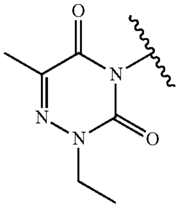,
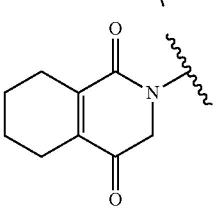,
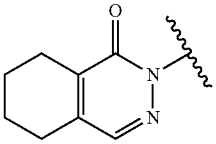,
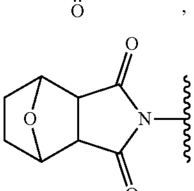,
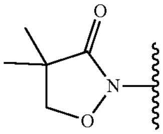, -continued

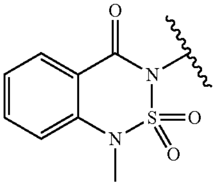,
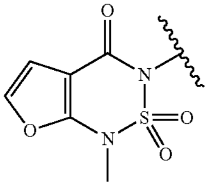,
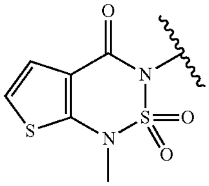,
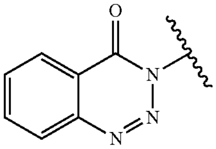,
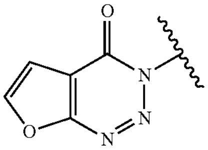,
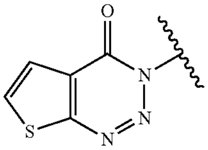,
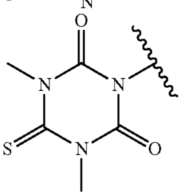,
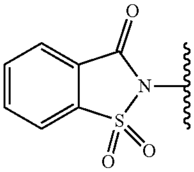,
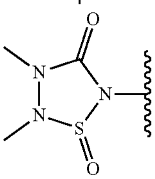,
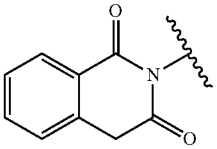,
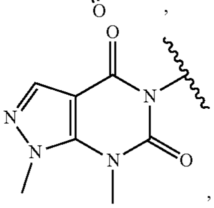,
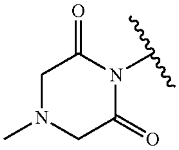,
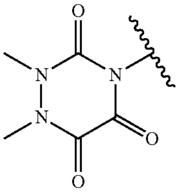, and
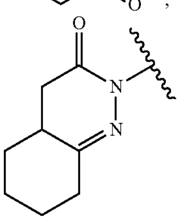;

in formula 1, formula 2, formula 3, and formula 4, each of $X_1$ and $X_2$ is independently selected from the group consisting of F, Cl, H, Br, —CN, methyl, carboxyl, an aldehyde group, hydroxyl, an ester group, and amido;

in formula 1, $R^1$ is selected from the group consisting of H and $—CH_3$; and in formula 1, R is selected from the group consisting of a substituted aliphatic group, substituted or unsubstituted phenyl, substituted pyridyl, substituted or unsubstituted furyl, substituted or unsubstituted thienyl, and an ester group;

in formula 2, $R^3$ is selected from the group consisting of H and $—CH_3$; and in formula 2, R is selected from the group consisting of a substituted aliphatic group, substituted phenyl, substituted pyridyl, substituted or unsubstituted furyl, substituted or unsubstituted thienyl, and an ester group;

in formula 3 and formula 4, A is independently selected from the group consisting of —NH—, —O—, and —S—;

in formula 3, $R^5$ is selected from the group consisting of an ester group, substituted phenoxyethyl, substituted amino, and substituted alkyl; and in formula 4, $R^6$ is selected from the group consisting of an ester group, substituted phenoxyethyl, and substituted amino.

In some embodiments, in formula 1, formula 2, formula 3, and formula 4, Het is selected from the group consisting of:

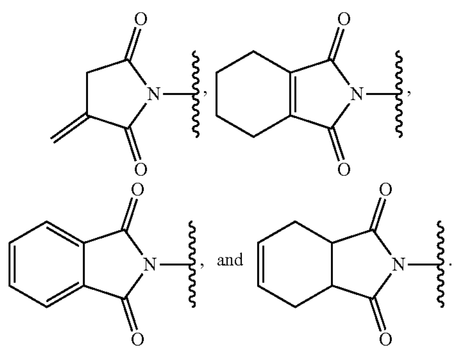

In some embodiments, in formula 1, formula 2, formula 3, and formula 4, each of $X_1$ and $X_2$ is independently selected from the group consisting of F and Cl. In some embodiments, $X_1$ is F, and $X_2$ is Cl.

In some embodiments, in formula 1, $R^1$ is H. In some embodiments, in formula 1, R is selected from the group consisting of

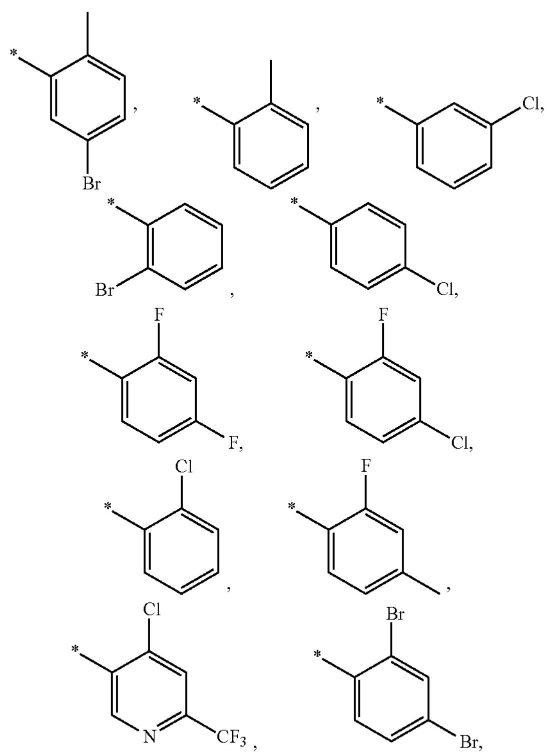

-continued

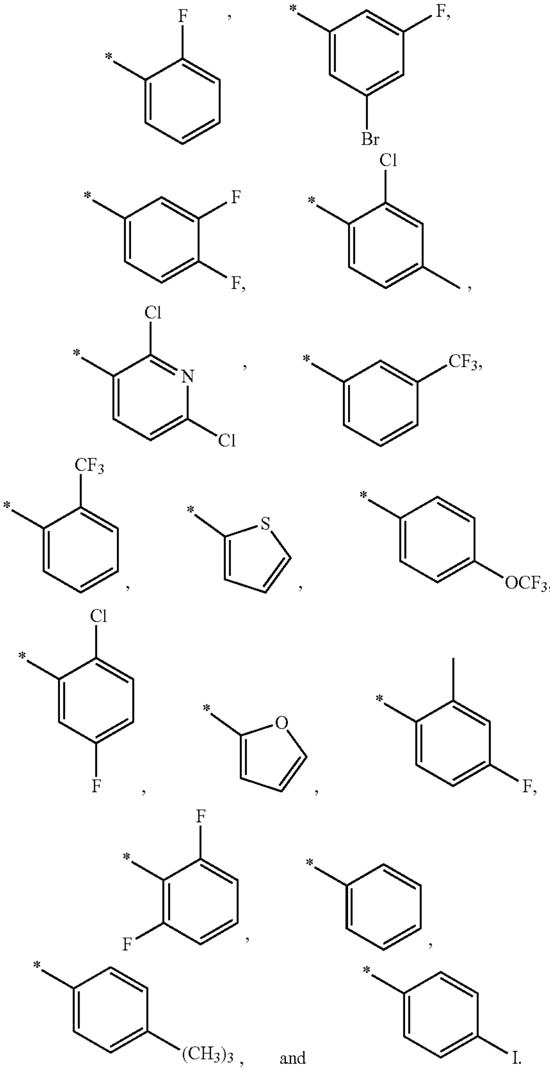

In some embodiments, in formula 2, $R^3$ is H; and in formula 2, R is selected from the group consisting of

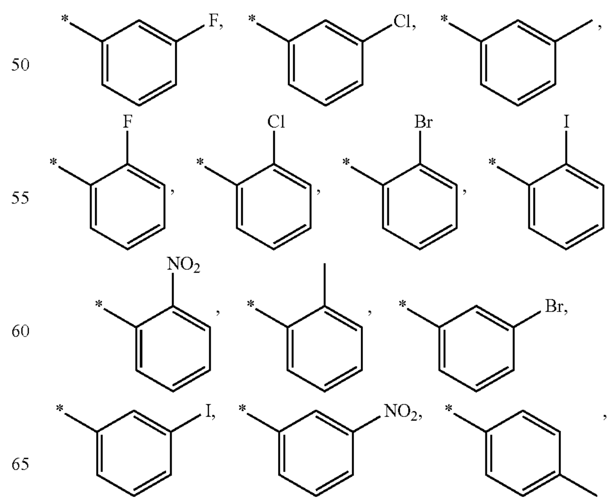

-continued

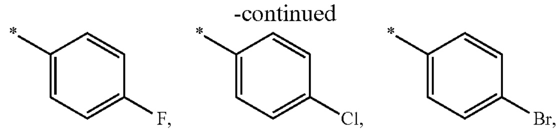

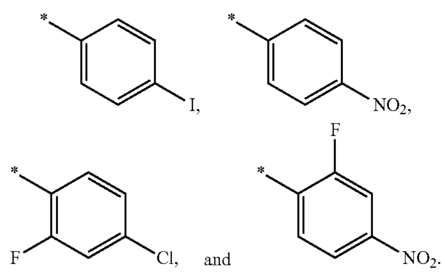

and

In some embodiments, in formula 3, A is selected from the group consisting of —NH— and O.

In some embodiments, in formula 3, $R^5$ is selected from the group consisting of

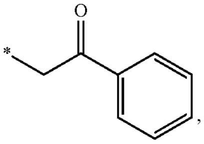

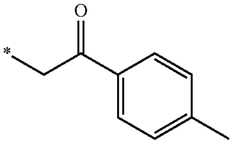

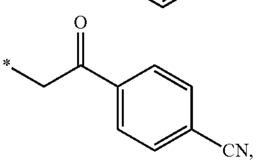

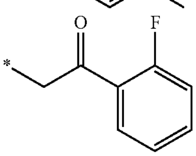

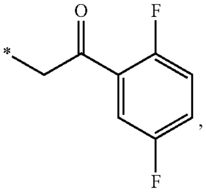

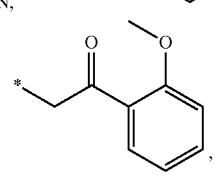

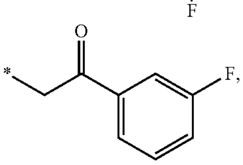

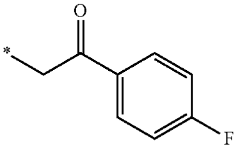

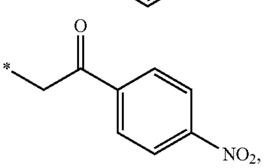

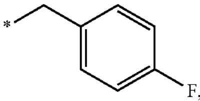

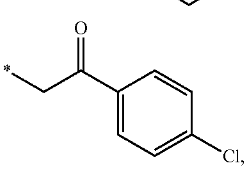

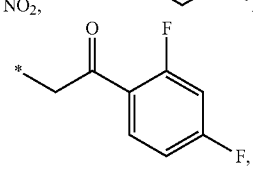

and

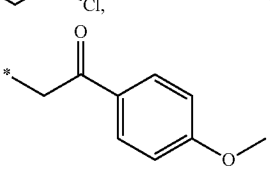

In some embodiments, in formula 4, A is O.

In some embodiments, in formula 4, $R^6$ is selected from the group consisting of

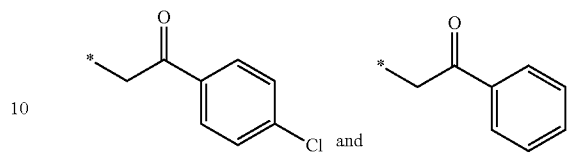

and

In some embodiments, the N-phenylimine derivative is any one selected from the group consisting compounds represented by formula 1-1 to formula 1-27, formula 2-1 to formula 2-20, formula 3-1 to formula 3-25, and formula 4-1 to formula 4-2, respectively:

formula 1-1 (A1)

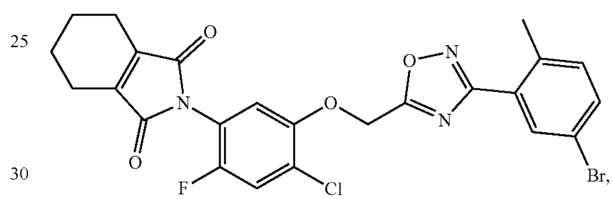

formula 1-2 (A2)

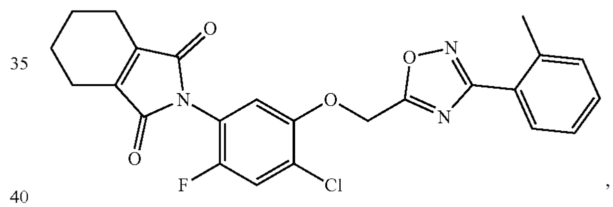

formula 1-3 (A3)

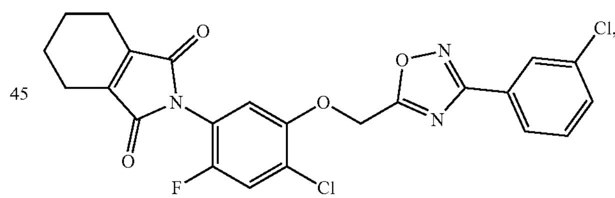

formula 1-4 (A4)

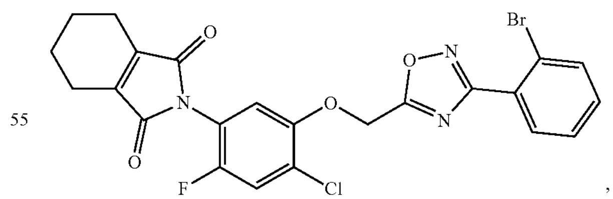

formula 1-5 (A5)

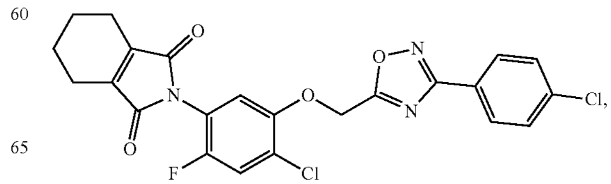

-continued
formula 1-6 (A6)
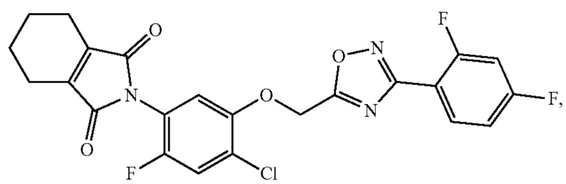
formula 1-7 (A7)
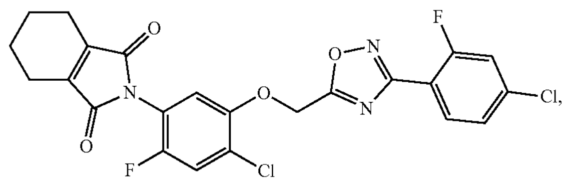
formula 1-8 (A8)
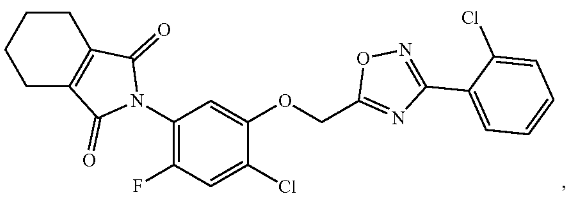
,
formula 1-9 (A9)
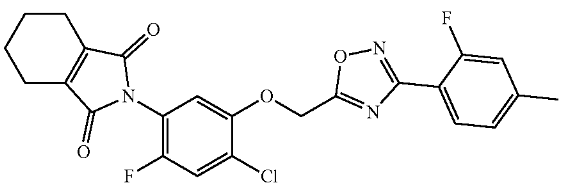
,
formula 1-10 (A10)
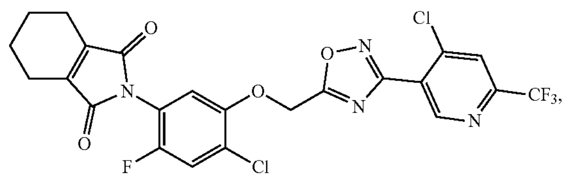
formula 1-11 (A11)
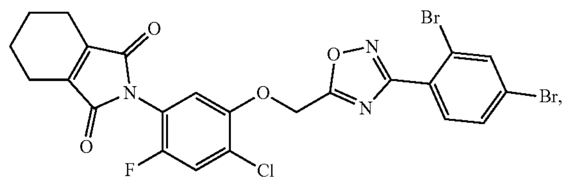
formula 1-12 (A12)
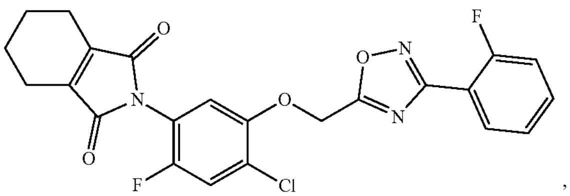
,
-continued
formula 1-13 (A13)
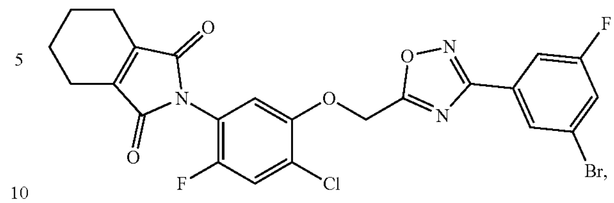
formula 1-14 (A14)
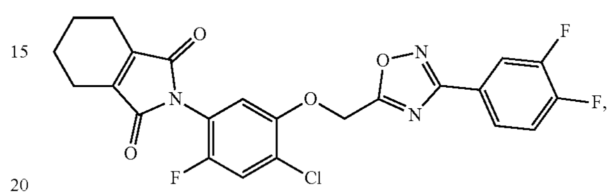
formula 1-15 (A15)
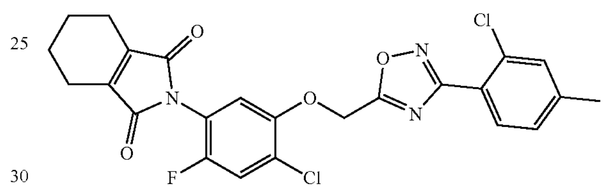
,
formula 1-16 (A16)
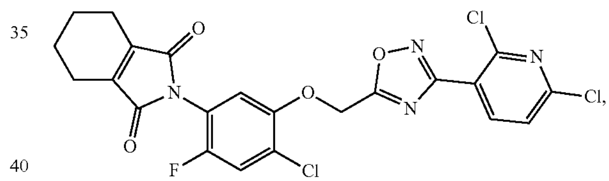
formula 1-17 (A17)
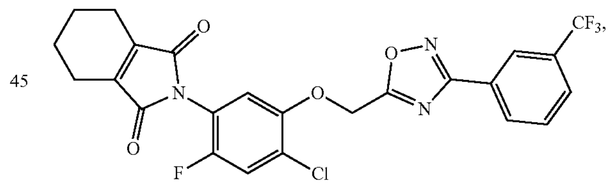
formula 1-18 (A18)
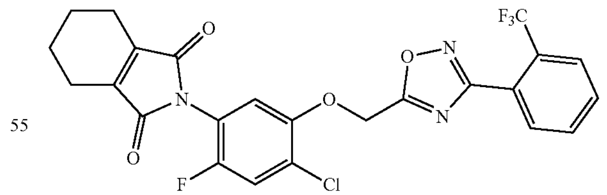
,
formula 1-19 (A19)
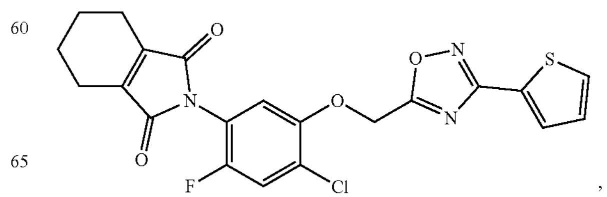
, -continued
formula 1-20 (A20)
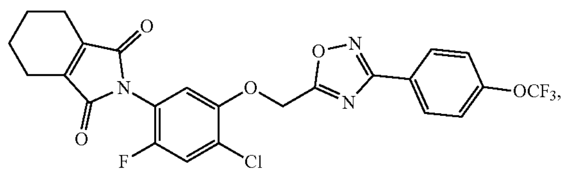
formula 1-21 (A21)
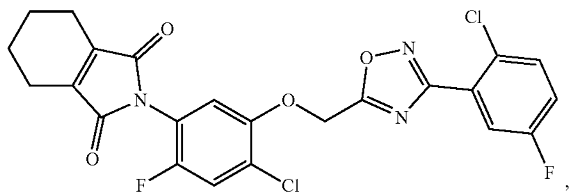
formula 1-22 (A22)
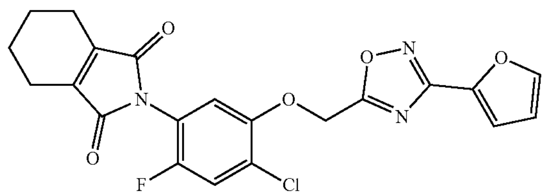
formula 1-23 (A23)
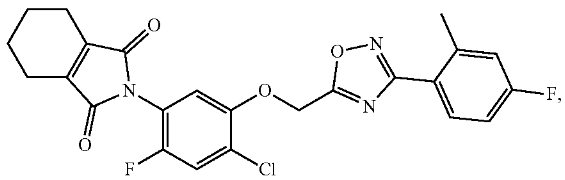
formula 1-24 (A24)
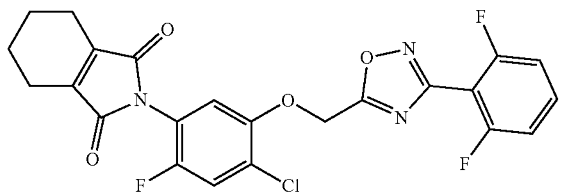
formula 1-25 (A25)
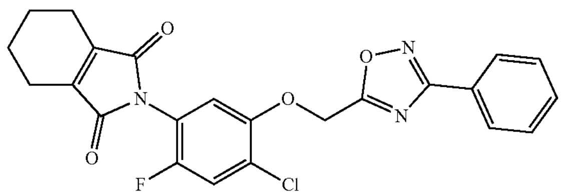
formula 1-26 (A26)
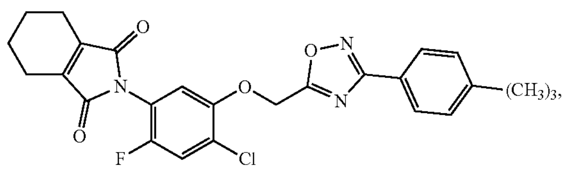
-continued
formula 1-27 (A27)
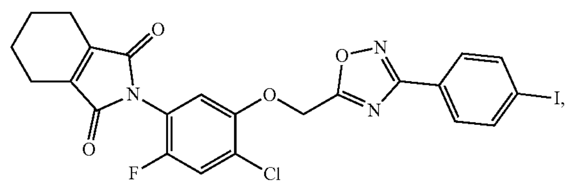
formula 2-1 (B1)
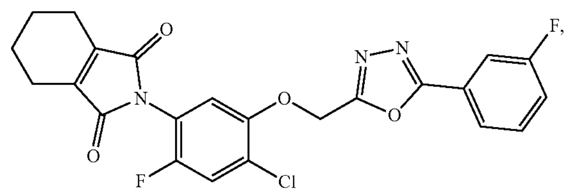
formula 2-2 (B2)
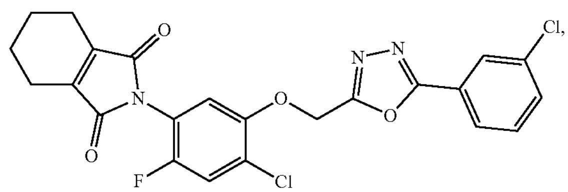
formula 2-3 (B3)
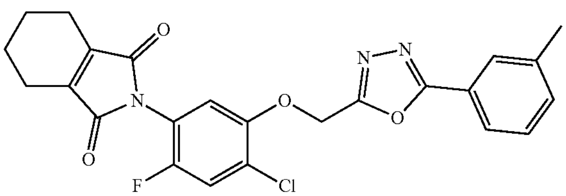
formula 2-4 (B4)
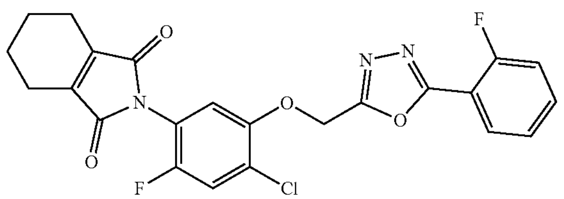
formula 2-5 (B5)
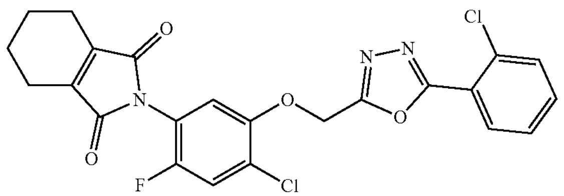
formula 2-6 (B6)
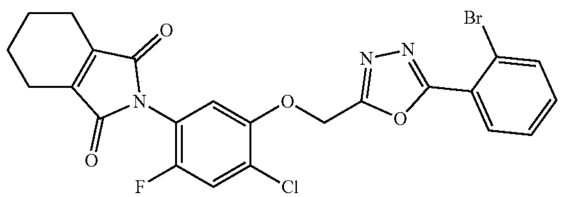

-continued
formula 2-7 (B7)
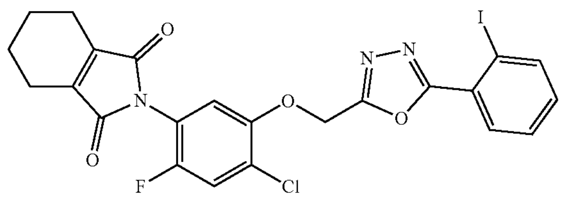
,
formula 2-8 (B8)
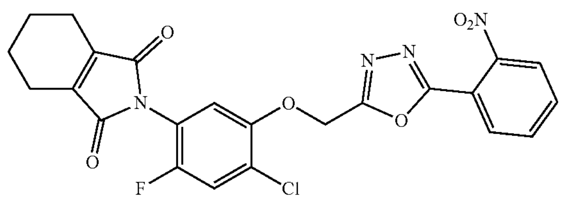
,
formula 2-9 (B9)
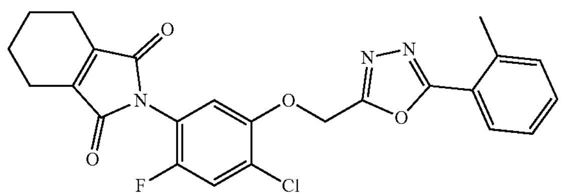
,
formula 2-10 (B10)
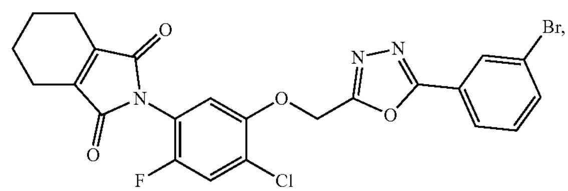
formula 2-11 (B11)
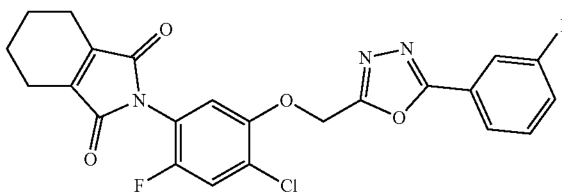
formula 2-12 (B12)
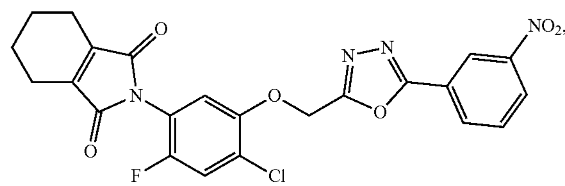
formula 2-13 (B13)
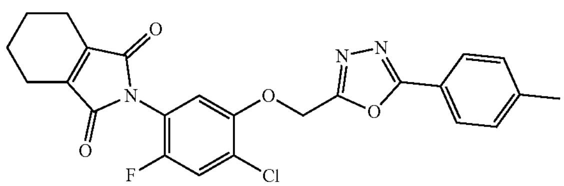
,
-continued
formula 2-14 (B14)
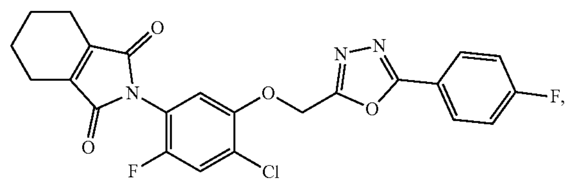
formula 2-15 (B15)
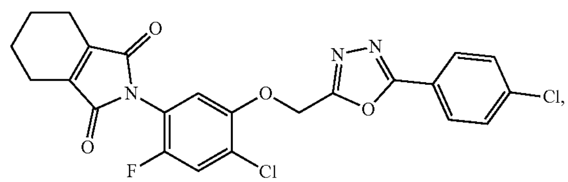
formula 2-16 (B16)
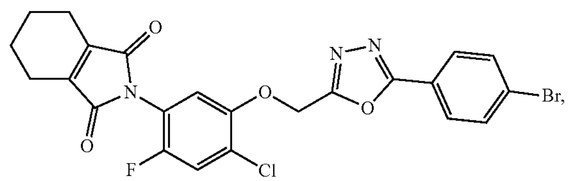
formula 2-17 (B17)
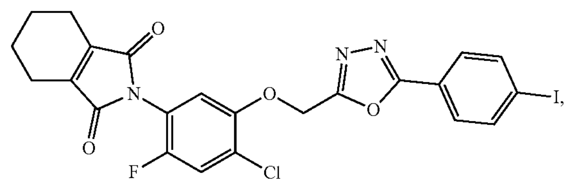
formula 2-18 (B18)
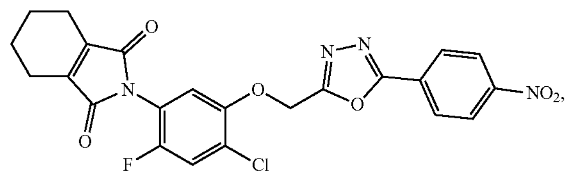
formula 2-19 (B19)
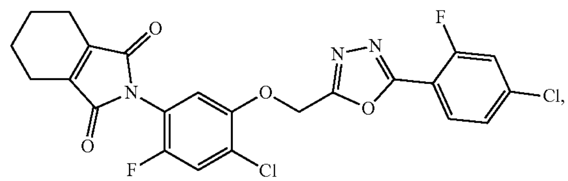
formula 2-20 (B20)
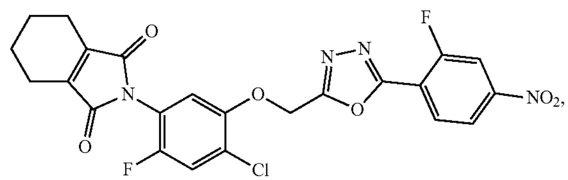

-continued
formula 3-1 (C1)
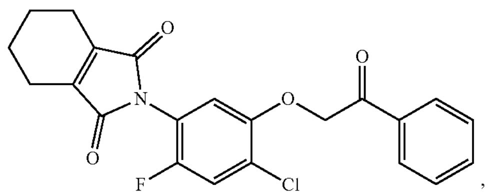
,
formula 3-2 (C2)
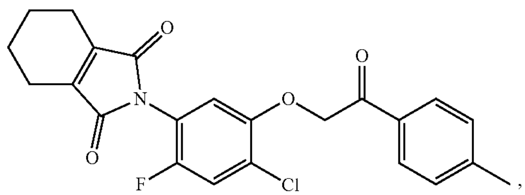
,
formula 3-3 (C3)
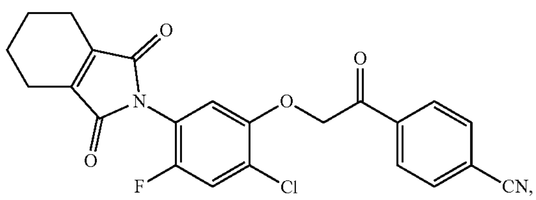
formula 3-4 (C4)
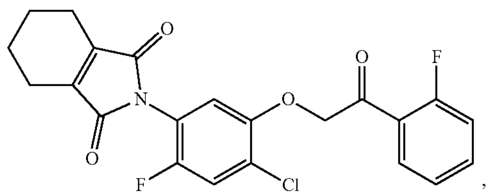
,
formula 3-5 (C5)
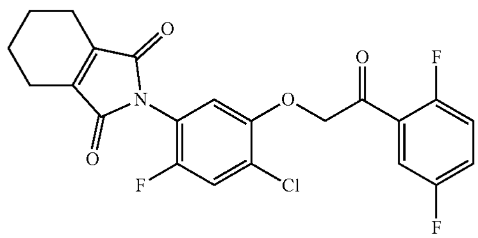
formula 3-6 (C6)
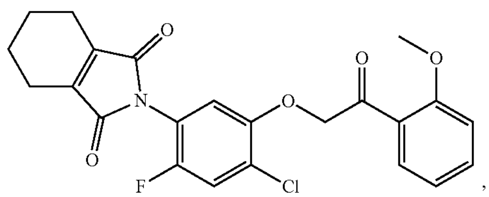
,
formula 3-7 (C7)
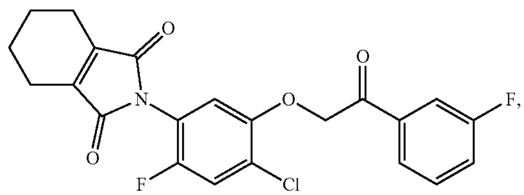
-continued
formula 3-8 (C8)
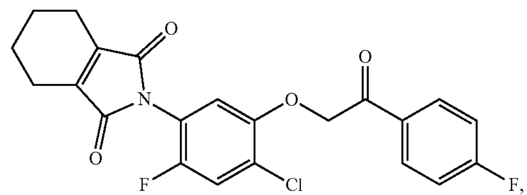
formula 3-9 (C9)
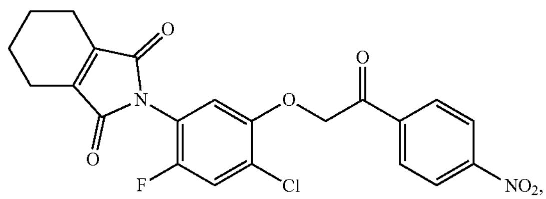
formula 3-10 (C10)
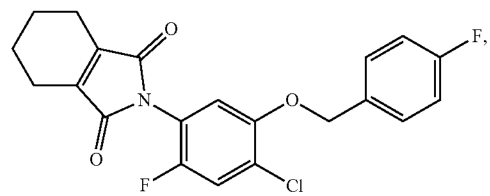
formula 3-11 (C11)
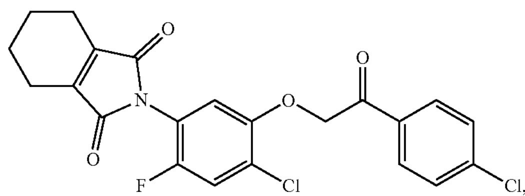
formula 3-12 (C12)
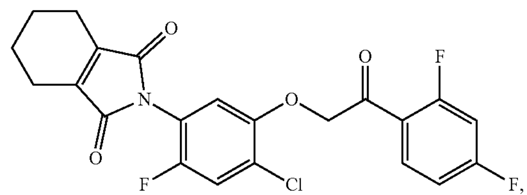
formula 3-13 (C13)
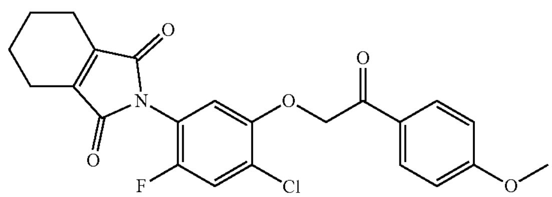
,
formula 3-14 (C14)
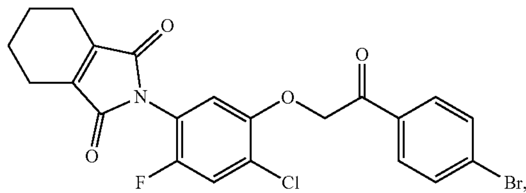

-continued
formula 3-15 (C15)
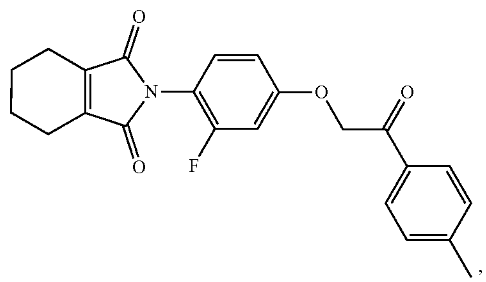
formula 3-16 (D1)
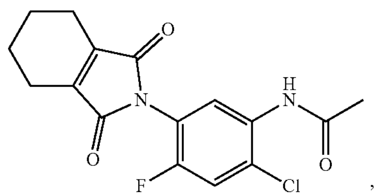
formula 3-17 (D2)
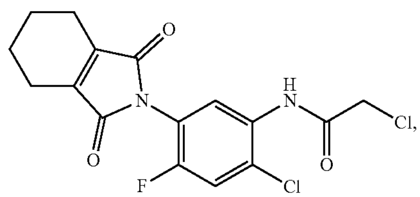
formula 3-18 (D3)
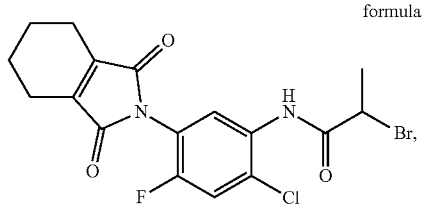
formula 3-19 (D4)
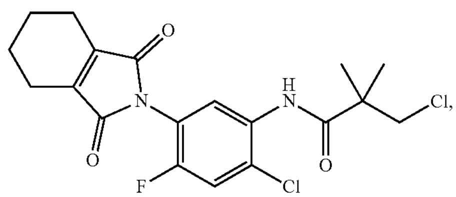
formula 3-20 (D5)
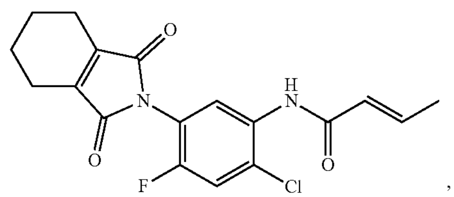
formula 3-21 (D6)
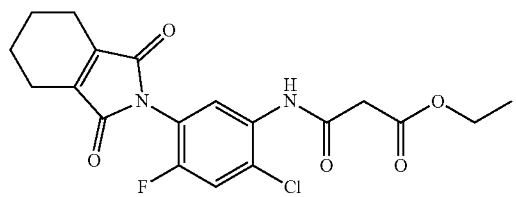
-continued
formula 3-22 (D7)
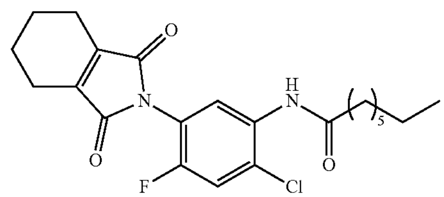
formula 3-23 (D8)
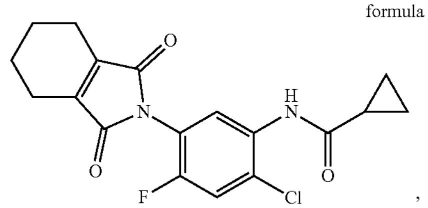
formula 3-24 (D9)
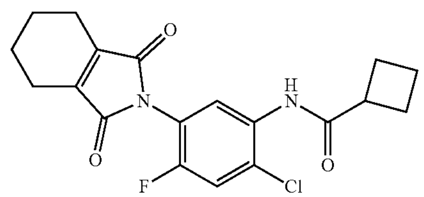
formula 3-25 (D10)
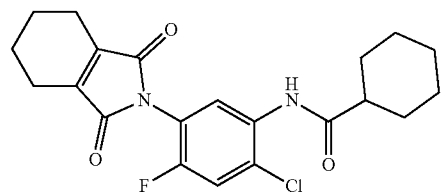
formula 4-1 (E1)
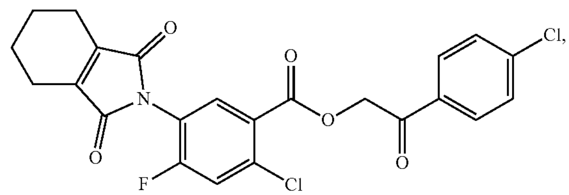
formula 4-2 (E2)
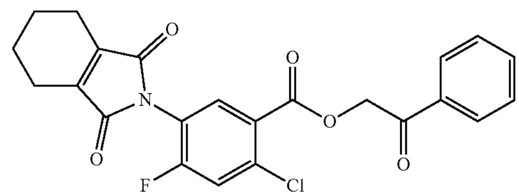
In the present disclosure, the chemical names of the compounds represented by formula 1-1 to formula 1-40, formula 2-1 to formula 2-20, formula 3-1 to formula 3-35, and formula 4-1 to formula 4-2 are specifically as follows:

Compound A1

2-(5-((3-(5-bromo-2-tolyl)-1,2,4-oxadiazole-5-yl) methoxy)-4-chloro-2-fluorophenyl)-4,5,6,7-tetrahydro-1H-isoindole-1,3(2H)-dione Compound A2

2-(4-chloro-2-fluoro-5-((3-(2-tolyl)-1,2,4-oxadiazole-5-yl)methoxy)phenyl)-4,5,6,7-tetrahydro-1H-isoindole-1,3(2H)-dione Compound A3

2-(4-chloro-5-(3-(3-chlorophenyl)-1,2,4-oxadiazole-5-yl)methoxy)-2-fluorophenyl)-4,5,6,7-tetrahydro-1H-isoindole-1,3(2H)-dione Compound A4

2-(5-(3-(2-bromophenyl)-1,2,4-oxadiazole-5-yl) methoxy)-4-chloro-2-fluorophenyl)-4,5,6,7-tetrahydro-1H-isoindole-1,3(2H)-dione Compound A5

2-(4-chloro-5-(3-(4-chlorophenyl)-1,2,4-oxadiazole-5-yl)methoxy)-2-fluorophenyl)-4,5,6,7-tetrahydro-1H-isoindole-1,3(2H)-dione Compound A6

2-(4-chloro-5-(3-(2,4-difluorophenyl)-1,2,4-oxadiazole-5-yl)methoxy)-2-fluorophenyl)-4,5,6,7-tetrahydro-1H-isoindole-1,3(2H)-dione Compound A7

2-(4-chloro-5-(3-(4-chloro-2-fluorophenyl)-1,2,4-oxadiazole-5-yl)methoxy)-2-fluorophenyl)-4,5,6,7-tetrahydro-1H-isoindole-1,3(2H)-dione Compound A8

2-(4-chloro-5-(3-(2-chlorophenyl)-1,2,4-oxadiazole-5-yl)methoxy)-2-fluorophenyl)-4,5,6,7-tetrahydro-1H-isoindole-1,3(2H)-dione Compound A9

2-(4-chloro-2-fluoro-5-(3-(2-fluoro-4-methylphenyl)-1,2,4-oxadiazole-5-yl)methoxy)phenyl)-4,5,6,7-tetrahydro-1H-isoindole-1,3(2H)-dione Compound A10

2-(4-chloro-5-(3-(4-chloro-6-(trifluoromethyl)pyridin-3-ly)-1,2,4-oxadiazole-5-yl)methoxy)-2-fluorophenyl)-4,5,6,7-tetrahydro-1H-isoindole-1,3(2H)-dione Compound A11

2-(4-chloro-5-(3-(2,4-dibromophenyl)-1,2,4-oxadiazole-5-yl)methoxy)-2-fluorophenyl)-4,5,6,7-tetrahydro-1H-isoindole-1,3(2H)-dione Compound A12

2-(4-chloro-2-fluoro-5-(3-(2-fluorophenyl)-1,2,4-oxadiazole-5-yl)methoxy)phenyl)-4,5,6,7-tetrahydro-1H-isoindole-1,3(2H)-dione Compound A13

2-(3-(3-(3-(3-bromo-5-fluorophenyl)-1,2,4-oxadiazole-5-yl)methoxy)-4-chloro-2-fluorophenyl)-4,5,6,7-tetrahydro-1H-isoindole-1,3(2H)-dione Compound A14

2-(4-chloro-5-(3-(3,4-difluorophenyl)-1,2,4-oxadiazole-5-yl)methoxy)-2-fluorophenyl)-4,5,6,7-tetrahydro-1H-isoindole-1,3(2H)-dione Compound A15

2-(4-chloro-5-(3-(2-chloro-4-tolyl)-1,2,4-oxadiazole-5-yl)methoxy)-2-fluorophenyl)-4,5,6,7-tetrahydro-1H-isoindole-1,3(2H)-dione Compound A16

2-(4-chloro-5-(3-(2,6-dichloropyridin-3-yl)-1,2,4-oxadiazole-5-yl)methoxy)-2-fluorophenyl)-4,5,6,7-tetrahydro-1H-isoindole-1,3(2H)-dione Compound A17

2-(4-chloro-2-fluoro-5-(3-(3-(trifluoromethyl)phenyl)-1,2,4-oxadiazole-5-yl)methoxy)phenyl)-4,5,6,7-tetrahydro-1H-isoindole-1,3(2H)-dione Compound A18

2-(4-chloro-2-fluoro-5-(3-(2-(trifluoromethyl)phenyl)-1,2,4-oxadiazole-5-yl)methoxy)phenyl)-4,5,6,7-tetrahydro-1H-isoindole-1,3(2H)-dione Compound A19

2-(4-chloro-2-fluoro-5-(3-(thiophen-2-yl)-1,2,4-oxadiazole-5-yl)methoxy)phenyl)-4,5,6,7-tetrahydro-1H-isoindole-1,3(2H)-dione Compound A20

2-(4-chloro-2-fluoro-5-(3-(4-(trifluoromethoxy)phenyl)-1,2,4-oxadiazole-5-yl)methoxy)phenyl)-4,5,6,7-tetrahydro-1H-isoindole-1,3(2H)-dione Compound A21

2-(4-chloro-5-(3-(2-chloro-5-fluorophenyl)-1,2,4-oxadiazole-5-yl)methoxy)-2-fluorophenyl)-4,5,6,7-tetrahydro-1H-isoindole-1,3(2H)-dione Compound A22

2-(4-chloro-2-fluoro-5-(3-(furan-2-yl)-1,2,4-oxadiazole-5-yl)methoxy)phenyl)-4,5,6,7-tetrahydro-1H-isoindole-1,3(2H)-dione Compound A23

2-(4-chloro-2-fluoro-5-(3-(4-fluoro-2-methylphenyl)-1,2,4-oxadiazole-5-yl)methoxy)phenyl)-4,5,6,7-tetrahydro-1H-isoindole-1,3(2H)-dione Compound A24

2-(4-chloro-5-(3-(2,6-difluorophenyl)-1,2,4-oxadiazole-5-yl)methoxy)-2-fluorophenyl)-4,5,6,7-tetrahydro-1H-isoindole-1,3(2H)-dione Compound A25

2-(4-chloro-2-fluoro-5-(3-phenyl-1,2,4-oxadiazole-5-yl)methoxy)phenyl)-4,5,6,7-tetrahydro-1H-isoindole-1,3(2H)-dione Compound A26

2-(5-(3-(4-(tert-butyl)phenyl)-1,2,4-oxadiazole-5-yl)methoxy)-4-chloro-2-fluorophenyl)-4,5,6,7-tetrahydro-1H-isoindole-1,3(2H)-dione Compound A27

2-(4-chloro-2-fluoro-5-(3-(4-iodophenyl)-1,2,4-oxadiazole-5-yl)methoxy)phenyl)-4,5,6,7-tetrahydro-1H-isoindole-1,3(2H)-dione Compound B1

2-(4-chloro-2-fluoro-5-(5-(2-fluorophenyl)-1,3,4-oxadiazole-2-yl)methoxy)phenyl)-4,5,6,7-tetrahydro-1H-isoindole-1,3(2H)-dione Compound B2

2-(4-chloro-5-((5-(3-chlorophenyl)-1,3,4-oxadiazole-2-yl)methoxy)-2-fluorophenyl)-4,5,6,7-tetrahydro-1H-isoindole-1,3(2H)-dione Compound B3

2-(4-chloro-2-fluoro-5-(5-(3-tolyl)-1,3,4-oxadiazole-2-methoxy)phenyl)-4,5,6,7-tetrahydro-1H-isoindole-1,3(2H)-dione Compound B4

2-(4-chloro-2-fluoro-5-(5-(2-fluorophenyl)-1,3,4-oxadiazole-2-yl)methoxy)phenyl)-4,5,6,7-tetrahydro-1H-isoindole-1,3(2H)-dione Compound B5

2-(4-chloro-5-(5-(2-chlorophenyl)-1,3,4-oxadiazole-2-yl)methoxy)-2-fluorophenyl)-4,5,6,7-tetrahydro-1H-isoindole-1,3(2H)-dione Compound B6

2-(5-(5-(2-bromophenyl)-1,3,4-oxadiazole-2-yl)methoxy)-4-chloro-2-fluorophenyl)-4,5,6,7-tetrahydro-1H-isoindole-1,3(2H)-dione Compound B7

2-(4-chloro-2-fluoro-5-(5-(2-iodophenyl)-1,3,4-oxadiazole-2-yl)methoxy)phenyl)-4,5,6,7-tetrahydro-1H-isoindole-1,3(2H)-dione Compound B8

2-(4-chloro-2-fluoro-5-(5-(2-nitrophenyl)-1,3,4-oxadiazole-2-yl)methoxy)phenyl)-4,5,6,7-tetrahydro-1H-isoindole-1,3(2H)-dione Compound B9

2-(4-chloro-2-fluoro-5-((5-(2-tolyl)-1,3,4-oxadiazole-2-yl)methoxy)phenyl)-4,5,6,7-tetrahydro-1H-isoindole-1,3(2H)-dione Compound B10

2-(5-(5-(3-bromophenyl)-1,3,4-oxadiazole-2-yl)methoxy)-4-chloro-2-fluorophenyl)-4,5,6,7-tetrahydro-1H-isoindole-1,3(2H)-dione Compound B11

2-(4-chloro-2-fluoro-5-(5-(3-iodophenyl)-1,3,4-oxadiazole-2-yl)methoxy)phenyl)-4,5,6,7-tetrahydro-1H-isoindole-1,3(2H)-dione Compound B12

2-(4-chloro-2-fluoro-5-(5-(3-nitrophenyl)-1,3,4-oxadiazole-2-yl)methoxy)phenyl)-4,5,6,7-tetrahydro-1H-isoindole-1,3(2H)-dione Compound B13

2-(4-chloro-2-fluoro-5-((5-(4-tolyl)-1,3,4-oxadiazole-2-yl)methoxy)phenyl)-4,5,6,7-tetrahydro-1H-isoindole-1,3(2H)-dione Compound B14

2-(4-chloro-2-fluoro-5-(5-(4-fluorophenyl)-1,3,4-oxadiazole-2-yl)methoxy)phenyl)-4,5,6,7-tetrahydro-1H-isoindole-1,3(2H)-dione Compound B15

2-(4-chloro-5-(5-(4-chlorophenyl)-1,3,4-oxadiazole-2-yl)methoxy)-2-fluorophenyl)-4,5,6,7-tetrahydro-1H-isoindole-1,3(2H)-dione Compound B16

2-(4-chloro-2-fluoro-5-(5-(4-bromophenyl)-1,3,4-oxadiazole-2-yl)methoxy)phenyl)-4,5,6,7-tetrahydro-1H-isoindole-1,3(2H)-dione Compound B17

2-(4-chloro-2-fluoro-5-(5-(4-iodophenyl)-1,3,4-oxadiazole-2-yl)methoxy)phenyl)-4,5,6,7-tetrahydro-1H-isoindole-1,3(2H)-dione Compound B18

2-(4-chloro-2-fluoro-5-(5-(4-nitrophenyl)-1,3,4-oxadiazole-2-yl)methoxy)phenyl)-4,5,6,7-tetrahydro-1H-isoindole-1,3(2H)-dione Compound B19

2-(4-chloro-5-(5-(4-chloro-2-fluorophenyl)-1,3,4-oxadiazole-2-yl)methoxy)-2-fluorophenyl)-4,5,6,7-tetrahydro-1H-isoindole-1,3(2H)-dione Compound B20

2-(4-chloro-2-fluoro-5-(5-(2-fluoro-4-nitrophenyl)-1,3,4-oxadiazole-2-yl)methoxy)phenyl)-4,5,6,7-tetrahydro-1H-isoindole-1,3(2H)-dione Compound C1

2-(4-chloro-2-fluoro-5-(2-oxo-2-phenylethoxy)phenyl)-4,5,6,7-tetrahydro-1H-isoindole-1,3(2H)-dione Compound C2

2-(4-chloro-2-fluoro-5-(2-oxo-2-(4-methyl)ethoxy)phenyl)-4,5,6,7-tetrahydro-1H-isoindole-1,3(2H)-dione Compound C3

2-(4-chloro-2-fluoro-5-(2-oxo-2-(4-cyanophenyl)ethoxy)phenyl)-4,5,6,7-tetrahydro-1H-isoindole-1,3(2H)-dione Compound C4

2-(4-chloro-2-fluoro-5-(2-oxo-2-(2-fluorophenyl)ethoxy)phenyl)-4,5,6,7-tetrahydro-1H-isoindole-1,3(2H)-dione Compound C5

2-(4-chloro-2-fluoro-5-(2-oxo-2-(3,5-difluorophenyl)ethoxy)phenyl)-4,5,6,7-tetrahydro-1H-isoindole-1,3(2H)-dione Compound C6

2-(4-chloro-2-fluoro-5-(2-oxo-2-(2-methoxyphenyl)ethoxy)phenyl)-4,5,6,7-tetrahydro-1H-isoindole-1,3(2H)-dione Compound C7

2-(4-chloro-2-fluoro-5-(2-oxo-2-(3-fluorophenyl)ethoxy)phenyl)-4,5,6,7-tetrahydro-1H-isoindole-1,3(2H)-dione Compound C8

2-(4-chloro-2-fluoro-5-(2-oxo-2-(4-fluorophenyl)ethoxy)phenyl)-4,5,6,7-tetrahydro-1H-isoindole-1,3(2H)-dione Compound C9

2-(4-chloro-2-fluoro-5-(2-oxo-2-(4-nitrophenyl)ethoxy)phenyl)-4,5,6,7-tetrahydro-1H-isoindole-1,3(2H)-dione Compound C10

2-(4-chloro-2-fluoro-5-((4-fluorobenzyl)oxy)phenyl)-4,5,6,7-tetrahydro-1H-isoindole-1,3(2H)-dione Compound C11

2-(4-chloro-2-fluoro-5-(2-oxo-2-(4-chlorophenyl)ethoxy)phenyl)-4,5,6,7-tetrahydro-1H-isoindole-1,3(2H)-dione Compound C12

2-(4-chloro-2-fluoro-5-(2-oxo-2-(2,4-difluorophenyl)ethoxy)phenyl)-4,5,6,7-tetrahydro-1H-isoindole-1,3(2H)-dione Compound C13

2-(4-chloro-2-fluoro-5-(2-oxo-2-(4-methoxyphenyl)ethoxy)phenyl)-4,5,6,7-tetrahydro-1H-isoindole-1,3(2H)-dione Compound C14

2-(4-chloro-2-fluoro-5-(2-oxo-2-(4-bromophenyl)ethoxy)phenyl)-4,5,6,7-tetrahydro-1H-isoindole-1,3(2H)-dione Compound C15

2-(2-fluoro-4-(2-oxo-2-(4-tolyl)ethoxy)phenyl)-4,5,6,7-tetrahydro-1H-isoindole-1,3(2H)-dione Compound D1

N-(2-chloro-5-(1,3-dioxo-1,3,4,5,6,7-hexahydro-2H-isoindole-2-yl)-4-fluorophenyl)acetamide Compound D2

2-chloro-N-(2-chloro-5-(1,3-dioxo-1,3,4,5,6,7-hexahydro-2H-isoindole-2-yl)-4-fluorophenyl)acetamide Compound D3

2-bromo-N-(2-chloro-5-(1,3-dioxo-1,3,4,5,6,7-hexahydro-2H-isoindol-2-yl)-4-fluorophenyl)propionamide Compound D4

3-chloro-N-(2-chloro-5-(1,3-dioxo-1,3,4,5,6,7-hexahydro-2H-isoindole-2-yl)-4-fluorophenyl)-2,2-dimethylpropionamide Compound D5

(E)-N-(2-chloro-5-(1,3-dioxo-1,3,4,5,6,7-hexahydro-2H-isoindole-2-yl)-4-fluorophenyl)but-2-enamide Compound D6

3-((2-chloro-5-(1,3-dioxo-1,3,4,5,6,7-hexahydro-2H-isoindole-2-yl)-4-fluorophenyl)amino)-ethyl 3-oxopropanoate Compound D7

N-(2-chloro-5-(1,3-dioxo-1,3,4,5,6,7-hexahydro-2H-isoindole-2-yl)-4-fluorophenyl)nonanamide Compound D8

N-(2-chloro-5-(1,3-dioxo-1,3,4,5,6,7-hexahydro-2H-isoindole-2-yl)-4-fluorophenyl)cyclopropanecarboxamide Compound D9

N-(2-chloro-5-(1,3-dioxo-1,3,4,5,6,7-hexahydro-2H-isoindole-2-yl)-4-fluorophenyl)cyclobutanecarboxamide Compound D10

N-(2-chloro-5-(1,3-dioxo-1,3,4,5,6,7-hexahydro-2H-isoindole-2-yl)-4-fluorophenyl)cyclohexanecarboxamide Compound E1

2-(4-chlorophenyl)-2-oxoethyl-2-chloro-5-(1,3-dioxo-1,3,4,5,6,7-hexahydro-2H-isoindole-2-yl)-4-fluorobenzoate; and Compound E2

2-oxo-2-phenylethyl-2-chloro-5-(1,3-dioxo-1,3,4,5,6,7-hexahydro-2H-isoindole-2-yl)-4-fluorobenzoate The present disclosure further provides a method for preparing the N-phenylimine derivative.

In the present disclosure, unless otherwise specified, all raw materials/components for preparation are commercially available products well known to those skilled in the art.

In the present disclosure, a compound represented by formula 5, an alkali metal carbonate, a compound represented by formula 6 and an organic solvent I are mixed to obtain a mixture I, and the mixture I is subjected to nucleophilic substitution to obtain the 1,2,4-oxadiazole-N-phenylimine derivative represented by formula 1, formula 5

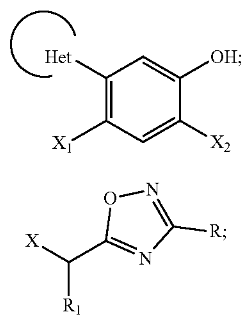

formula 6

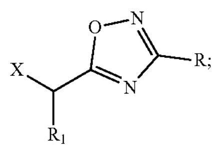

in formula 6, X is selected from the group consisting of Cl and Br.

In some embodiments, the compound represented by formula 5 is selected from the group consisting of a compound represented by 5-1, a compound represented by formula 5-2, a compound represented by formula 5-3, and a compound represented by formula 5-4. In some embodiments, the compound represented by formula 5-1, formula 5-2, formula 5-3, or formula 5-4 is prepared by a process including the following steps:

mixing a compound represented by formula 11, an ethanol-aqueous solution, ammonium chloride, and an iron powder to obtain a mixture V-1, and subjecting the mixture V to reduction to obtain a compound represented by formula 12; and mixing the compound represented by formula 12, glacial acetic acid, and a diketone compound to obtain a mixture V-2, and subjecting the mixture V-2 to nucleophilic substitution to obtain the compound represented by formula 5-1, formula 5-2, formula 5-3, or formula 5-4; wherein the diketone compound is selected from the group consisting of 4,5,6,7-tetrahydroisobenzofuran-1,3-dione, isobenzofuran-1,3-dione, 3-methylenedihydrofuran-2,5-dione, and 3-methylenedihydrofuran-2,5-dione, formula 11

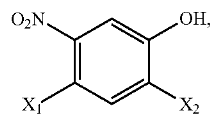

formula 12

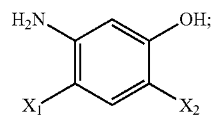

formula 5-1

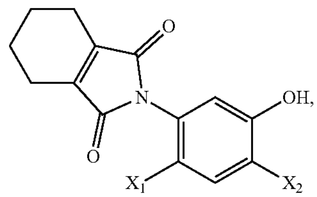

formula 5-2

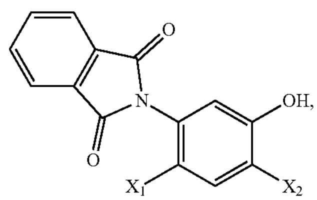

formula 5-3

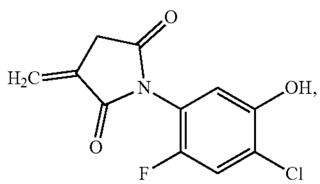

formula 5-4

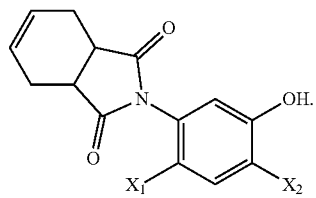

In some embodiments, a compound represented by formula 11, an ethanol-aqueous solution, ammonium chloride, and an iron powder are mixed to obtain a mixture V-1, and the mixture V-1 is subjected to reduction to obtain a compound represented by formula 12. In some embodiments, the ethanol-aqueous solution has a volume percentage of ethanol of 90%; a molar ratio of the compound represented by formula 11 to the ammonium chloride is 52.21:156.62; a molar ratio of the compound represented by formula 11 to the iron powder is 52.21:156.62; and the reduction is conducted under reflux. In some embodiments, after the reduction, a reduction reaction solution is obtained; the reduction reaction solution is subjected to post-treatment to obtain the compound represented by formula 12. In some embodiments, the post-treatment includes the following steps: subjecting the reduction reaction solution to solid-liquid separation to obtain a solid-phase product and a liquid-phase product; washing the solid-phase product three times; mixing the liquid-phase product with a washing solution to obtain a mixed solution, and subjecting the mixed solution to concentration to obtain a solid product, and recrystallizing the solid product with ethanol to obtain the compound represented by formula 12. In some embodiments, the solid-liquid separation is conducted by suction filtration, the suction filtration is conducted under the condition that the mixed solution is hot, and the washing is preferably conducted three times with hot ethanol.

In some embodiments, the compound represented by formula 11 is specifically a compound represented by formula 11-1:

formula 11-1

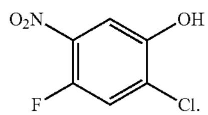

In some embodiments, after obtaining the compound represented by formula 12, the compound represented by formula 12, glacial acetic acid, and a diketone compound are mixed to obtain a mixture V-2, and the mixture V-2 is subjected to nucleophilic substitution to obtain the compound represented by formula 5-1, formula 5-2, formula 5-3, or formula 5-4; wherein the diketone compound is selected from the group consisting of 4,5,6,7-tetrahydroisobenzofuran-1,3-dione, isobenzofuran-1,3-dione, 3-methylenedihydrofuran-2,5-dione, and 3-methylenedihydrofuran-2,5-dione. In some embodiments, a molar ratio of the compound represented by formula 12 to the diketone compound is 43.33:47.66. In some embodiments, the nucleophilic substitution is conducted at 100° C. After the nucleophilic substitution, a resulting reaction solution is poured into ice water to obtain a reaction solution-water mixed solution. After a large amount of solid product is precipitated in the reaction solution-water mixed solution, the reaction solution-water mixed solution is filtered to obtain the compound represented by formula 5-1, formula 5-2, formula 5-3, or formula 5-4.

In some embodiments, the compound represented by formula 5-1 is

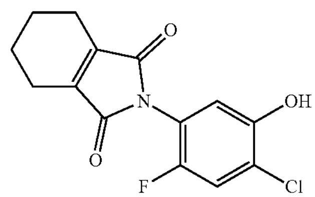 [SMILES: O=C1C2=C(CCCC2)C(=O)N1c1cc(O)c(Cl)cc1F]

(chemical name: 2-(4-chloro-2-fluoro-5-hydroxybenzene)-4,5,6,7-tetrahydro-1H-isoindole-1,3(2H)-dione). A reaction equation is as follows:

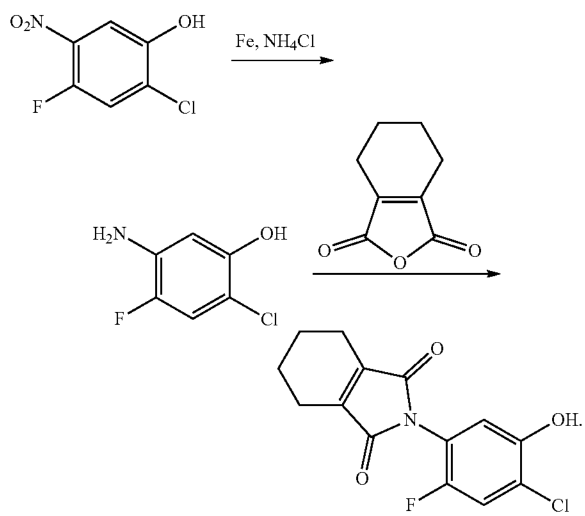

In some embodiments, the compound represented by formula 5-2 is

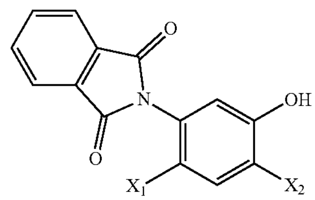

(chemical name: 2-(4-chloro-2-fluoro-5-hydroxyphenyl) isoindole-1,3-dione). A reaction equation is as follows:

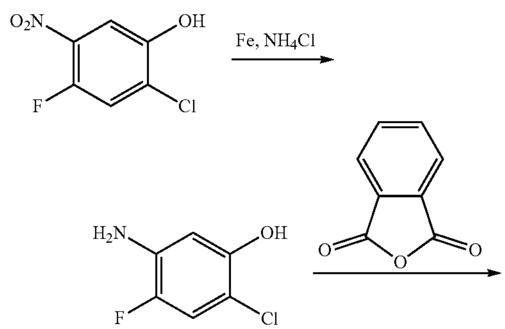

-continued

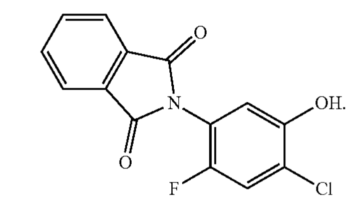

In some embodiments, the compound represented by formula 5-3 is

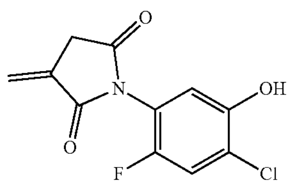 [SMILES: C=C1CC(=O)N(c2cc(O)c(Cl)cc2F)C1=O]

(chemical name: 1-(4-chloro-2-fluoro-5-hydroxybenzene)-3-methylenepyrrolidine-2,5-dione). A reaction equation is as follows:

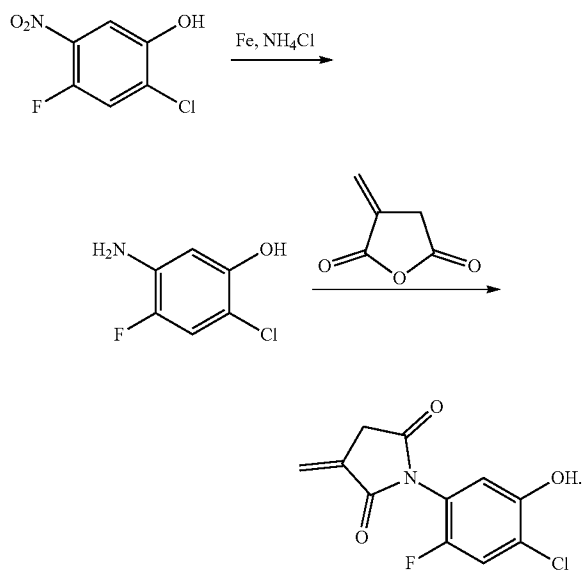

In some embodiments, the compound represented by formula 5-4 is

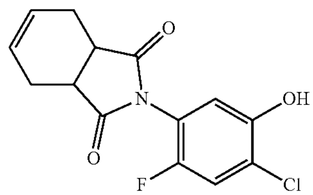 [SMILES: O=C1C2CC=CCC2C(=O)N1c1cc(O)c(Cl)cc1F]

(chemical name: 2-(4-chloro-2-fluoro-5-hydroxybenzene)-3a,4,7,7a-tetrahydro-1H-isoindole-1,3(2H)-dione). A reaction equation is as follows:

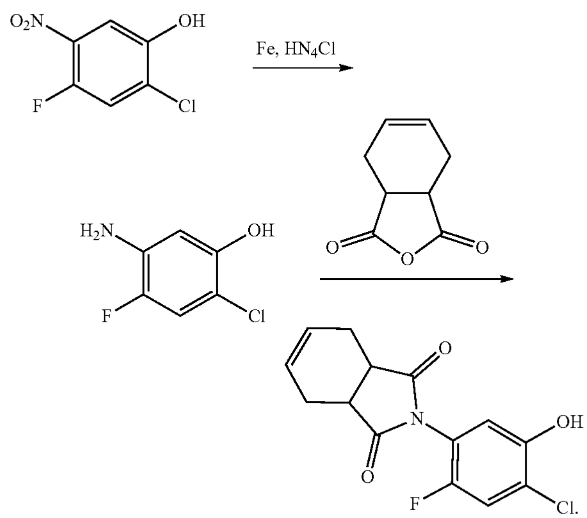

In the present disclosure, the compound represented by formula 6 is prepared by a process including the following steps:

mixing a compound represented by formula 13, an organic solvent VI-1, and neutral hydroxylamine hydrochloride to obtain a mixture VI-1, and subjecting the mixture VI-1 to amidoximation to obtain a compound represented by formula 14; and mixing the compound represented by formula 14, a compound represented by formula 15, triethylamine and an organic solvent VI-2 to obtain a mixture VI-2, and subjecting the mixture VI-2 to ring formation to obtain the compound represented by formula 6;

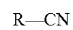

formula 13, formula 14

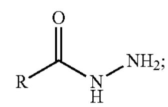

formula 15

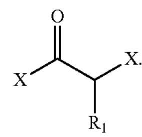

In some embodiments, a compound represented by formula 13, an organic solvent VI-1, and neutral hydroxylamine hydrochloride are mixed to obtain a mixture VI-1, and the mixture VI-1 is subjected to amidoximation to obtain a compound represented by formula 14. In some embodiments, the compound represented by formula 13 is selected from the group consisting of: compounds represented by formula 13-1

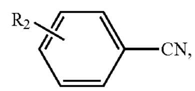

formula 13-2

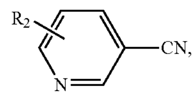

-continued formula 13-3

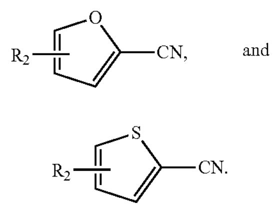

and formula 13-4

In some embodiments, the organic solvent VI-1 is ethanol. In some embodiments, a molar ratio of the compound represented by formula 13 to the neutral hydroxylamine hydrochloride is 25.5:76.51. In some embodiments, the amidoximation is conducted under reflux by heating. In some embodiments, the completion of the amidoximation is monitored by thin-layer chromatography (TLC). In some embodiments, after the amidoximation is completed, an obtained reaction solution is subjected to desolvation, and then extracted with dichloromethane to obtain an extracted organic phase, and the extracted organic phase is subjected to drying and purification to obtain the compound represented by formula 13. In some embodiments, the desolvation is conducted by vacuum distillation. In some embodiments, the drying is conducted with anhydrous sodium sulfate. In some embodiments, the purification is conducted by recrystallization or column chromatography.

In some embodiments, after obtaining the compound represented by formula 14, the compound represented by formula 14, a compound represented by formula 15, triethylamine and an organic solvent VI-2 are mixed to obtain a mixture VI-2, and the mixture VI-2 is subjected to ring formation to obtain the compound represented by formula 6. In some embodiments, the compound represented by formula 15 is chloroacetyl chloride or chloropropionyl chloride. In some embodiments, the organic solvent VI-2 is toluene. In some embodiments, a molar ratio of the compound represented by formula 14 to the compound represented by formula 15 to triethylamine is 21.83:43.65:21.83. In some embodiments, the ring formation is conducted under reflux by heating. In some embodiments, a reaction solution obtained after the ring formation is extracted with ethyl acetate to obtain an extracted organic phase; the extracted organic phase is subjected to drying and concentration to obtain a concentrated solution, and the concentrated solution is subjected to purification to obtain the compound represented by formula 6. In some embodiments, the drying is conducted with anhydrous sodium sulfate. In some embodiments, the purification is conducted by column chromatography.

In some embodiments, the compound represented by formula 6 is a compound represented by formula 6-1:

formula 6-1

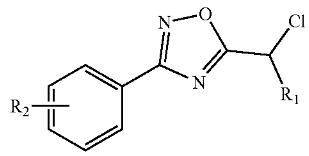

(a 5-(chloroethyl)-3-phenyl-1,2,4-oxadiazole derivative). A reaction equation is as follows:

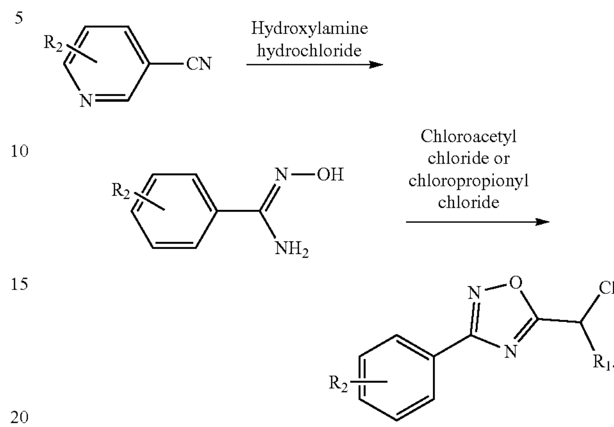

In some embodiments, the compound represented by formula 6 is a compound represented by formula 6-2:

formula 6-2

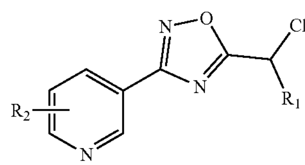

(a 5-(chloroethyl)-3-pyridine-1,2,4-oxadiazole derivative). A reaction equation is as follows:

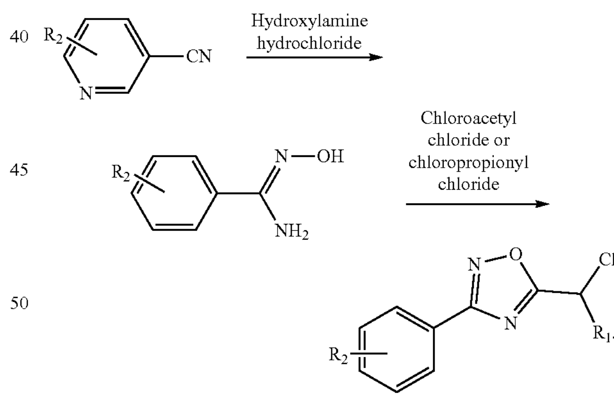

In some embodiments, the compound represented by formula 6 is a compound represented by formula 6-3:

formula 6-3

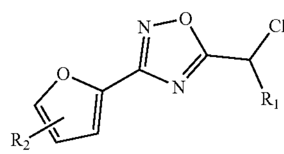

(a 5-(chloroethyl)-3-furan-1,2,4-oxadiazole derivative). A reaction equation is as follows:

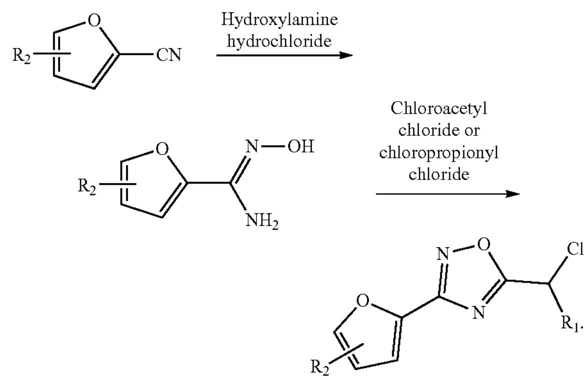

In some embodiments, the compound represented by formula 6 is a compound represented by formula 6-4:

formula 6-4

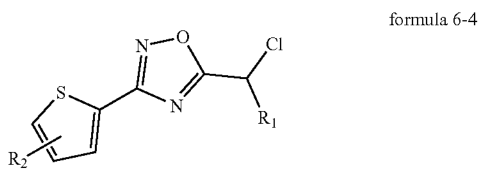

(a 5-(chloroethyl)-3-thiophene-1,2,4-oxadiazole derivative). A reaction equation is as follows:

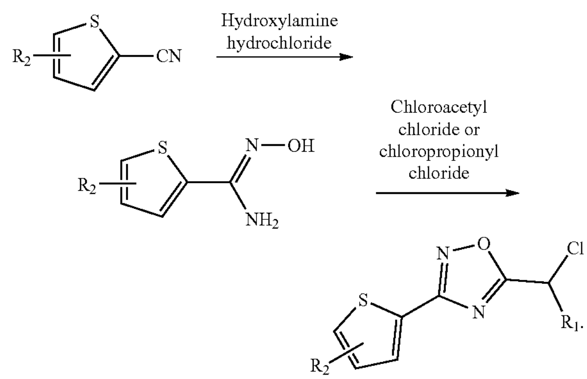

In some embodiments, the 1,2,4-oxadiazole-N-phenylimine derivative represented by formula 1 is selected from the of a group consisting of a 2-(4-chloro-2-fluoro-5-((5-phenyl-1,2,4-oxadiazole-3-yl)methoxy)aryl)-4,5,6,7-tetrahydro-1H-isoindole-1,3(2H)-dione derivative, a 2-(4-chloro-2-fluoro-5-(3-phenyl-1,2,4-oxadiazole-5-yl) methoxy)aryl)isoindole-1,3-dione derivative, a 2-(4-chloro-2-fluoro-5-((5-phenyl-1,2,4-oxadiazole-3-yl)methoxy)aryl)-3a,4,7,7a-tetrahydro-1H-isoindole-1,3(2H)-dione derivative, and a 1-(4-chloro-2-fluoro-5-((5-phenyl-1,2,4-oxadiazole-3-)methoxy)aryl)-3-methylenepyrrolidine-2,5-dione derivative.

In some embodiments, the 2-(4-chloro-2-fluoro-5-((5-phenyl-1,2,4-oxadiazole-3-yl)methoxy)aryl)-4,5,6,7-tetrahydro-1H-isoindole-1,3(2H)-dione derivative is prepared by a process including: at ambient temperature, dissolving 2-(4-chloro-2-fluoro-5-hydroxybenzene)-4,5,6,7-tetrahydro-1H-isoindole-1,3(2H)-dione in acetone, adding potassium carbonate, and stirring for 30 min; adding a 1,2,4-oxadiazole derivative, and conducting a reaction under reflux; conducting filtration to remove potassium carbonate, followed by extraction, drying by anhydrous sodium sulfate, concentration, and purification with silica gel chromatography to obtain a target compound, namely the 2-(4-chloro-2-fluoro-5-((5-phenyl-1,2,4-oxadiazole-3-yl)methoxy)aryl)-4,5,6,7-tetrahydro-1H-isoindole-1,3(2H)-dione derivative. A reaction equation is as follows:

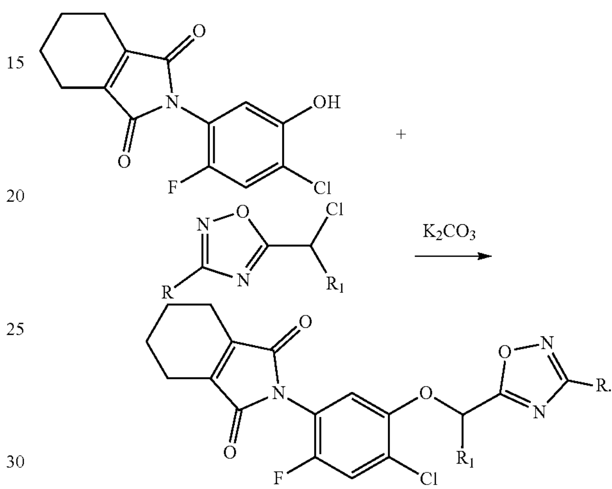

In some embodiments, the 2-(4-chloro-2-fluoro-5-(3-phenyl-1,2,4-oxadiazole-5-yl)methoxy)aryl)isoindole-1,3-dione derivative is prepared by a process including: at ambient temperature, dissolving 2-(4-chloro-2-fluoro-5-hydroxyphenyl)isoindole-1,3-dione in acetone, adding potassium carbonate, and stirring for 30 min; adding a 1,2,4-oxadiazole derivative, and conducting a reaction under reflux; conducting filtration to remove potassium carbonate, followed by extraction, drying by anhydrous sodium sulfate, concentration, and purification with silica gel chromatography to obtain a target compound, namely the 2-(4-chloro-2-fluoro-5-(3-phenyl-1,2,4-oxadiazole-5-yl)methoxy)aryl)isoindole-1,3-dione derivative. A reaction equation is as follows:

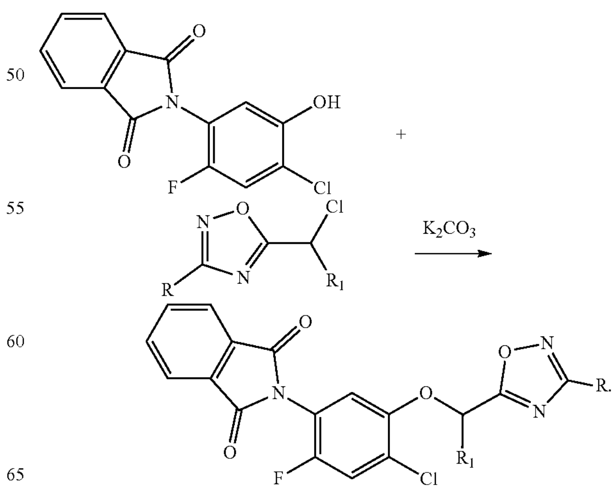

In some embodiments, the 2-(4-chloro-2-fluoro-5-((5-phenyl-1,2,4-oxadiazole-3-yl)methoxy)aryl)-3a,4,7,7a-tetrahydro-1H-isoindole-1,3(2H)-dione derivative is prepared by a process including: at ambient temperature, dissolving 2-(4-chloro-2-fluoro-5-hydroxybenzene)-3a,4,7,7a-tetrahydro-1H-isoindole-1,3(2H)-dione in acetone, adding potassium carbonate, and stirring for 30 min; adding a 1,2,4-oxadiazole derivative, and conducting a reaction under reflux; conducting filtration to remove potassium carbonate, followed by extraction, drying by anhydrous sodium sulfate, concentration, and purification with silica gel chromatography to obtain a target compound, namely the 2-(4-chloro-2-fluoro-5-((5-phenyl-1,2,4-oxadiazole-3-yl)methoxy)aryl)-3a,4,7,7a-tetrahydro-1H-isoindole-1,3(2H)-dione derivative. A reaction equation is as follows:

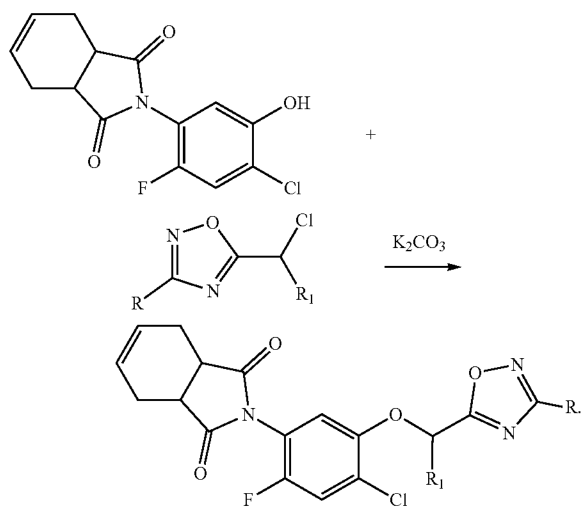

In some embodiments, the 1-(4-chloro-2-fluoro-5-((5-phenyl-1,2,4-oxadiazole-3-)methoxy)aryl)-3-methylenepyrrolidine-2,5-dione derivative is prepared by a process including: at ambient temperature, dissolving 1-(4-chloro-2-fluoro-5-hydroxybenzene)-3-methylenepyrrolidine-2,5-dione in acetone, adding potassium carbonate, and stirring for 30 min; adding a 1,2,4-oxadiazole derivative, and conducting a reaction under reflux; conducting filtration to remove potassium carbonate, followed by extraction, drying by anhydrous sodium sulfate, concentration, and purification with silica gel to chromatography obtain a target compound, namely the 1-(4-chloro-2-fluoro-5-((5-phenyl-1,2,4-oxadiazole-3-)methoxy)aryl)-3-methylenepyrrolidine-2,5-dione derivative. A reaction equation is as follows:

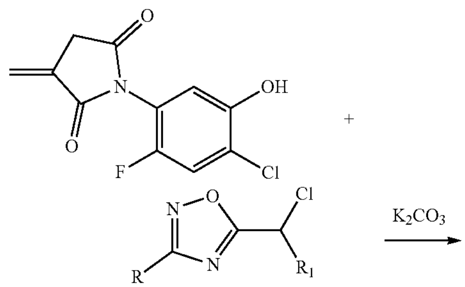

-continued

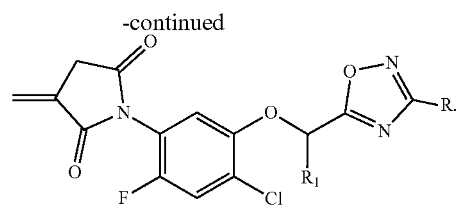

In the present disclosure, the compound represented by formula 5, an alkali metal carbonate, a compound represented by formula 7 and an organic solvent II are mixed to obtain a mixture II, and the mixture II is subjected to nucleophilic substitution to obtain the 1,3,4-oxadiazole-N-phenylimine derivative represented by formula 2.

In some embodiments, the compound represented by formula 7 is prepared by a process including the following steps:

mixing a compound represented by formula 16, an alcohol solvent, and hydrazine hydrate to obtain a mixture VII-1, and subjecting the mixture VII-1 to acylation to obtain a compound represented by formula 17, and mixing the compound represented by formula 17 with a compound represented by formula 18, an organic solvent VII, and phosphorus oxychloride to obtain a mixture VII-2, and subjecting the mixture VII-2 to ring formation to obtain the compound represented by formula 7;

formula 16

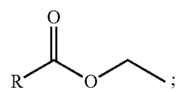

formula 17

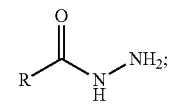

formula 18

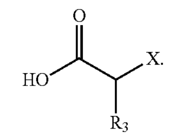

In some embodiments, the compound represented by formula 7 is selected from the group consisting of: a 5-(chloroethyl)-3-phenyl-1,3,4-oxadiazole derivative, a 5-(chloroethyl)-3-pyridine-1,3,4-oxadiazole derivative, a 5-(chloroethyl)-3-furan-1,3,4-oxadiazole derivative, and a 5-(chloroethyl)-3-thiophene-1,3,4-oxadiazole derivative.

In some embodiments, the 5-(chloroethyl)-3-phenyl-1,3,4-oxadiazole derivative is prepared by a process including:

adding concentrated sulfuric acid dropwise to a substituted benzoic acid containing different substituents in ethanol under ice bath, and conducting a reaction under reflux by heating: after cooling, adjusting pH of a resulting reaction product to neutral, extracting with ethyl acetate to obtain a first organic phase, subjecting the first organic phase to drying by anhydrous sodium sulfate, concentration and purification with column chromatography to obtain a substituted ethyl benzoate with different substituents;

adding hydrazine hydrate dropwise to the substituted ethyl benzoate with different substituents in ethanol, and conducting a reaction under reflux by heating, wherein the reaction is monitored by TLC; after the reaction, removing the solvent, and extracting a resulting product with ethyl acetate to obtain a second organic phase, subjecting the second organic phase to washing with saturated brine, drying by anhydrous sodium sulfate, concentration, and purification with column chromatography to obtain a substituted benzoyl hydrazine with different substituents; and adding chloroacetic acid and phosphorus oxychloride to the benzoyl hydrazine in 1,2-dichloroethane under ice bath, and then reacting under reflux; after the reaction, quenching a resulting reaction system with ice water, adjusting pH of the resulting reaction system to neutral with sodium bicarbonate, and then extracting with dichloromethane to obtain a third organic phase; subjecting the third organic phase to drying with anhydrous sodium sulfate, concentration, and purification with column chromatography to obtain the 5-(chloroethyl)-3-phenyl-1,3,4-oxadiazole derivative. A reaction equation is as follows:

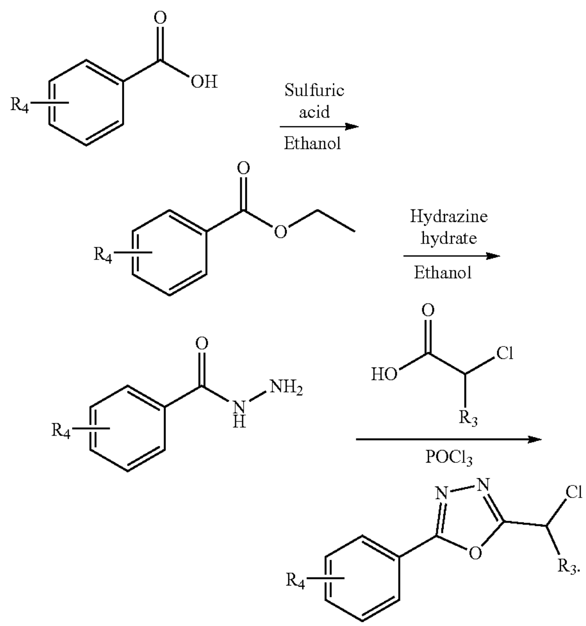

In some embodiments, the 5-(chloroethyl)-3-pyridine-1,3,4-oxadiazole derivative is prepared by a process including:

slowly adding hydrazine hydrate dropwise to a substituted ethyl picolinate with different substituents in ethanol, and conducting a reaction under reflux by heating, wherein the reaction is monitored by TLC; after the reaction, removing the solvent, extracting a resulting product with ethyl acetate to obtain a first organic phase, subjecting the first organic phase to washing with saturated brine, drying with anhydrous sodium sulfate, concentration, and purification with column chromatography to obtain a substituted pyridine formylhydrazine with different substituents, and adding chloroacetic acid and phosphorus oxychloride to the substituted pyridine formylhydrazine in 1,2-dichloroethane under ice bath, and then reacting under reflux; after the reacting, quenching a resulting reaction system with ice water, adjusting pH of the resulting reaction system to neutral with sodium bicarbonate, and then extracted with dichloromethane to obtain a second organic phase; and subjecting the second organic phase to drying with anhydrous sodium sulfate, concentration, and purification with column chromatography to obtain the 5-(chloroethyl)-3-pyridyl-1,3,4-oxadiazole derivative. A reaction equation is as follows:

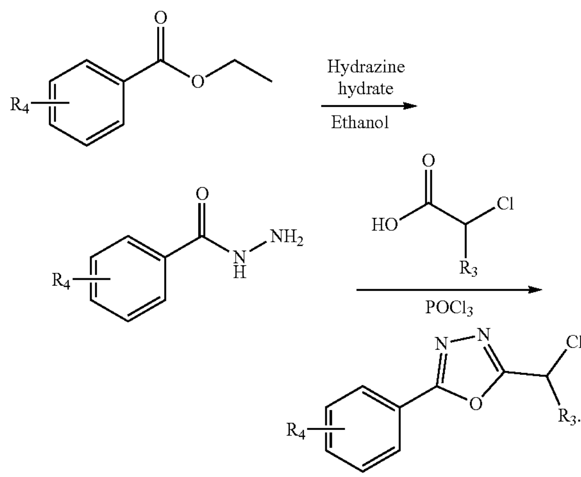

In some embodiments, the 5-(chloroethyl)-3-furan-1,3,4-oxadiazole derivative is prepared by a process including:

slowly adding hydrazine hydrate dropwise to a substituted ethyl furoate containing different substituents in ethanol, and heating under reflux and then subjecting to reaction, wherein the reaction is monitored by TLC; after the reaction, removing the solvent, and extracting a resulting product with ethyl acetate to obtain a first organic phase, subjecting the first organic phase to washing with saturated brine, drying with anhydrous sodium sulfate, concentration, and purification with column chromatography to obtain a substituted furoyl hydrazine containing different substituents; and adding chloroacetyl chloride and phosphorus oxychloride to the substituted furoyl hydrazine in 1,2-dichloroethane under ice bath, and then reacting under reflux; after the reacting, quenching a resulting reaction system with ice water, adjusting pH of the resulting reaction system to neutral with sodium bicarbonate, and then extracting with dichloromethane to obtain a second organic phase; and subjecting the second organic phase to drying with anhydrous sodium sulfate, concentration, and purification with column chromatography to obtain the 5-(chloroethyl)-3-furyl-1,3,4-oxadiazole derivative. A reaction equation is as follows:

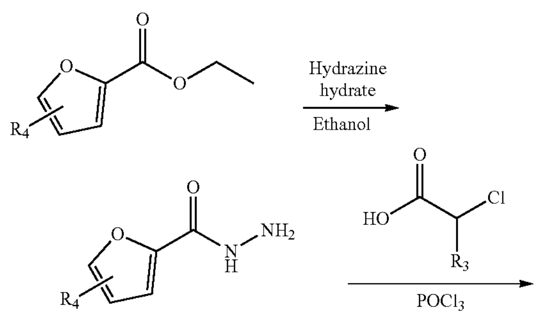

-continued

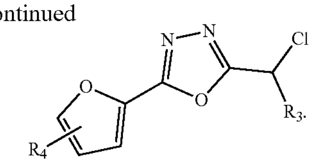

In some embodiments, the 5-(chloroethyl)-3-thiophene-1,3,4-oxadiazole derivative is prepared by a process including:

slowly adding hydrazine hydrate dropwise into a substituted ethyl thiophenecarboxylate containing different substituents in ethanol, and heating under reflux and then subjecting to reaction, wherein the reaction is monitored by TLC; after the reaction, removing the solvent, and extracting a resulting product with ethyl acetate to obtain a first organic phase, and subjecting the first organic phase to washing with saturated brine, drying with anhydrous sodium sulfate, concentration, and then purification with column chromatography to obtain a substituted thienyl hydrazide containing different substituents, and adding chloroacetyl chloride and phosphorus oxychloride into the substituted thienyl hydrazide in 1,2-dichloroethane under ice bath, and then reacting under reflux; after the reacting, quenching a resulting reaction system with ice water, adjusting pH of the resulting reaction system to neutral with sodium bicarbonate, and then extracting with dichloromethane to obtain a second organic phase, and subjecting the second organic phase to drying with anhydrous sodium sulfate, concentration, and purification with column chromatography to obtain the 5-(chloroethyl)-3-thienyl-1,3,4-oxadiazole derivative. A reaction equation is as follows:

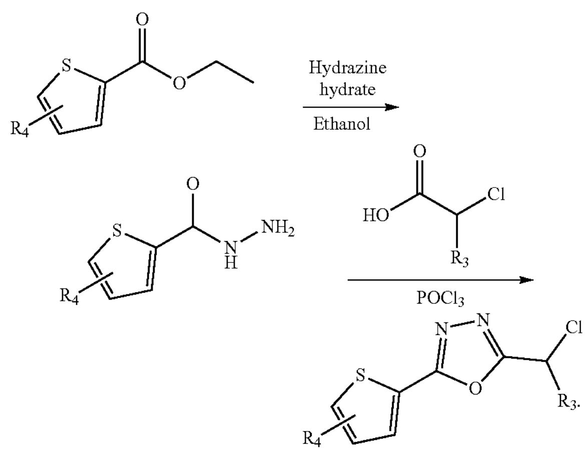

In some embodiments, the 1,3,4-oxadiazole-N-phenylimine derivative represented by formula 2 is selected from the group consisting of a 2-(4-chloro-2-fluoro-5-((5-phenyl-1,3,4-oxadiazole-3-yl)methoxy)aryl)-4,5,6,7-tetrahydro-1H-isoindole-1,3(2H)-dione derivative, a 2-(4-chloro-2-fluoro-5-(3-phenyl-1,3,4-oxadiazole-5-yl)methoxy)aryl)isoindole-1,3-dione derivative, a 2-(4-chloro-2-fluoro-5-((5-phenyl-1,3,4-oxadiazole-3-yl)methoxy)aryl)-3a,4,7,7a-tetrahydro-1H-isoindole-1,3(2H)-dione derivative, and a 1-(4-chloro-2-fluoro-5-((5-phenyl-1,3,4-oxadiazole-3-)methoxy)aryl)-3-methylenepyrrolidine-2,5-dione derivative.

In some embodiments, the 2-(4-chloro-2-fluoro-5-((5-phenyl-1,3,4-oxadiazole-3-yl)methoxy)aryl)-4,5,6,7-tetrahydro-1H-isoindole-1,3(2H)-dione derivative is prepared by a process including: at ambient temperature, dissolving 2-(4-chloro-2-fluoro-5-hydroxybenzene)-4,5,6,7-tetrahydro-1H-isoindole-1,3(2H)-dione in acetone, adding potassium carbonate, and stirring for 30 min; then adding a 1,3,4-oxadiazole derivative, and conducting a reaction under reflux; filtering a resulting reaction system to remove potassium carbonate, followed by extraction to obtain an organic phase, and subjecting the organic phase to drying with anhydrous sodium sulfate, concentration, and purification with silica gel chromatography to obtain a target compound, namely the 2-(4-chloro-2-fluoro-5-((5-phenyl-1,3,4-oxadiazole-3-yl)methoxy)aryl)-4,5,6,7-tetrahydro-1H-isoindole-1,3(2H)-dione derivative. A reaction equation is as follows:

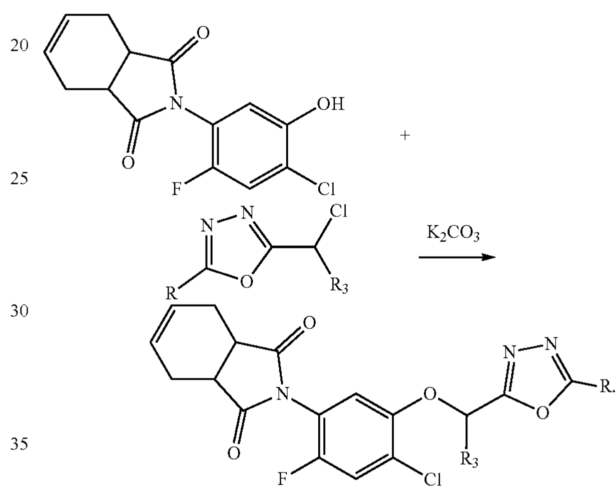

In some embodiments, the 2-(4-chloro-2-fluoro-5-(3-phenyl-1,3,4-oxadiazole-5-yl)methoxy)aryl)isoindole-1,3-dione derivative is prepared by a process including: at ambient temperature, dissolving 2-(4-chloro-2-fluoro-5-hydroxyphenyl)isoindole-1,3-dione in acetone, adding potassium carbonate, and stirring for 30 min; adding a 1,3,4-oxadiazole derivative, and conducting a reaction under reflux; filtering a resulting reaction system to remove potassium carbonate, followed by extraction to obtain an organic phase, and subjecting the organic phase to drying with anhydrous sodium sulfate, concentration, and purification with silica gel chromatography to obtain a target compound, namely the 2-(4-chloro-2-fluoro-5-(3-phenyl-1,3,4-oxadiazole-5-yl) methoxy)aryl)isoindole-1,3-dione derivative. A reaction equation is as follows:

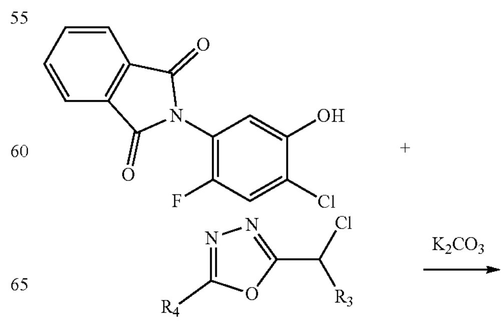

-continued

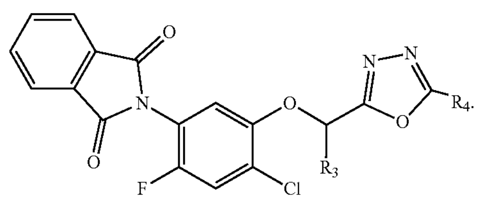

In some embodiments, the 2-(4-chloro-2-fluoro-5-((5-phenyl-1,3,4-oxadiazole-3-yl)methoxy)aryl)-3a,4,7,7a-tetrahydro-1H-isoindole-1,3(2H)-dione derivative is prepared by a process including: at ambient temperature, dissolving 2-(4-chloro-2-fluoro-5-hydroxybenzene)-3a,4,7,7a-tetrahydro-1H-isoindole-1,3(2H)-dione in acetone, adding potassium carbonate, and stirring for 30 min; adding a 1,3,4-oxadiazole derivative, and conducting a reaction under reflux; filtering a resulting reaction system to remove potassium carbonate, followed by extraction to obtain an organic phase, and subjecting the organic phase to drying with anhydrous sodium sulfate, concentration, and purification with silica gel chromatography to obtain a target compound, namely the 2-(4-chloro-2-fluoro-5-((5-phenyl-1,3,4-oxadiazole-3-yl)methoxy)aryl)-3a,4,7,7a-tetrahydro-1H-isoindole-1,3(2H)-dione derivative. A reaction equation is as follows:

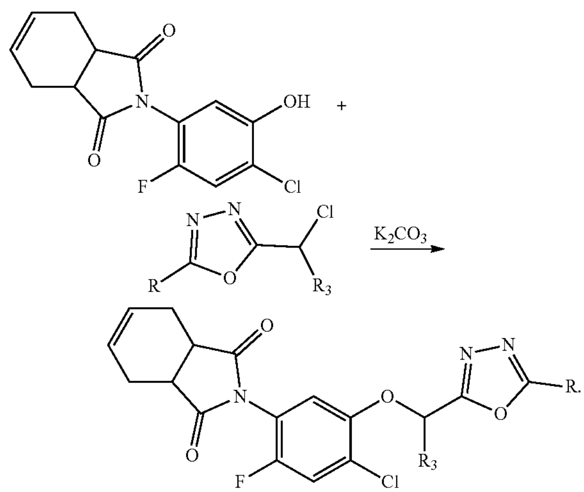

In some embodiments, the 1-(4-chloro-2-fluoro-5-((5-phenyl-1,3,4-oxadiazole-3-)methoxy)aryl)-3-methylenepyrrolidine-2,5-dione derivative is prepared by a process including: at ambient temperature, dissolving 1-(4-chloro-2-fluoro-5-hydroxybenzene)-3-methylenepyrrolidine-2,5-dione in acetone, adding potassium carbonate, and stirring for 30 min; adding a 1,3,4-oxadiazole derivative, and conducting a reaction under reflux; filtering a resulting reaction system to remove potassium carbonate, followed by extraction to obtain an organic phase, and subjecting the organic phase to drying with anhydrous sodium sulfate, concentration, and purification with silica gel chromatography to obtain a target compound, namely the 1-(4-chloro-2-fluoro-5-((5-phenyl-1,3,4-oxadiazole-3-)methoxy)aryl)-3-methylenepyrrolidine-2,5-dione derivative. A reaction equation is as follows:

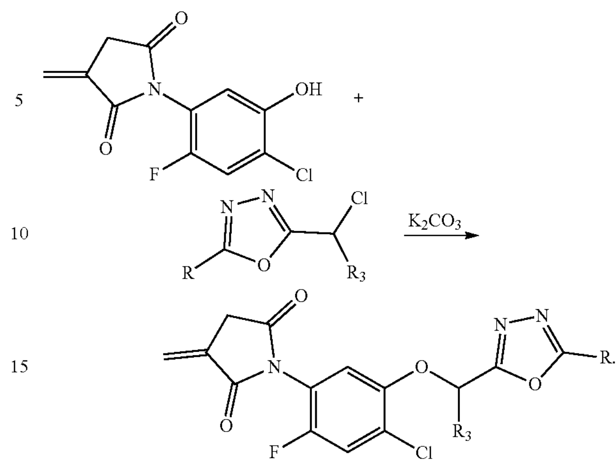

In some embodiments, under a condition that A in formula 3 is selected from the group consisting of O and S, the compound represented by formula 5, an alkali metal carbonate, a compound represented by formula 8, and an organic solvent III-1 are mixed to obtain a mixture III-1, and the mixture III-1 is subjected to nucleophilic substitution to obtain the N-phenylimine amide (ester) derivative represented by formula 3; wherein formula 5

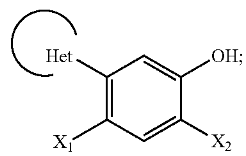

$X—R_5$ formula 8; in formula 8, X is selected from the group consisting of Cl and Br.

In some embodiments, the compound represented by formula 8 is an α-bromo(chloro)acetophenone derivative.

In some embodiments, the α-bromo(chloro)acetophenone derivative is prepared by a process including: adding an substituted acetophenone containing different substituents into water, and then heating to 90° C. under stirring; slowly adding liquid bromine dropwise into an obtained system, and holding at 90° C. and then subjecting to reaction; after the reaction, cooling an obtained reaction solution to ambient temperature to obtain a cooled reaction solution, filtering the cooled reaction solution to obtain a solid, and subjecting the solid to recrystallization to obtain the α-bromo(chloro) acetophenone derivative. A reaction equation is:

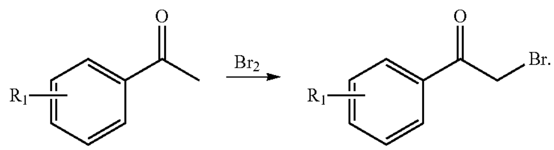

In some embodiments, under a condition that A in formula 3 is O or S, the N-phenylimine amide (ester) derivative represented by formula 3 is selected from the group consisting of a 2-(4-chloro-2-fluoro-5-(2-oxo-2-phenylethoxy)phenyl)-4,5,6,7-tetrahydro-1H-isoindole-1,3(2H)-dione derivative, a 2-(4-chloro-2-fluoro-5-(2-oxo-2-phenylethoxy)phenyl)isoindoline-1,3-dione derivative, a 2-(4-chloro-2-fluoro-5-(2-oxo-2-phenylethoxy)phenyl)-3a,4,7,7a-tetrahydro-1H-isoindole-1,3(2H)-dione derivative, and a 1-(4-chloro-2-fluoro-5-(2-oxo-2-phenoxyethoxy)phenyl)-3-methylpyrrolidine-2,5-dione derivative.

In some embodiments, the 2-(4-chloro-2-fluoro-5-(2-oxo-2-phenylethoxy)phenyl)-4,5,6,7-tetrahydro-1H-isoindole-1,3(2H)-dione derivative is prepared by a process including: at ambient temperature, dissolving 2-(4-chloro-2-fluoro-5-hydroxybenzene)-4,5,6,7-tetrahydro-1H-isoindole-1,3(2H)-dione in acetonitrile, adding potassium carbonate, and stirring for 30 min; adding an α-bromo(chloro)acetophenone derivative, and conducting a reaction under reflux to obtain a reaction solution; filtering the reaction solution to remove potassium carbonate and obtain a filtered solution, extracting the filtered solution to obtain an organic phase, and subjecting the organic phase to drying with anhydrous sodium sulfate, concentration, and purification with silica gel chromatography to obtain a target compound, namely the 2-(4-chloro-2-fluoro-5-(2-oxo-2-phenylethoxy)phenyl)-4,5,6,7-tetrahydro-1H-isoindole-1,3(2H)-dione derivative. A reaction equation is as follows:

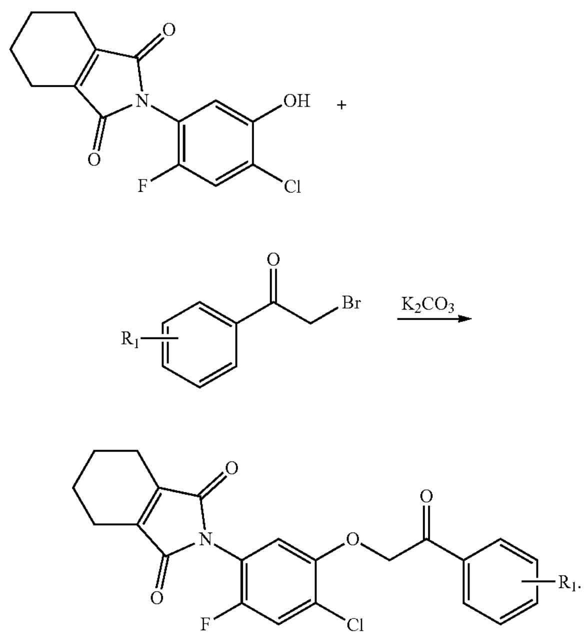

In some embodiments, the 2-(4-chloro-2-fluoro-5-(2-oxo-2-phenylethoxy)phenyl)isoindoline-1,3-dione derivative is prepared by a process including: at ambient temperature, dissolving 2-(4-chloro-2-fluoro-5-hydroxyphenyl)isoindole-1,3-dione in acetonitrile, adding potassium carbonate, and stirring for 30 min; adding an α-bromo(chloro)acetophenone derivative, and conducting a reaction under reflux to obtain a reaction solution; filtering the reaction solution to remove potassium carbonate and obtain a filtered solution, extracting the filtered solution to obtain an organic phase, subjecting the organic phase to drying with anhydrous sodium sulfate, concentration, and purification with silica gel chromatography to obtain a target compound, namely the 2-(4-chloro-2-fluoro-5-(2-oxo-2-phenylethoxy)phenyl) isoindoline-1,3-dione derivative. A reaction equation is as follows:

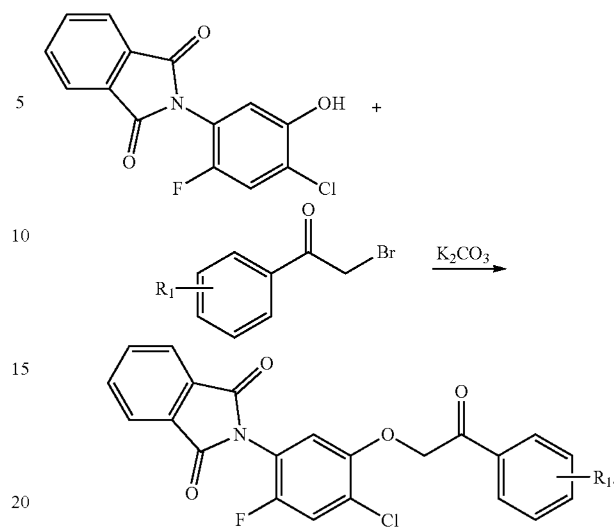

In some embodiments, the 2-(4-chloro-2-fluoro-5-(2-oxo-2-phenylethoxy)phenyl)-3a,4,7,7a-tetrahydro-1H-isoindole-1,3(2H)-dione derivative is prepared by a process including: at ambient temperature, dissolving 2-(4-chloro-2-fluoro-5-hydroxyphenyl)-3a,4,7,7a-tetrahydro-1H-isoindole-1,3(2H)-dione in acetonitrile, adding potassium carbonate, and stirring for 30 min; adding an α-bromo(chloro)acetophenone derivative, and conducting a reaction under reflux to obtain a reaction solution; filtering the reaction solution to remove potassium carbonate and obtain a filtered solution, extracting the filtered solution to obtain an organic phase, and subjecting the organic phase to drying with anhydrous sodium sulfate, concentration, and purification with silica gel chromatography to obtain a target compound, namely the 2-(4-chloro-2-fluoro-5-(2-oxo-2-phenylethoxy)phenyl)-3a,4,7,7a-tetrahydro-1H-isoindole-1,3(2H)-dione derivative. A reaction equation is as follows:

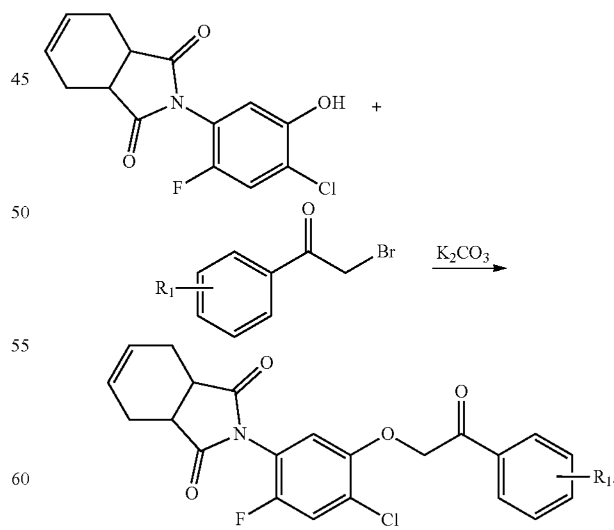

In some embodiments, the 1-(4-chloro-2-fluoro-5-(2-oxo-2-phenoxyethoxy)phenyl)-3-methylpyrrolidine-2,5-dione derivative is prepared by a process including: at ambient temperature, dissolving 1-(4-chloro-2-fluoro-5-hydroxyphenyl)-3-methylpyrrolidine-2,5-dione in acetonitrile, adding potassium carbonate, and stirring for 30 min; adding an α-bromo(chloro)acetophenone derivative, and conducting a reaction under reflux to obtain a reaction solution; filtering the reaction solution to remove potassium carbonate and obtain a filtered solution, extracting the filtered solution to obtain an organic phase, subjecting the organic phase to drying with anhydrous sodium sulfate, concentration, and purification with silica gel chromatography to obtain a target compound, namely the 1-(4-chloro-2-fluoro-5-(2-oxo-2-phenoxyethoxy)phenyl)-3-methylpyrrolidine-2,5-dione derivative. A reaction equation is as follows:

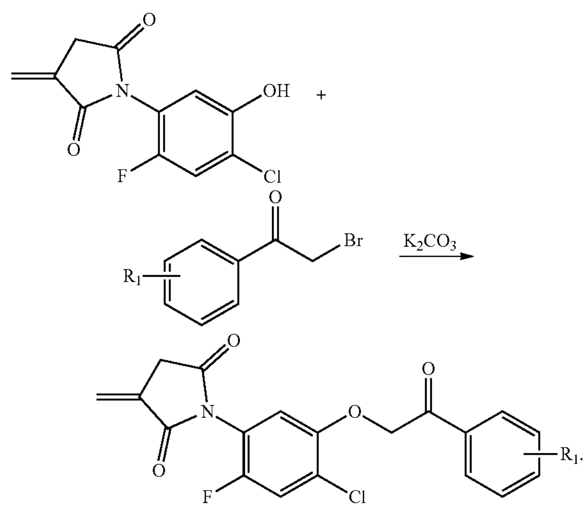

In some embodiments, under a condition that A in formula 3 is —NH—, a compound represented by formula 9, an organic alkali, the compound represented by formula 8, and an organic solvent III-2 are mixed to obtain a mixture III-2, and the mixture III-2 is subjected to nucleophilic substitution to obtain the N-phenylimine amide (ester) derivative represented by formula 3; wherein formula 9

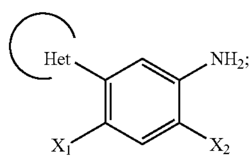

X—$R_5$ formula 8; in formula 8, X is selected from the group consisting of Cl and Br.

In some embodiments, the compound represented by formula 9 is prepared by a process including the following steps:

mixing a compound represented by formula 19, concentrated sulfuric acid (80 wt %), and concentrated nitric acid (65 wt %) to obtain a mixture IX-1, and subjecting the mixture IX-1 to nitration to obtain a compound represented by formula 20; and mixing the compound represented by formula 20 with an ethanol-aqueous solvent, ammonium chloride, and an iron powder to obtain a mixture IX-2, and subjecting the mixture IX-2 to reduction to obtain the compound represented by formula 9;

formula 19

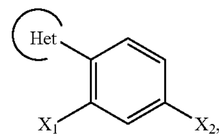

formula 20

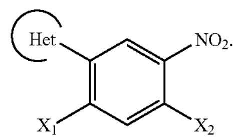

In some embodiments, the compound represented by formula 9 is specifically a compound represented by formula 9-1.

formula 9-1

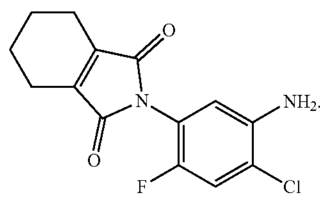

In the present disclosure, the compound represented by formula 9-1 has a chemical name of 2-(5-amino-4-chloro-2-fluorophenyl)-4,5,6,7-tetrahydro-1H-isoindole-1,3(2H)-dione.

In some embodiments, the compound represented by formula 9-1 is prepared by a process including the following steps:

(1) dissolving 4-chloro-2-fluoroaniline in glacial acetic acid, adding 4,5,6,7-tetrahydroisobenzofuran-1,3-dione under stirring, and conducting reaction under reflux by heating; and after the reaction is completed, pouring a resulting system into ice water and stirring continuously, such that a large amount of solids are precipitated; conducting suction filtration to obtain a first filter cake, washing the first filter cake three times with a saturated sodium bicarbonate solution, and drying the washed first filter cake for subsequent use; wherein a reaction equation is as follows:

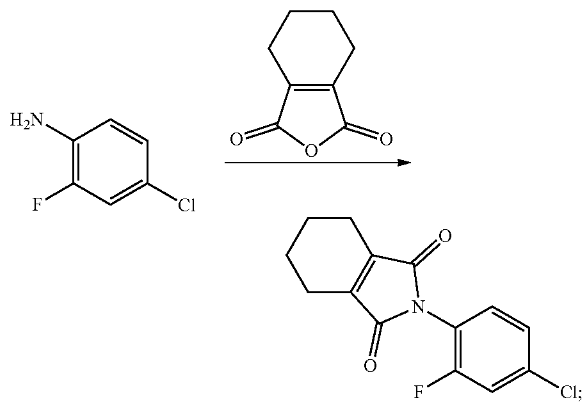

(2) dissolving 2-(4-chloro-2-fluorophenyl)-4,5,6,7-tetrahydro-1H-isoindole-1,3(2H)-dione in 80 wt % sulfuric acid, slowly adding concentrated nitric acid dropwise at −15° C. thereto, and holding at −15° C. and then subjecting to reaction; after the reaction is completed, pouring a resulting system into ice water and stirring continuously, such that a large amount of yellow solids are precipitated; and conducting suction filtration to obtain a second filter cake, washing the second filter cake three times with a saturated sodium bicarbonate solution, and drying the washed second filter cake for subsequent use; wherein a reaction equation is as follows:

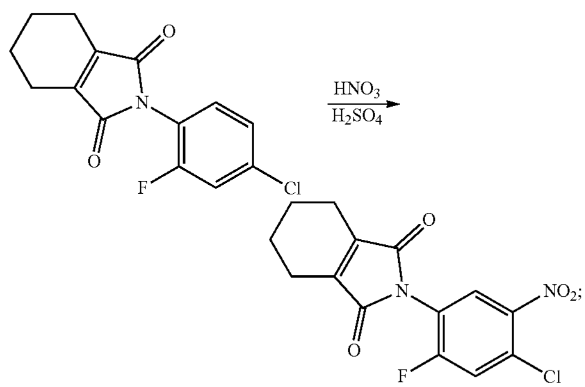

(3) dissolving 2-(4-chloro-2-fluoro-5-nitrophenyl)-4,5,6,7-tetrahydro-1H-isoindole-1,3(2H)-dione in 90 vol % ethanol, adding ammonium chloride, stirring, and conducting reaction under reflux by heating; slowly adding the iron powder and continuing the reaction under reflux; after the reaction is completed, conducting suction filtration to obtain a filtrate, and subjecting the filtrate to concentration and recrystallization the solid to obtain a compound, namely the 2-(5-amino-4-chloro-2-fluorophenyl)-4,5,6,7-tetrahydro-1H-isoindole-1,3(2H)-dione; wherein a reaction equation is:

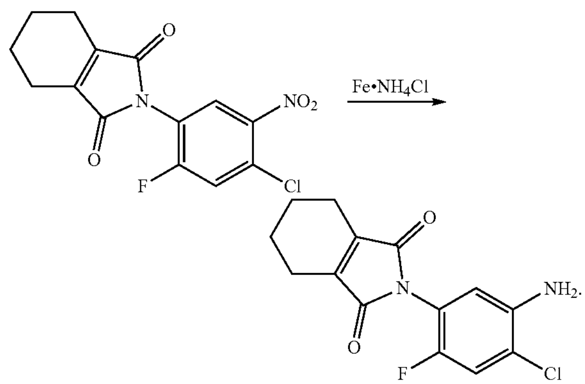

In some embodiments, under a condition that A in formula 3 is —NH—, the N-phenylimine amide (ester) derivative represented by formula 3 is an N-(2-chloro-5-(1,3-dioxo-1,3,4,5,6,7-hexahydro-2H-isoindole-2-yl)-4-fluorophenyl) amide derivative.

In some embodiments, the N-(2-chloro-5-(1,3-dioxo-1,3,4,5,6,7-hexahydro-2H-isoindole-2-yl)-4-fluorophenyl) amide derivative is prepared by a process including: adding different acyl chlorides into 2-(5-amino-4-chloro-2-fluorophenyl)-4,5,6,7-tetrahydro-1H-isoindole-1,3(2H)-dione in dichloromethane under ice bath, and then conducting a reaction with triethylamine as a catalyst at ambient temperature under stirring; and after the reaction is completed, extracting an obtained reaction solution with ethyl acetate to obtain an organic phase, drying the organic phase with anhydrous sodium sulfate, and purifying with silica gel chromatography. A reaction equation is as follows:

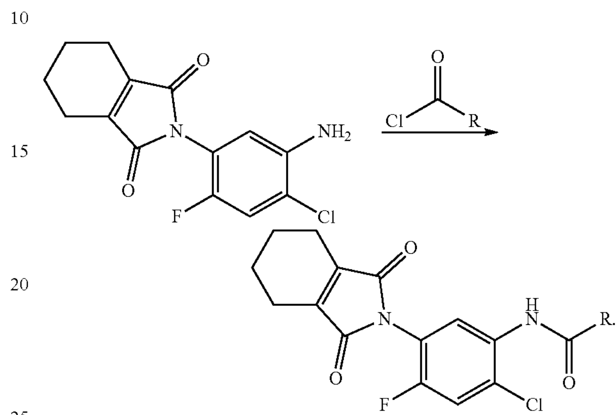

In the present disclosure, a compound represented by formula 10, an organic solvent V, and a compound containing Het are mixed, and nucleophilic substitution is conducted to obtain the N-phenylimine benzoate derivative represented by formula 4.

In the present disclosure, the compound represented by formula 10 is prepared by a process including the following steps:

(1) dissolving 2-chloro-4-fluoro-5-nitrobenzoic acid in dimethylformamide (DMF), adding potassium carbonate and stirring at ambient temperature for 10 min, and adding different chloro(bromo)acetate derivatives to conduct reaction; after the reaction is completed, subjecting an obtained reaction solution to suction filtration to remove potassium carbonate, followed by extraction with ethyl acetate, concentration, and purification with silica gel column chromatography to obtain a 2-chloro-4-fluoro-5-nitrobenzoate derivative; wherein a reaction equation is as follows:

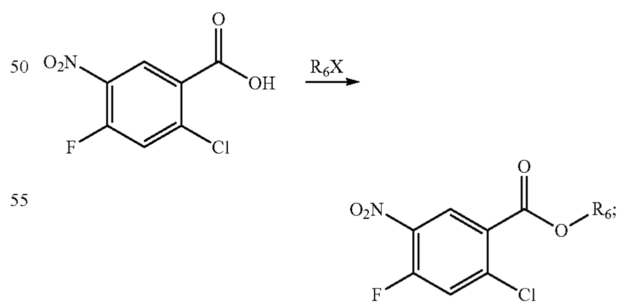

(2) dissolving the 2-chloro-4-fluoro-5-nitrobenzoate derivative in 90 vol % ethanol, adding ammonium chloride, stirring, and conducting reaction under reflux by heating; slowly adding an iron powder and continuing the reflux reaction; after the reaction is completed, conducting suction filtration to obtain a filtrate, and subjecting the filtrate to concentration to obtain a solid, and recrystallizing the solid to obtain a compound, namely the 5-amino-2-chloro-4-fluorobenzoate derivative; where a reaction equation is:

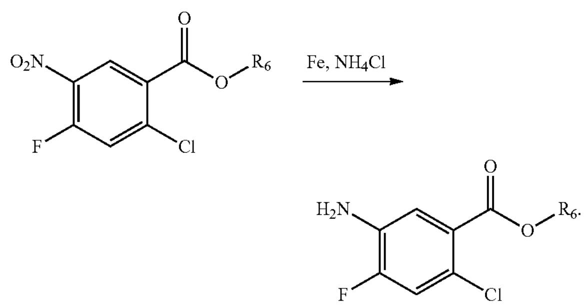

In some embodiments, the compound containing Het is

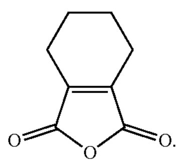 [SMILES: O=C1OC(=O)C2=C1CCCC2]

In some embodiments, the N-phenylimine benzoate derivative represented by formula 4 is a 2-chloro-5-(1,3-dioxo-1,3,4,5,6,7-hexahydro-2H-isoindole-2-yl)-4-fluorobenzoate derivative.

In some the embodiments, 2-chloro-5-(1,3-dioxo-1,3,4,5,6,7-hexahydro-2H-isoindole-2-yl)-4-fluorobenzoate derivative is prepared by a process including: dissolving a 5-amino-2-chloro-4-fluorobenzoate derivative in glacial acetic acid, adding 4,5,6,7-tetrahydroisobenzofuran-1,3-dione, and conducting reaction under reflux by heating; after the reaction is completed, extracting an obtained reaction solution with ethyl acetate, followed by drying, concentration, and purification with silica gel column chromatography to obtain a target compound. A reaction equation is as follows:

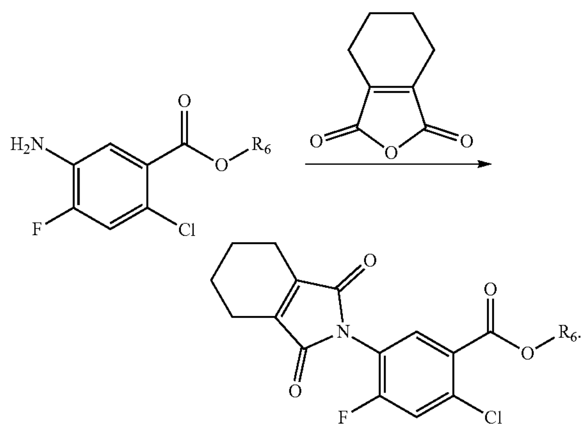

The present disclosure further provides use of the N-phenylimine derivative or an N-phenylimine derivative prepared by the method as an active ingredient of a herbicide.

In some embodiments, the herbicide includes a post-emergence herbicide for gramineous weeds and/or a post-emergence herbicide for broad-leaf weeds.

In the present disclosure, based on a structure of N-phenylphthalimides, differently substituted "imines" are used as pharmacophores to create N-phenylimine herbicides with relatively stable physical and chemical properties. At a dosage of 10 a.i.g/mu, this herbicide has a post-emergence inhibition rate of 28% to 50% on *Echinochloa crusgalli*, a post-emergence inhibition rate of 34% to 56% on *Digitaria sanguinalis*, a post-emergence inhibition rate of 50% to 70% on *Setaria viridis*, a post-emergence inhibition rate of 100% on *Abutilon theophrasti*, a post-emergence inhibition rate of 100% on *Portulaca oleracea*, and a post-emergence inhibition rate of 100% on *Amaranthus retroflexus*. In contrast, a control drug, flumioxazin, at 10 a.i.g/mu, has a post-emergence inhibition rate of 40% to 90% against gramineous weeds, and a control effect of 100% against broad-leaf weeds. The N-phenylimine compounds have a poor control effect on gramineous weeds, but have an excellent control effect on broad-leaf weeds. Among them, some compounds have a control effect of 100% on *Abutilon theophrasti, Amaranthus retroflexus*, and *Portulaca oleracea* at 2.5 a.i.g/mu.

In the present disclosure, it is proved by experiments that the N-phenylimine derivative has an excellent effect on inhibiting the growth of weeds, and has a simple structure, a simple preparation process, a low production cost, and broad application prospects.

In order to further illustrate the present disclosure, the technical solutions provided by the present disclosure are described in detail below in connection with examples, but these examples should not be understood as limiting the claimed scope of the present disclosure.

Example 1: A Preparation Method of 2-(5-((5-(5-bromo-2-tolyl)-1,2,4-oxadiazole-3-yl)methoxy)-4-chloro-2-fluorophenyl)-4,5,6,7-tetrahydro-1H-isoindole-1,3(2H)-dione (Corresponding to Compound A1) was Performed According to the Following Procedures

(1) Preparation of (Z)-5-bromo-N'-hydroxy-2-methylbenzimidamine: a Reaction Equation was as Follows

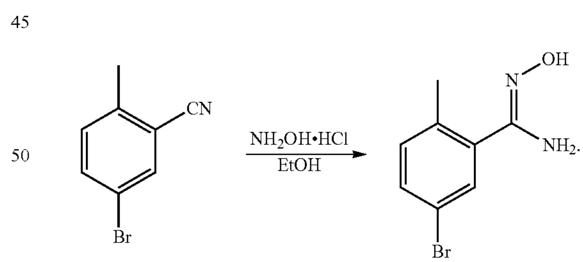

5-bromo-2-methylbenzonitrile (5 g, 25.50 mM) was mixed with 50 mL of absolute ethanol in a 100 mL three-necked flask, and added with $NH_2OH \cdot HCl$ (5.47 g, 76.51 mM) in ice bath. The pH of an obtained system was adjusted to neutral with 1 M of NaOH to obtain a neutral system, the ice bath was removed, and the neutral system was heated to 90° C. and subjected to a reaction at 90° C. for 4 h under reflux. After the reaction was completed, an obtained reaction solution was distilled under reduced pressure, and cooled, such that a solid was precipitated, and the solid was recrystallized with absolute ethanol to obtain a solid product (5.02 g, 86%).

(2) Preparation of 3-(5-bromo-2-methylphenyl)-5-(chloromethyl)-1,2,4-oxadiazole: a Reaction Equation was as Follows

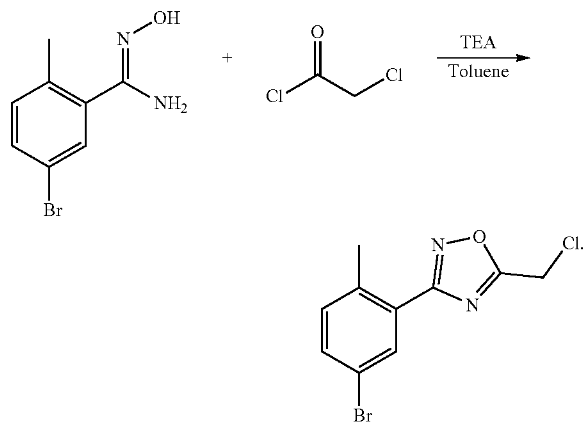

The (Z)-5-bromo-N'-hydroxy-2-methylbenzimidamine solid (5 g, 21.83 mM) was dissolved in 30 mL of toluene, and chloroacetyl chloride (4.93 g, 43.65 mM) and triethylamine (2.21 g, 21.83 mM) were added thereto to obtain a mixture, and the mixture was then heated to 110° C. and subjected to reaction at 110° C. under reflux. After the reaction is completed, the obtained reaction solution was directly extracted with ethyl acetate (60 mL) to obtain an organic phase, and the organic phase was dried with anhydrous sodium sulfate, concentrated, and purified with silica gel column chromatography to obtain a solid (4.96 g, 79%). The compound was characterized by: $^1$H NMR (500 MHz, $CDCl_3$) δ 7.7 (d, J=2.5 Hz, 1H), 7.4 (dd, J=7.3, 2.6 Hz, 1H), 7.4-7.3 (m, 1H), 5.0 (s, 2H), 2.5 (d, J=1.0 Hz, 3H).

(3) Preparation of 4-chloro-2-fluoro-5-aminophenol: a Reaction Equation was as Follows

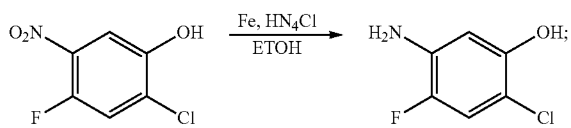

4-chloro-2-fluoro-5-nitrophenol (10 g, 52.21 mM) was dissolved in 100 mL of 90 vol % ethanol in a 250 mL three-necked round-bottom flask, $NH_4Cl$ (8.75 g, 156.62 mM) was added under stirring, and a resulting solution was heated to 90° C. and then subjected to reaction. When an obtained reaction system was refluxed, an Fe powder (8.38 g, 156.62 mM) was added in batches, and the reflux was continued for 3 h. After the reaction was completed, an obtained reaction solution was subjected to suction filtration while hot to obtain a filter cake, the filter cake was washed three times with hot ethanol, and an obtained filtrate was concentrated, such that a large amount of dark brown solid was precipitated, and then the solid was recrystallized with ethanol to obtain the 4-chloro-2-fluoro-5-aminophenol (7.76 g, 92%).

(4) Preparation of 2-(4-chloro-2-fluoro-5-hydroxybenzene)-4,5,6,7-tetrahydro-1H-isoindole-1,3(2H)-dione: a Reaction Equation was as Follows

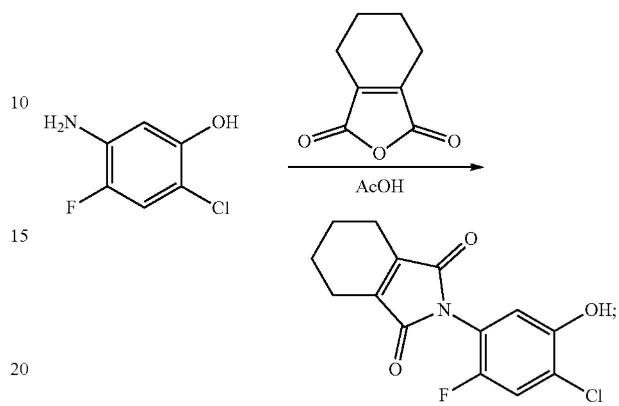

4-chloro-2-fluoro-5-aminophenol (7 g, 43.33 mM) was mixed with 50 mL of glacial acetic acid in a 100 mL three-necked round-bottom flask, 4,5,6,7-tetrahydroisobenzofuran-1,3-dione (7.25 g, 47.66 mM) was added, and a resulting system was heated to 100° C. and then subjected to reaction. After the reaction was completed, a resulting reaction system was poured into ice water, such that a large amount of milky white solid was precipitated, and then a resulting mixture was subjected to suction filtration to obtain an gray white solid (11.40 g, 89%). The compound was characterized by: $^1$H NMR (400 MHz, DMSO-$d_6$) δ 10.4 (s, 1H), 7.6 (d, J=2.6 Hz, 1H), 7.3 (d, J=2.6 Hz, 1H), 2.3 (d, J=3.2 Hz, 4H), 1.7 (p, J=2.9 Hz, 4H).

(5) Preparation of 2-(5-((3-(5-bromo-2-tolyl)-1,2,4-oxadiazole-5-yl)methoxy)-4-chloro-2-fluorophenyl)-4,5,6,7-tetrahydro-1H-isoindole-1,3(2H)-dione: a Reaction Equation was as Follows

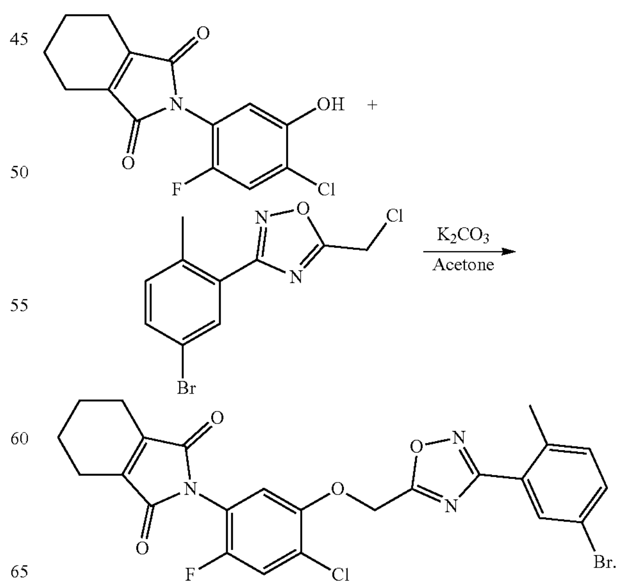

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min. 3-(5-bromo-2-tolyl)-5-(chloromethyl)-1,2,4-oxadiazole (0.29 g, 1.01 mM) was added, and a resulting mixture was heated to 60° C. and then subjected to reaction under reflux. After the reaction was completed, a resulting reaction solution was filtered to remove potassium carbonate, extracted to obtain an organic phase, and the organic phase was dried with anhydrous sodium sulfate, concentrated, and purified with silica gel chromatography to obtain a target compound (0.44 g, 88%).

Example 2: A Preparation Method of 2-(4-chloro-2-fluoro-5-((3-(2-tolyl)-1,2,4-oxadiazole-5-yl)methoxy)phenyl)-4,5,6,7-tetrahydro-1H-isoindole-1,3(2H)-dione (Corresponding to Compound A2) was Performed According to the Following Procedures: a Reaction Equation was as Follows

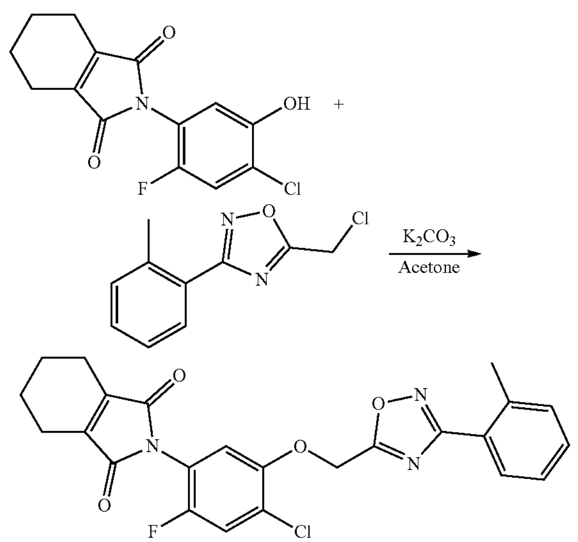

Steps (1) to (4) were the same as those in Example 1.

(5) Preparation of 2-(4-chloro-2-fluoro-5-((3-(2-tolyl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was and added stirred for 30 min, 3-(2-tolyl)-5-(chloromethyl)-1,2,4-oxadiazole (0.21 g, 1.01 mM) was added, and a resulting mixture was heated to 60° C. and then subjected to reaction under reflux. After the reaction was completed, a resulting reaction solution was filtered to remove potassium carbonate, extracted to obtain an organic phase, and the organic phase was dried with anhydrous sodium sulfate, concentrated, and purified with silica gel chromatography to obtain a target compound (0.37 g, 80%).

Example 3: A Preparation Method of 2-(4-chloro-5-(3-(3-chlorophenyl)-1,2,4-oxadiazole-5-yl)methoxy)-2-fluorophenyl)-4,5,6,7-tetrahydro-1H-isoindole-1,3(2H)-dione (Corresponding to Compound A3) was Performed According to the Following Procedures: a Reaction Equation was as Follows

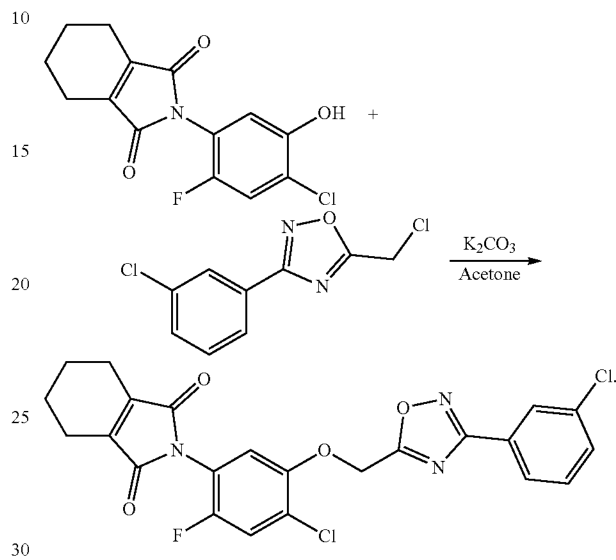

Steps (1) to (4) were the same as those in Example 1.

(5) Preparation of 2-(4-chloro-5-(3-(3-chlorophenyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(3-chlorophenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified by silica gel chromatography to obtain a target compound (0.40 g, 81%).

Example 4: A Preparation Method of 2-(5-(3-(2-bromophenyl)-1,2,4-oxadiazole-5-yl)methoxy)-4-chloro-2-fluorophenyl)-4,5,6,7-tetrahydro-1H-isoindole-1,3(2H)-dione (Corresponding to Compound A4) was Performed According to the Following Procedures: a Reaction Equation was as Follows

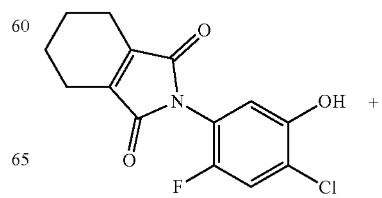

-continued

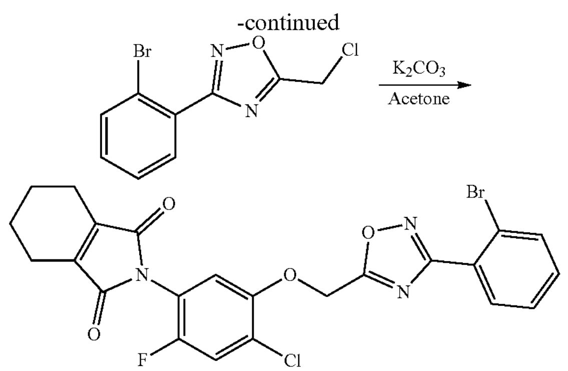

Steps (1) to (4) were the same as those in Example 1.

(5) Preparation of 2-(5-(3-(2-bromophenyl)-1,2,4-oxadiazole-5-yl)methoxy)-4-chloro-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 3-(2-bromophenyl)-5-(chloromethyl)-1,2,4-oxadiazole (0.28 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified by silica gel chromatography to obtain a target compound (0.44 g, 88%).

Example 5: A Preparation Method of 2-(4-chloro-5-(3-(4-chlorophenyl)-1,2,4-oxadiazole-5-yl)methoxy)-2-fluorophenyl)-4,5,6,7-tetrahydro-1H-isoindole-1,3(2H)-dione (Corresponding to Compound A5) was Performed According to the Following Procedures: a Reaction Equation was as Follows

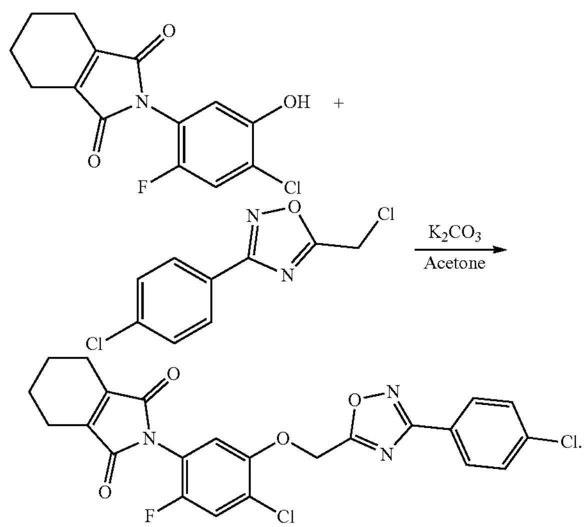

Steps (1) to (4) were the same as those in Example 1.

(5) Preparation of 2-(4-chloro-5-(3-(4-chlorophenyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(4-chlorophenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.40 g, 80%).

Example 6: A Preparation Method of 2-(4-chloro-5-(3-(2,4-difluorophenyl)-1,2,4-oxadiazole-5-yl) methoxy)-2-fluorophenyl)-4,5,6,7-tetrahydro-1H-isoindole-1,3(2H)-dione (Corresponding to Compound A6) was Performed According to the Following Procedures: a Reaction Equation was as Follows

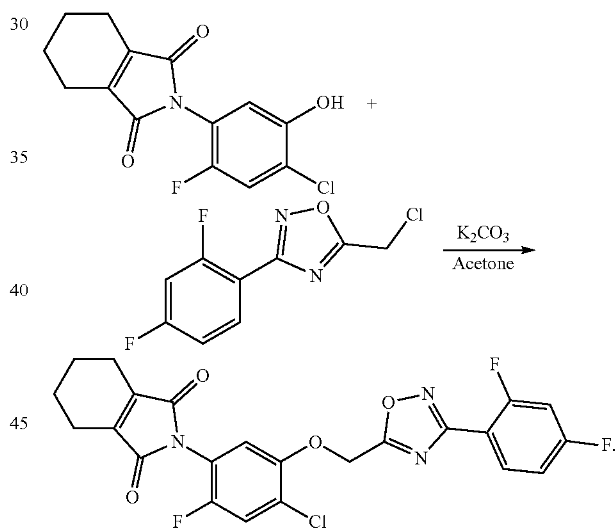

Steps (1) to (4) were the same as those in Example 1.

(5) Preparation of 2-(4-chloro-5-(3-(2,4-difluorophenyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2,4-difluorophenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.38 g, 76%).

Example 7: A Preparation Method of 2-(4-chloro-5-(3-(4-chloro-2-fluorophenyl)-1,2,4-oxadiazole-5-yl)methoxy)-2-fluorophenyl)-4,5,6,7-tetrahydro-1H-isoindole-1,3(2H)-dione (Corresponding to Compound A7) was Performed According to the Following Procedures: a Reaction Equation was as Follows

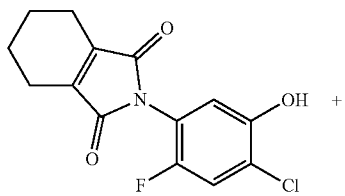

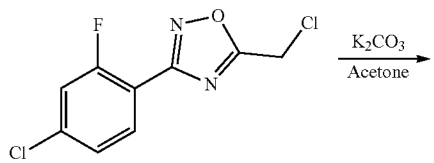

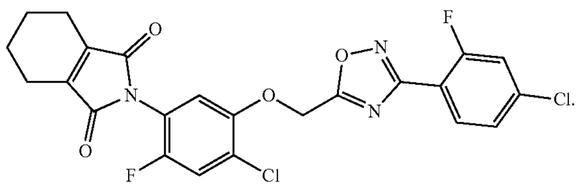

Steps (1) to (4) were the same as those in Example 1.

(5) Preparation of 2-(4-chloro-5-(3-(4-chloro-2-fluorophenyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 3-(4-chloro-2-fluorophenyl)-5-(chloromethyl)-1,2,4-oxadiazole (0.25 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.42 g, 88%).

Example 8: A Preparation Method of 2-(4-chloro-5-(3-(2-chlorophenyl)-1,2,4-oxadiazole-5-yl)methoxy)-2-fluorophenyl)-4,5,6,7-tetrahydro-1H-isoindole-1,3(2H)-dione (Corresponding to Compound A8) was Performed According to the Following Procedures: a Reaction Equation was as Follows

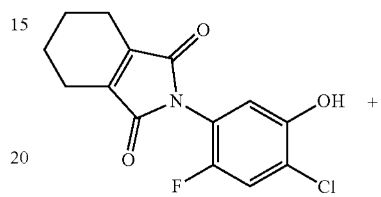

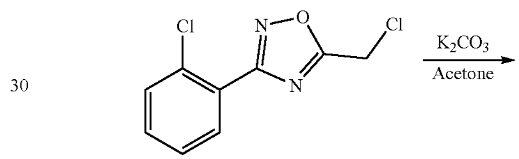

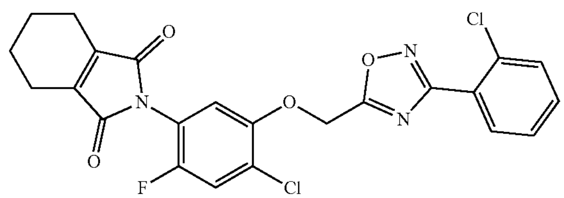

Steps (1) to (4) were the same as those in Example 1.

(5) Preparation of 2-(4-chloro-5-(3-(2-chlorophenyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2-chlorophenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.37 g, 75%).

Example 9: A Preparation Method of 2-(4-chloro-2-fluoro-5-(3-(2-fluoro-4-methylphenyl)-1,2,4-oxadiazole-5-yl)methoxy)phenyl)-4,5,6,7-tetrahydro-1H-isoindole-1,3(2H)-dione (Corresponding to Compound A9) was Performed According to the Following Procedures: a Reaction Equation was as Follows

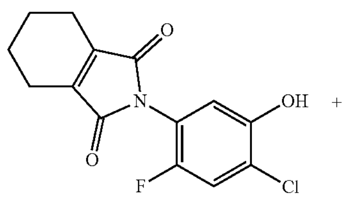

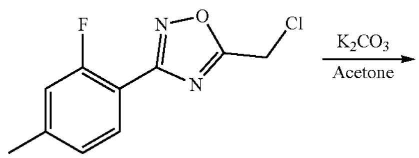

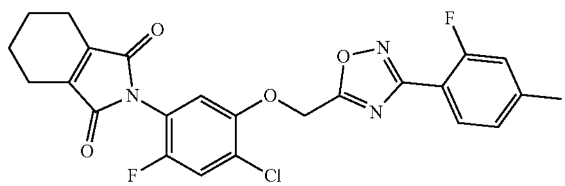

Steps (1) to (4) were the same as those in Example 1.

(5) Preparation of 2-(4-chloro-2-fluoro-5-(3-(2-fluoro-4-methylphenyl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added stirred and for 30 min, 5-(chloromethyl)-3-(2-fluoro-4-methylphenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.38 g, 78%).

Example 10: A Preparation Method of 2-(4-chloro-5-(3-(4-chloro-6-(trifluoromethyl)pyridin-3-yl)-1,2,4-oxadiazole-5-yl)methoxy)-2-fluorophenyl)-4,5,6,7-tetrahydro-1H-isoindole-1,3(2H)-dione (Corresponding to Compound A10) was Performed According to the Following Procedures: a Reaction Equation was as Follows

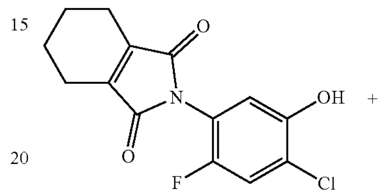

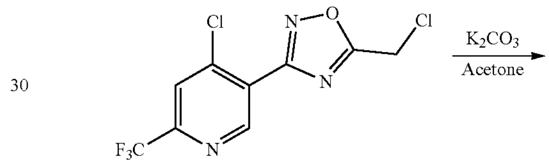

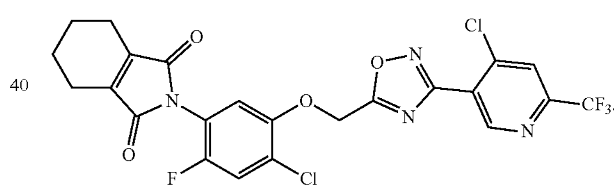

Steps (1) to (4) were the same as those in Example 1.

(5) Preparation of 2-(4-chloro-5-(3-(4-chloro-6-(trifluoromethyl)pyridin-3-yl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 3-(2-chloro-4-(trifluoromethyl)pyridyl)-5-(chloromethyl)-1,2,4-oxadiazole (0.30 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.45 g, 80%).

Example 11: A Preparation Method of 2-(4-chloro-5-(3-(2,4-dibromophenyl)-1,2,4-oxadiazole-5-yl)methoxy)-2-fluorophenyl)-4,5,6,7-tetrahydro-1H-isoindole-1,3(2H)-dione (Corresponding to Compound A11) was Performed According to the Following Procedures: a Reaction Equation was as Follows

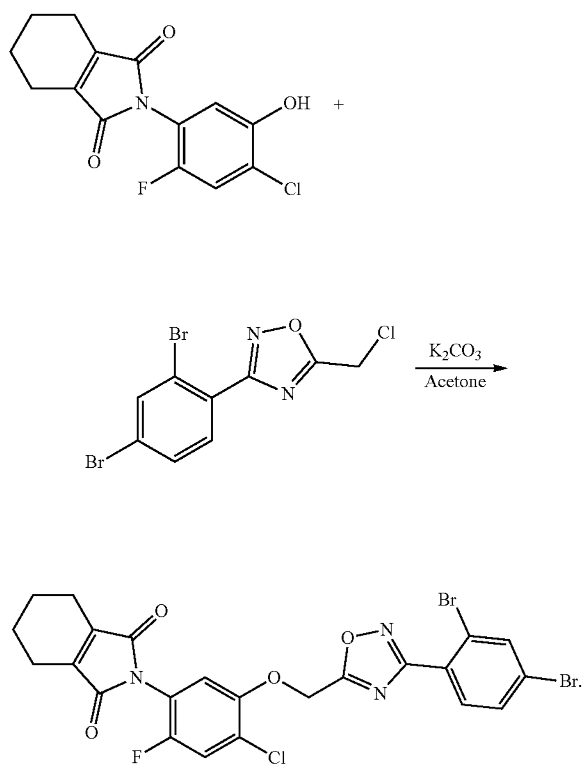

Steps (1) to (4) were the same as those in Example 1.

(5) Preparation of 2-(4-chloro-5-(3-(2,4-dibromophenyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2,4-dibromophenyl)-1,2,4-oxadiazole (0.36 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.42 g, 84%).

Example 12: A Preparation Method of 2-(4-chloro-2-fluoro-5-(3-(2-fluorophenyl)-1,2,4-oxadiazole-5-yl)methoxy)phenyl)-4,5,6,7-tetrahydro-1H-isoindole-1,3(2H)-dione (Corresponding to Compound A12) was Performed According to the Following Procedures: a Reaction Equation was as Follows

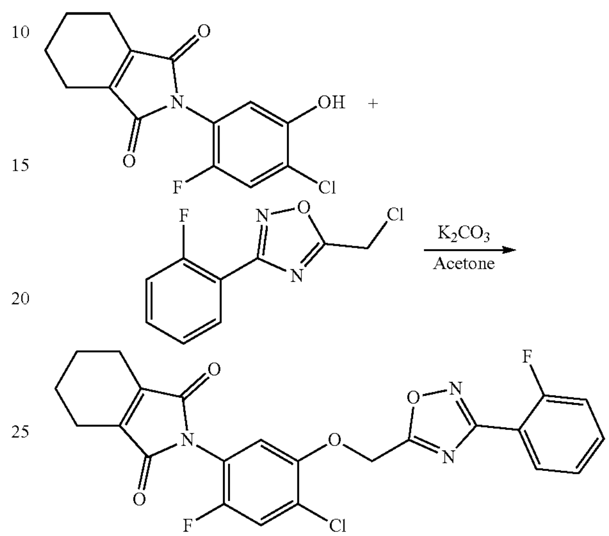

Steps (1) to (4) were the same as those in Example 1.

(5) Preparation of 2-(4-chloro-2-fluoro-5-(3-(2-fluorophenyl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2-fluorophenyl)-1,2,4-oxadiazole (0.20 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.41 g, 84%).

Example 13: A Preparation Method of 2-(3-(3-(3-(3-bromo-5-fluorophenyl)-1,2,4-oxadiazole-5-yl)methoxy)-4-chloro-2-fluorophenyl)-4,5,6,7-tetrahydro-1H-isoindole-1,3(2H)-dione (Corresponding to Compound A13) was Performed According to the Following Procedures: a Reaction Equation was as Follows

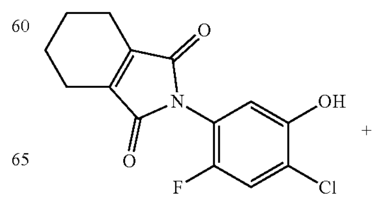

-continued

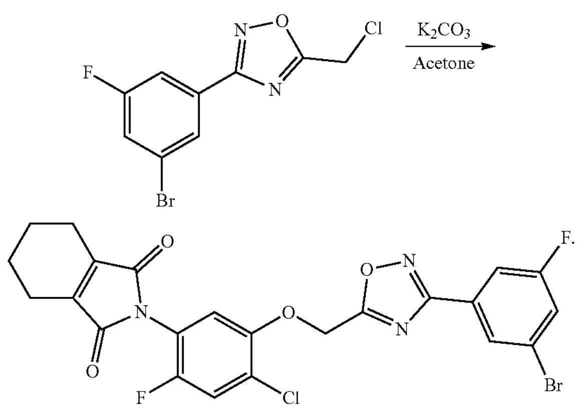

Steps (1) to (4) were the same as those in Example 1.

(5) Preparation of 2-(3-(3-(3-(3-bromo-5-fluorophenyl)-1,2,4-oxadiazole-5-yl)methoxy)-4-chloro-2-fluorophenyl)-4,5,6,7-tetrahydro-1H-isoindole-1,3 (2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 3-(3-bromo-5-fluorophenyl)-5-(chloromethyl)-1,2,4-oxadiazole (0.30 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.44 g, 88%).

Example 14: A Preparation Method of 2-(4-chloro-5-(3-(3,4-difluorophenyl)-1,2,4-oxadiazole-5-yl) methoxy)-2-fluorophenyl)-4,5,6,7-tetrahydro-1H-isoindole-1,3(2H)-dione (Corresponding to Compound A14) was Performed According to the Following Procedures: a Reaction Equation was as Follows

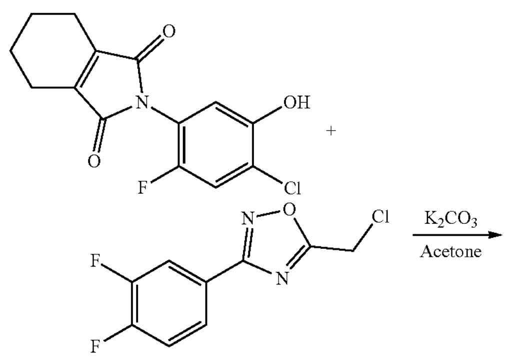

-continued

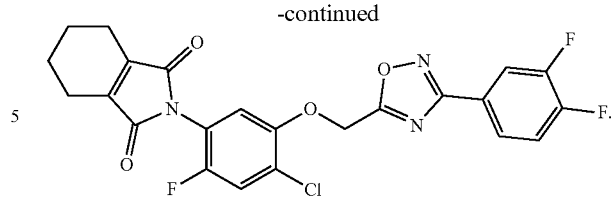

Steps (1) to (4) were the same as those in Example 1.

(5) Preparation of 2-(4-chloro-5-(3-(3,4-difluorophenyl)-1,2,4-oxadiazole-5-yl)methoxy)-2-fluorophenyl)-4,5,6,7-tetrahydro-1-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(3,4-difluorophenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.38 g, 78%).

Example 15: A Preparation Method of 2-(4-chloro-5-(3-(2-chloro-4-tolyl)-1,2,4-oxadiazole-5-yl) methoxy)-2-fluorophenyl)-4,5,6,7-tetrahydro-1H-isoindole-1,3(2H)-dione (Corresponding to Compound A15) was Performed According to the Following Procedures: a Reaction Equation was as Follows

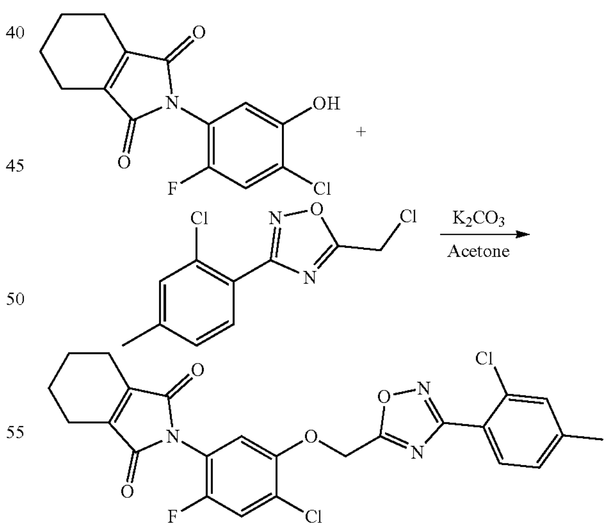

Steps (1) to (4) were the same as those in Example 1.

(5) Preparation of 2-(4-chloro-5-(3-(2-chloro-4-tolyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2-chloro-4-tolyl)-1,2,4-oxadiazole (0.25 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.44 g, 84%).

Example 16: A Preparation Method of 2-(4-chloro-5-(3-(2,6-dichloropyridin-3-yl)-1,2,4-oxadiazole-5-yl)methoxy)-2-fluorophenyl)-4,5,6,7-tetrahydro-1H-isoindole-1,3(2H)-dione (Corresponding to Compound A16) was Performed According to the Following Procedures: a Reaction Equation was as Follows

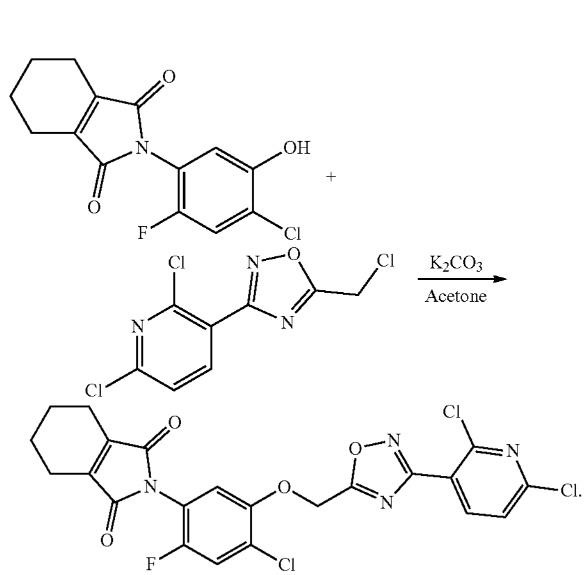

Steps (1) to (4) were the same as those in Example 1.

(5) Preparation of 2-(4-chloro-5-(3-(2,6-dichloropyridin-3-yl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2,6-dichloropyridin-3-yl)-1,2,4-oxadiazole (0.27 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.47 g, 90%).

Example 17: A Preparation Method of 2-(4-chloro-2-fluoro-5-(3-(3-(trifluoromethyl)phenyl)-1,2,4-oxadiazole-5-yl)methoxy)phenyl)-4,5,6,7-tetrahydro-1H-isoindole-1,3(2H)-dione (Corresponding to Compound A17) was Performed According to the Following Procedures: a Reaction Equation was as Follows

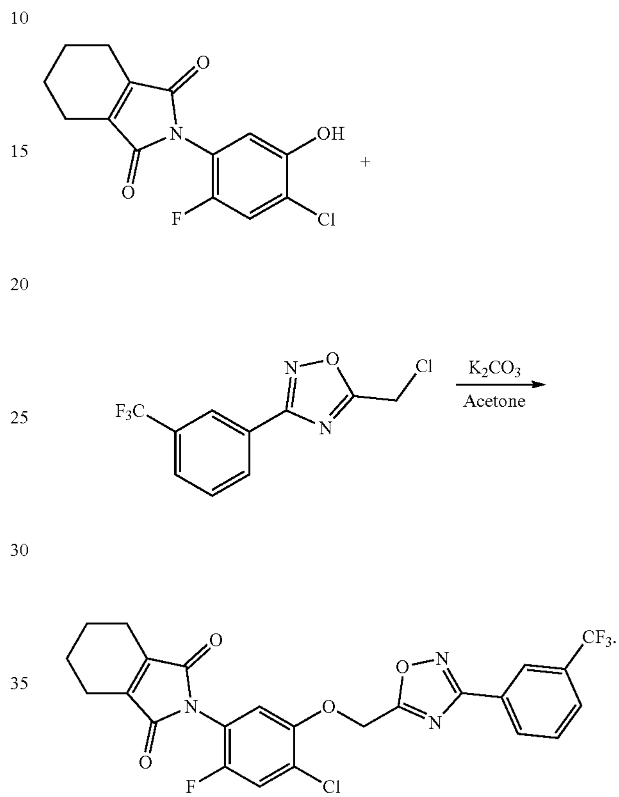

Steps (1) to (4) were the same as those in Example 1.

(5) Preparation of 2-(4-chloro-2-fluoro-5-(3-(3-(trifluoromethyl)phenyl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(3-(trifluoromethyl)phenyl)-1,2,4-oxadiazole (0.27 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried over anhydrous sodium sulfate, concentrated, and purified with silica gel chromatography to obtain a target compound (0.44 g, 89%).

Example 18: A Preparation Method of 2-(4-chloro-2-fluoro-5-(3-(2-(trifluoromethyl)phenyl)-1,2,4-oxadiazole-5-yl)methoxy)phenyl)-4,5,6,7-tetrahydro-1H-isoindole-1,3(2H)-dione (Corresponding to Compound A18) was Performed According to the Following Procedures: a Reaction Equation was as Follows

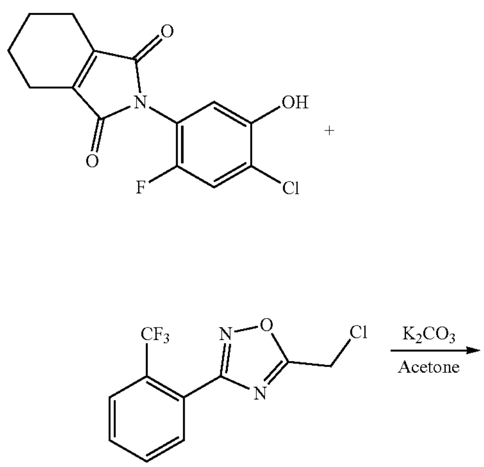

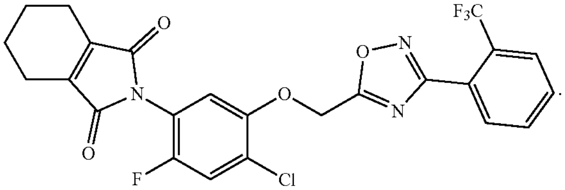

Steps (1) to (4) were the same as those in Example 1.

(5) Preparation of 2-(4-chloro-2-fluoro-5-(3-(2-(trifluoromethyl)phenyl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxy-benzene)-4,5,6,7-tetrahydro-1H-isoindole-1,3(2)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2-(trifluoromethyl)phenyl)-1,2,4-oxadiazole (0.27 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.46 g, 88%).

Example 19: A Preparation Method of 2-(4-chloro-2-fluoro-5-(3-(thiophen-2-yl)-1,2,4-oxadiazole-5-yl)methoxy)phenyl)-4,5,6,7-tetrahydro-1H-isoindole-1,3(2H)-dione (Corresponding to Compound A19) was Performed According to the Following Procedures: a Reaction Equation was as Follows

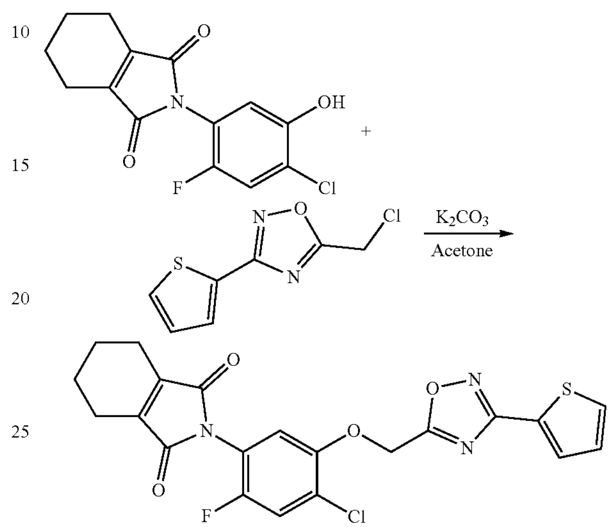

Steps (1) to (4) were the same as those in Example 1.

(5) Preparation of 2-(4-chloro-2-fluoro-5-(3-(thiophen-2-yl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(thiophen-2-yl)-1,2,4-oxadiazole (0.2 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.33 g, 85%).

Example 20: A Preparation Method of 2-(4-chloro-2-fluoro-5-(3-(4-(trifluoromethoxy)phenyl)-1,2,4-oxadiazole-5-yl)methoxy)phenyl)-4,5,6,7-tetrahydro-1H-isoindole-1,3(2H)-dione (Corresponding to Compound A20) was Performed According to the Following Procedures: a Reaction Equation was as Follows

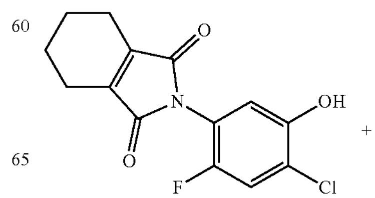

-continued

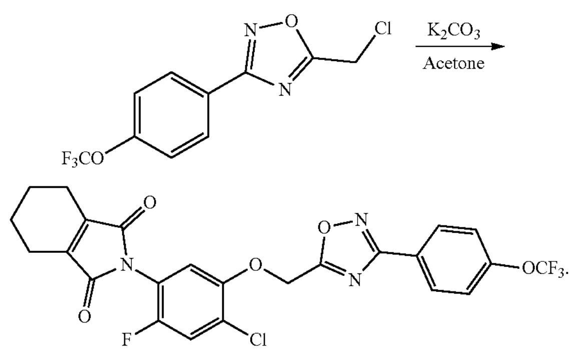

Steps (1) to (4) were the same as those in Example 1.

(5) Preparation of 2-(4-chloro-2-fluoro-5-(3-(4-(trifluoromethoxy)phenyl)-1,2,4-oxadiazole-5-yl) methoxy)phenyl)-4,5,6,7-tetrahydro-1H-isoindole-1, 3(2H)-dione At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(4-(trifluoromethoxy)phenyl)-1,2,4-oxadiazole (0.28 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.46 g, 88%).

Example 21: A Preparation Method of 2-(4-chloro-5-(3-(2-chloro-5-fluorophenyl)-1,2,4-oxadiazole-5-yl)methoxy)-2-fluorophenyl)-4,5,6,7-tetrahydro-1H-isoindole-1,3(2H)-dione (Corresponding to Compound A21) was Performed According to the Following Procedures: a Reaction Equation was as Follows

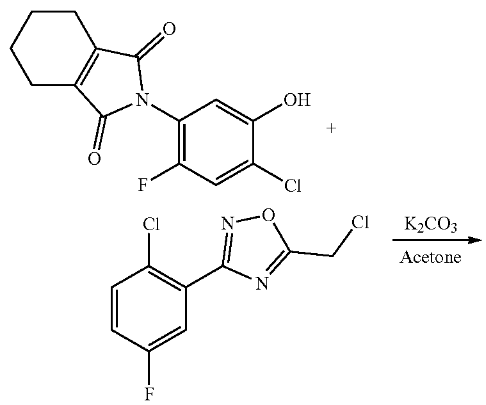

-continued

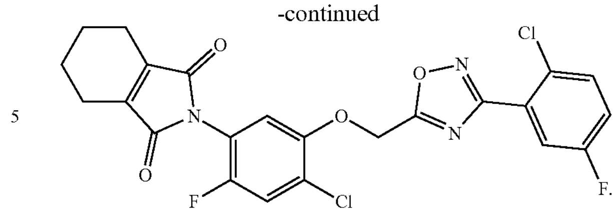

Steps (1) to (4) were the same as those in Example 1.

(5) Preparation of 2-(4-chloro-5-(3-(2-chloro-5-fluorophenyl)-1,2,4-oxadiazole-5-yl)methoxy)-2-fluorophenyl)-4,5,6,7-tetrahydro-1H-isoindole-1,3 (2H)-dione At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 3-(2-chloro-5-fluorophenyl)-5-(chloromethyl)-1,2,4-oxadiazole (0.25 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.39 g, 78%).

Example 22: A Preparation Method of 2-(4-chloro-2-fluoro-5-(3-(furan-2-yl)-1,2,4-oxadiazole-5-yl) methoxy)phenyl)-4,5,6,7-tetrahydro-1H-isoindole-1, 3(2H)-dione (Corresponding to Compound A22) was Performed According to the Following Procedures: a Reaction Equation was as Follows

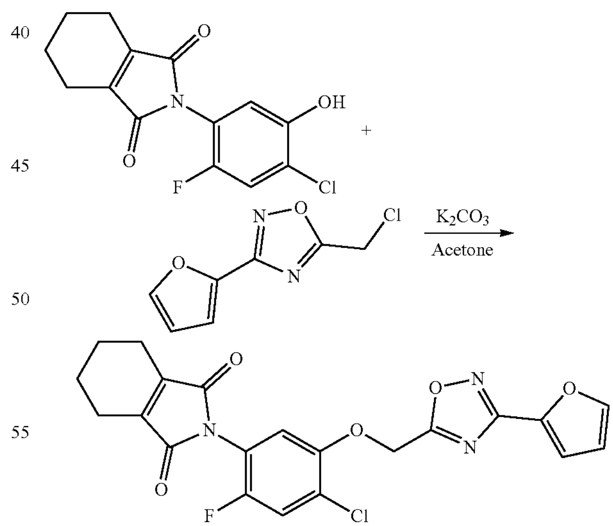

Steps (1) to (4) were the same as those in Example 1.

(5) Preparation of 2-(4-chloro-2-fluoro-5-(3-(furan-2-yl)-1,2,4-oxadiazole-5-yl)methoxy)phenyl)-4,5,6, 7-tetrahydro-1H-isoindole-1,3(2H)-dione At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(furan-2-yl)-1,2,4-oxadiazole (0.19 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.43 g, 88%).

Example 23: A Preparation Method of 2-(4-chloro-2-fluoro-5-(3-(4-fluoro-2-methylphenyl)-1,2,4-oxadiazole-5-yl)methoxy)phenyl)-4,5,6,7-tetrahydro-1H-isoindole-1,3(2H)-dione (Corresponding to Compound A23) was Performed According to the Following Procedures: a Reaction Equation was as Follows

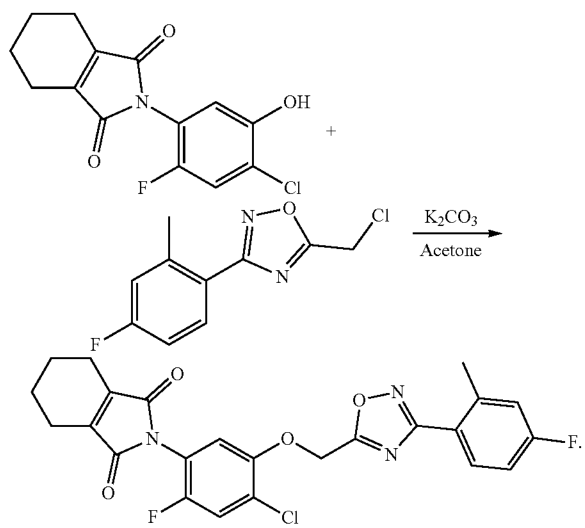

Steps (1) to (4) were the same as those in Example 1.

(5) Preparation of 2-(4-chloro-2-fluoro-5-(3-(4-fluoro-2-methylphenyl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(4-fluoro-2-methylphenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.39 g, 79%).

Example 24: A Preparation Method of 2-(4-chloro-5-(3-(2,6-difluorophenyl)-1,2,4-oxadiazole-5-yl)methoxy)-2-fluorophenyl)-4,5,6,7-tetrahydro-1H-isoindole-1,3(2H)-dione (Corresponding to Compound A24) was Performed According to the Following Procedures

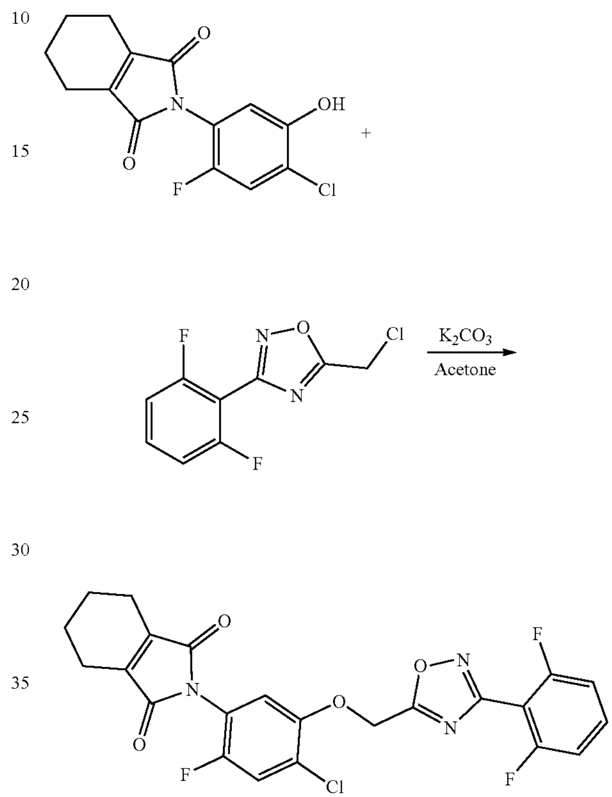

Steps (1) to (4) were the same as those in Example 1.

(5) Preparation of 2-(4-chloro-5-(3-(2,6-difluorophenyl)-1,2,4-oxadiazole-5-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(2,6-difluorophenyl)-1,2,4-oxadiazole (0.23 g, 1.01 mM) was added, and a resulting mixture was heated to 60° C. and then subjected to reaction under reflux. After the reaction was completed, a resulting reaction solution was filtered to remove potassium carbonate, an extracted to obtain an organic phase, and the organic phase was dried with anhydrous sodium sulfate, concentrated, and purified with silica gel chromatography to obtain a target compound (0.41 g, 83%).

Example 25: A Preparation Method of 2-(4-chloro-2-fluoro-5-(3-phenyl-1,2,4-oxadiazole-5-yl)methoxy)phenyl)-4,5,6,7-tetrahydro-1H-isoindole-1,3(2H)-dione (Corresponding to Compound A25) was Performed According to the Following Procedures: a Reaction Equation was as Follows

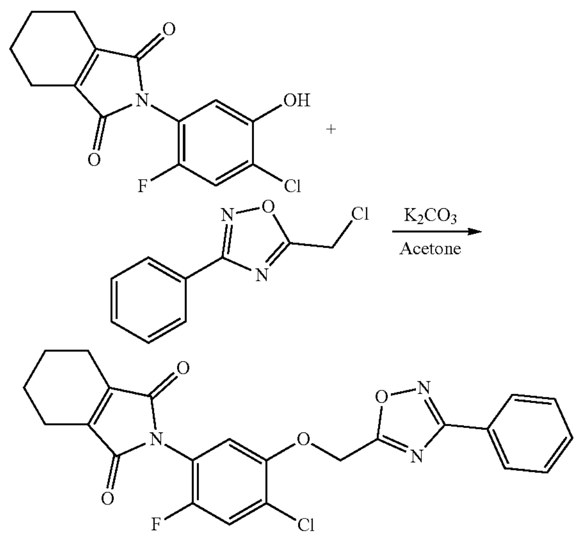

Steps (1) to (4) were the same as those in Example 1.

(5) Preparation of 2-(4-chloro-2-fluoro-5-(3-phenyl-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-phenyl-1,2,4-oxadiazole (0.20 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.40 g, 81%).

Example 26: A Preparation Method of 2-(5-(3-(4-(tert-butyl)phenyl)-1,2,4-oxadiazole-5-yl)methoxy)-4-chloro-2-fluorophenyl)-4,5,6,7-tetrahydro-1H-isoindole-1,3(2H)-dione (Corresponding to Compound A26) was Performed According to the Following Procedures: a Reaction Equation was as Follows

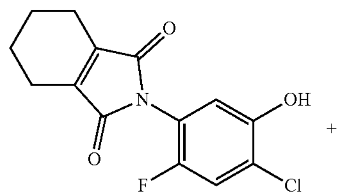

-continued

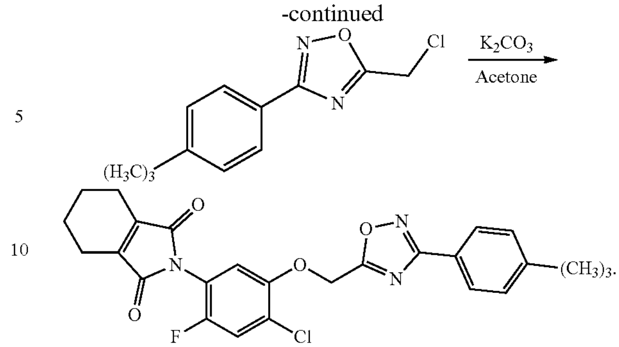

Steps (1) to (4) were the same as those in Example 1.

(5) Preparation of 2-(5-(3-(4-(tert-butyl)phenyl)-1,2,4-oxadiazole-5-yl)methoxy)-4-chloro-2-fluorophenyl)-4,5,6,7-tetrahydro-1H-isoindole-1,3(2H)-dione At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 3-(4-(tert-butyl)phenyl)-5-(chloromethyl)-1,2,4-oxadiazole (0.25 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.43 g, 87%).

Example 27: A Preparation Method of 2-(4-chloro-2-fluoro-5-(3-(4-iodophenyl)-1,2,4-oxadiazole-5-yl)methoxy)phenyl)-4,5,6,7-tetrahydro-1H-isoindole-1,3(2H)-dione (Corresponding to Compound A27) was Performed According to the Following Procedures: a Reaction Equation was as Follows

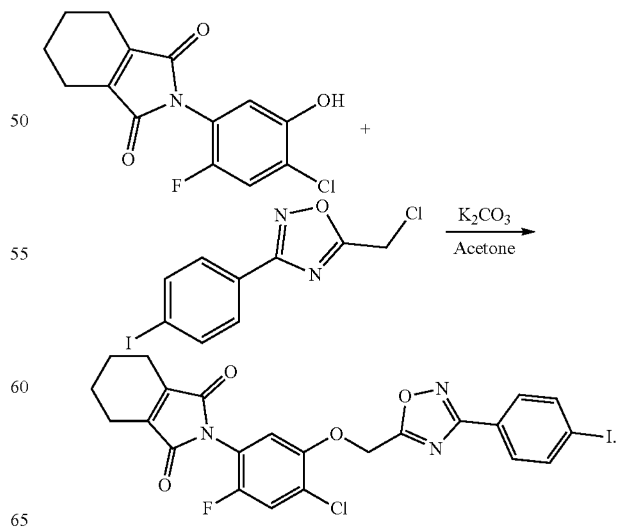

Steps (1) to (4) were the same as those in Example 1.

(5) Preparation of 2-(4-chloro-2-fluoro-5-(3-(4-iodophenyl)-1,2,4-oxadiazole-5-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 5-(chloromethyl)-3-(4-iodophenyl)-1,2,4-oxadiazole (0.33 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.42 g, 85%).

Example 28: A Preparation Method of 2-(4-chloro-2-fluoro-5-(5-(2-fluorophenyl)-1,3,4-oxadiazole-2-yl)methoxy)phenyl)-4,5,6,7-tetrahydro-1H-isoindole-1,3(2H)-dione (Corresponding to Compound B1) was Performed According to the Following Procedures (1) Preparation of 2-fluorobenzoic Hydrazide: a Reaction Equation was as Follows

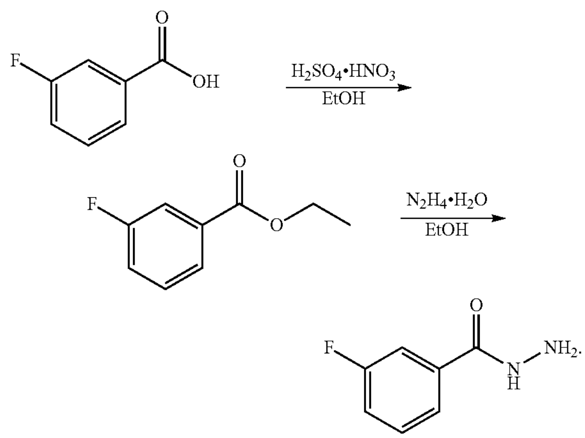

2-fluorobenzoic acid (5 g, 35.69 mM) was mixed with 30 mL of absolute ethanol in a 100 mL three-necked flask, concentrated sulfuric acid (10 g, 107.06 mM) was slowly added dropwise under a condition that the flask is in an ice bath, stirred for 1 h, and a resulting mixture was heated to 90° C. and then subjected to reaction under reflux, wherein the reaction was monitored by TLC. After the reaction, an obtained reaction system was cooled to ambient temperature, slowly poured into water, adjusted pH thereof to neutral with a sodium bicarbonate solution, and extracted with ethyl acetate to obtain an organic phase. The organic phase was dried with anhydrous sodium sulfate and concentrated to obtain an oily liquid. The oily liquid was purified with a silica gel column using petroleum ether: ethyl acetate (v/v=4:1) as an eluent to obtain a solid (6.00 g, 86%). Ethyl 2-fluorobenzoate (5 g, 29.73 mM) was dissolved in 30 mL of absolute ethanol, and added with 80% hydrazine hydrate (1.49 g, 29.73 mM) at ambient temperature, and a resulting mixture was heated to 80° C. and hold at 80° C. for 3 h and then subjected to reaction under reflux. After the reaction was completed, an obtained reaction solution was distilled under reduced pressure to remove the solvent, and recrystallized with ethanol to obtain a solid product (5.00 g, 79%).

(2) Preparation of 2-(chloromethyl)-5-(3-fluorophenyl)-1,3,4-oxadiazole: a Reaction Equation was as Follows

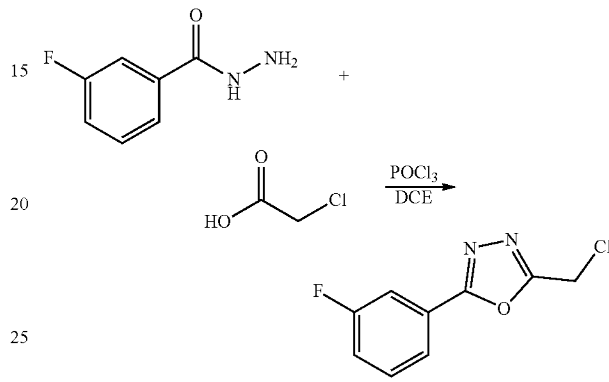

3-fluorobenzoic hydrazide (0.73 g, 3.67 mM) was dissolved in 15 mL of 1,2-dichloroethane and stirred for a while, chloroacetic acid (0.70 g, 7.33 mM) and phosphorus oxychloride (1.70 g, 11.0 mM) were added, and a resulting mixture was heated to 90° C. and hold at 90° C. and then subjected to reaction under reflux, wherein the reaction was monitored by TLC. After the reaction was completed, a resulting reaction solution was quenched with ice water, adjusted pH to neutral with saturated sodium bicarbonate, and extracted with dichloromethane to obtain an organic phase, and the organic phase was dried with anhydrous sodium sulfate, concentrated, and purified with silica gel column chromatography to obtain a white solid (0.63 g, 70%). The compound was characterized by: $^1$H NMR (400 MHz, $CDCl_3$) δ 7.9 (ddd, J=7.8, 1.6, 1.0 Hz, 1H), 7.8 (ddd, J=9.0, 2.6, 1.5 Hz, 1H), 7.5 (td, J=8.1, 5.5 Hz, 1H), 7.3 (tdd, J=8.3, 2.6, 1.0 Hz, 1H), 4.8 (s, 2H).

(3) Preparation of 4-chloro-2-fluoro-5-aminophenol: a Reaction Equation was as Follows

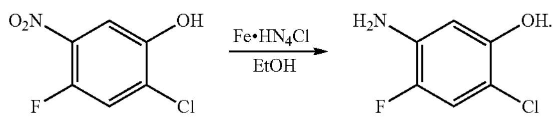

4-chloro-2-fluoro-5-nitrophenol (10 g, 52.21 mM) was dissolved in 100 mL of 90 vol % ethanol in a 250 mL three-necked round-bottom flask, $NH_4Cl$ (8.75 g, 156.62 mM) was added under stirring, and a resulting mixture was heated to 90° C. and then subjected to reaction. When an obtained reaction system was refluxed, an Fe powder (8.38 g, 156.62 mM) was added in batches, and the reflux was continued for 3 h. After the reaction was completed, an obtained reaction solution was subjected to suction filtration while hot, and an obtained filter cake was washed three times with hot ethanol, and an obtained filtrate was concentrated, such that a large amount of dark brown solid was precipitated, and then recrystallized with ethanol to obtain the 4-chloro-2-fluoro-5-aminophenol (7.76 g, 92%).

(4) Preparation of 2-(4-chloro-2-fluoro-5-hydroxybenzene)-4,5,6,7-tetrahydro-1H-isoindole-1,3(2H)-dione: a Reaction Equation was as Follows

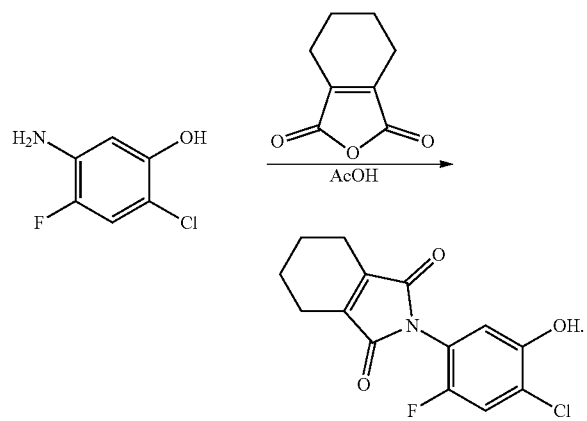

4-chloro-2-fluoro-5-aminophenol (7 g, 43.33 mM) was mixed with 50 mL of glacial acetic acid in a 100 mL three-necked round-bottom flask, 4,5,6,7-tetrahydroisobenzofuran-1,3-dione (7.25 g, 47.66 mM) was added, and a resulting system was heated to 100° C. for a reaction. After the reaction was completed, a resulting product system was poured into ice water, such that a large amount of milky white solid was precipitated, and then subjected to suction filtration to obtain an off-white solid (11.40 g, 89%).

(5) Preparation of 2-(4-chloro-2-fluoro-5-(5-(3-fluorophenyl)-1,3,4-oxadiazole-2-yl)methoxy)phenyl)-4,5,6,7-tetrahydro-1H-isoindole-1,3(2H)-dione: a Reaction Equation was as Follows

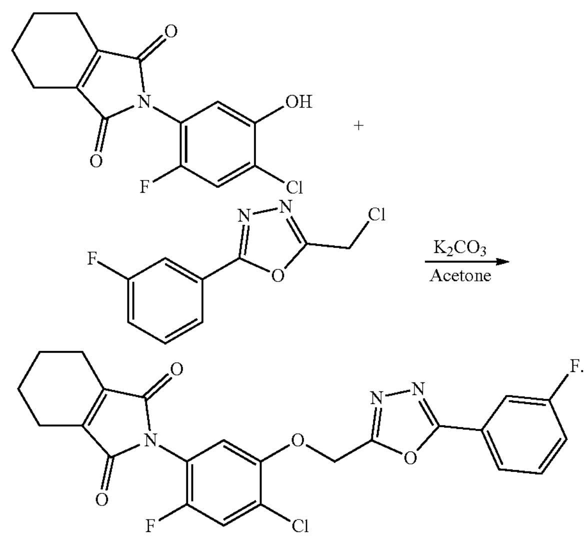

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 2-(chloromethyl)-5-(3-fluorophenyl)-1,3,4-oxadiazole (0.24 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.41 g, 88%).

Example 29: A Preparation Method of 2-(4-chloro-5-((5-(3-chlorophenyl)-1,3,4-oxadiazole-2-yl) methoxy)-2-fluorophenyl)-4,5,6,7-tetrahydro-1H-isoindole-1,3(2H)-dione (Corresponding to Compound B2) was Performed According to the Following Procedures: a Reaction Equation was as Follows

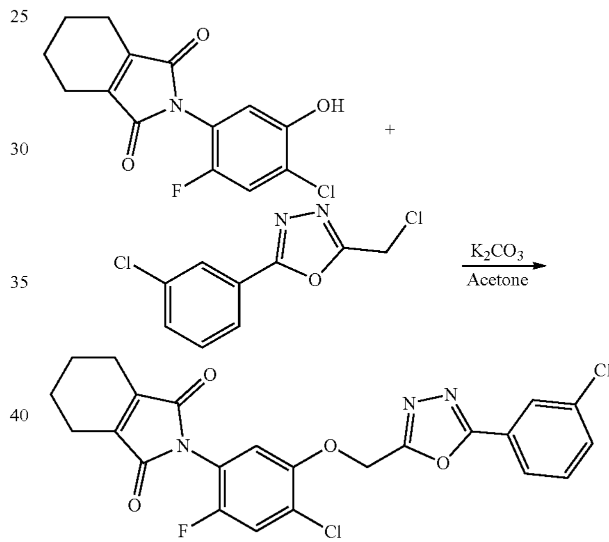

Steps (1) to (4) were the same as those in Example 28.

(5) Preparation of 2-(4-chloro-5-((5-(3-chlorophenyl)-1,3,4-oxadiazole-2-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(3-chlorophenyl)-1,3,4-oxadiazole (0.26 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.43 g, 81%).

Example 30: A Preparation Method of 2-(4-chloro-2-fluoro-5-(5-(3-tolyl)-1,3,4-oxadiazole-2-methoxy)phenyl)-4,5,6,7-tetrahydro-1H-isoindole-1,3(2H)-dione (Corresponding to Compound B3) was Performed According to the Following Procedures: a Reaction Equation was as Follows

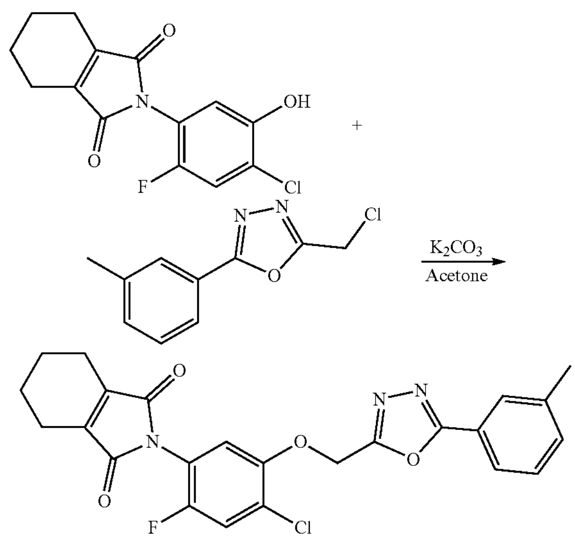

Steps (1) to (4) were the same as those in Example 28.

(5) Preparation of 2-(4-chloro-2-fluoro-5-(5-(3-tolyl)-1,3,4-oxadiazole-2-methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(3-tolyl)-1,3,4-oxadiazole (0.24 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.35 g, 75%).

Example 31: A Preparation Method of 2-(4-chloro-2-fluoro-5-(5-(2-fluorophenyl)-1,3,4-oxadiazole-2-yl)methoxy)phenyl)-4,5,6,7-tetrahydro-1H-isoindole-1,3(2H)-dione (Corresponding to Compound B4) was Performed According to the Following Procedures: a Reaction Equation was as Follows

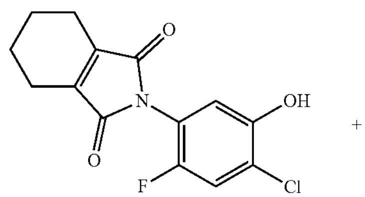

+

-continued

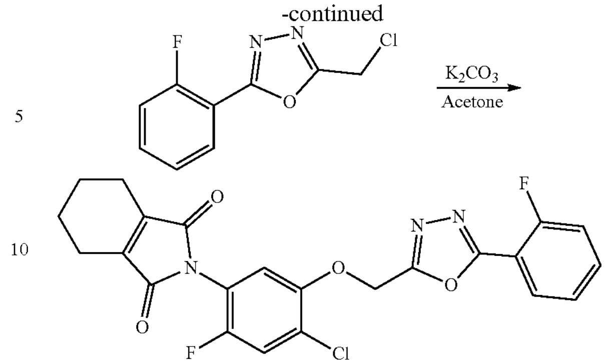

Steps (1) to (4) were the same as those in Example 28.

(5) Preparation of 2-(4-chloro-2-fluoro-5-(5-(2-fluorophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(2-fluorophenyl)-1,3,4-oxadiazole (0.24 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.37 g, 78%).

Example 32: A Preparation Method of 2-(4-chloro-5-(5-(2-chlorophenyl)-1,3,4-oxadiazole-2-yl)methoxy)-2-fluorophenyl)-4,5,6,7-tetrahydro-1H-isoindole-1,3(2H)-dione (Corresponding to Compound B5) was Performed According to the Following Procedures: a Reaction Equation was as Follows

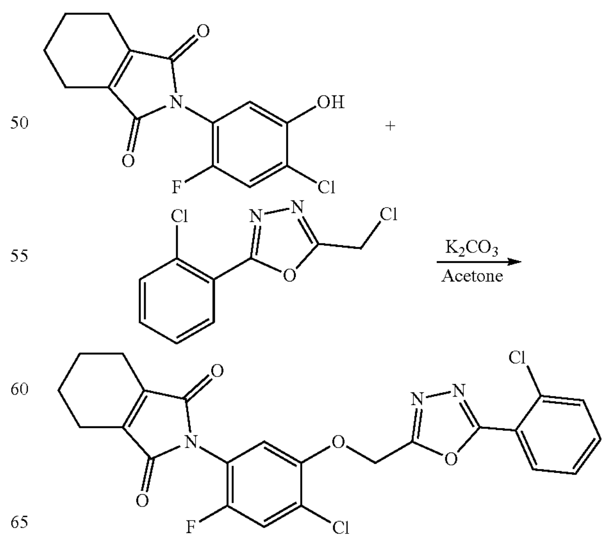

Steps (1) to (4) were the same as those in Example 28.

(5) Preparation of 2-(4-chloro-5-(5-(2-chlorophenyl)-1,3,4-oxadiazole-2-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(2-chlorophenyl)-1,3,4-oxadiazole (0.26 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.36 g, 79%).

Example 33: A Preparation Method of 2-(5-(5-(2-bromophenyl)-1,3,4-oxadiazole-2-yl)methoxy)-4-chloro-2-fluorophenyl)-4,5,6,7-tetrahydro-1H-isoindole-1,3(2H)-dione (Corresponding to Compound B6) was Performed According to the Following Procedures: a Reaction Equation was as Follows

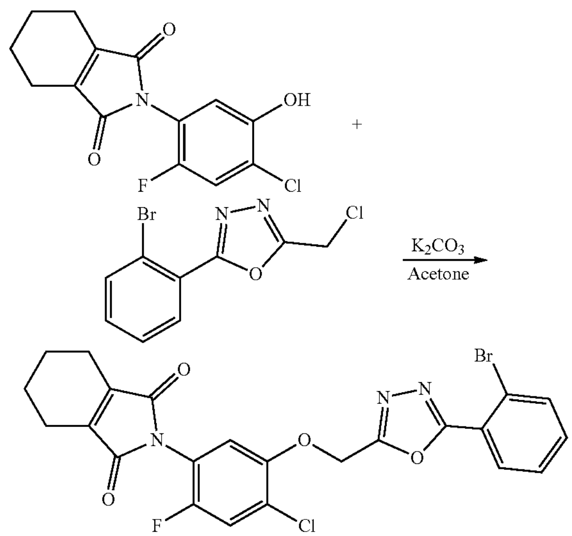

Steps (1) to (4) were the same as those in Example 28.

(5) Preparation of 2-(5-(5-(2-bromophenyl)-1,3,4-oxadiazole-2-yl)methoxy)-4-chloro-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(2-bromophenyl)-1,3,4-oxadiazole (0.31 g, 1.17 mM) was added, and a resulting mixture was heated to 60° C. and then subjected to reaction under reflux. After the reaction was completed, a resulting product was filtered to remove potassium carbonate, and extracted to obtain an organic phase, and the organic phase was dried with anhydrous sodium sulfate, concentrated, and purified with silica gel chromatography to obtain a target compound (0.31 g, 75%).

Example 34: A Preparation Method of 2-(4-chloro-2-fluoro-5-(5-(2-iodophenyl)-1,3,4-oxadiazole-2-yl)methoxy)phenyl)-4,5,6,7-tetrahydro-1H-isoindole-1,3(2H)-dione (Corresponding to Compound B7) was Performed According to the Following Procedures: a Reaction Equation was as Follows

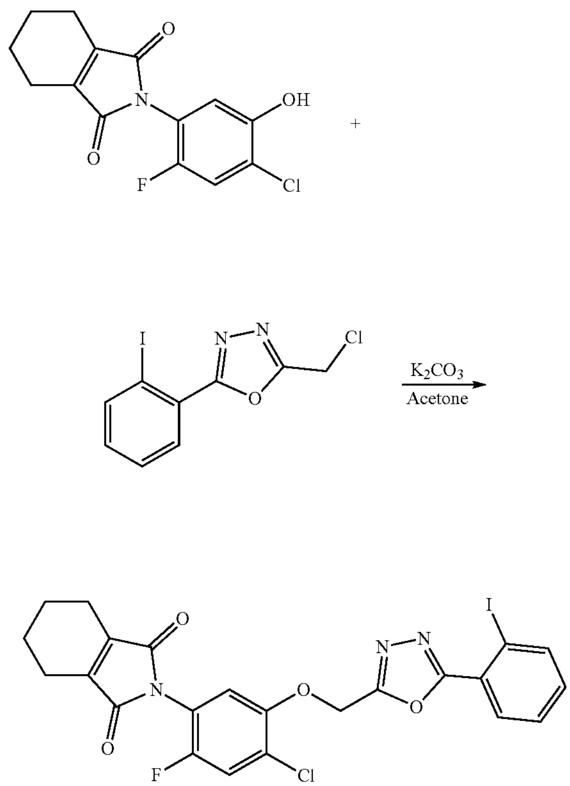

Steps (1) to (4) were the same as those in Example 28.

(5) Preparation of 2-(4-chloro-2-fluoro-5-(5-(2-iodophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(2-iodophenyl)-1,3,4-oxadiazole (0.37 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.33 g, 77%).

Example 35: A Preparation Method of 2-(4-chloro-2-fluoro-5-(5-(2-nitrophenyl)-1,3,4-oxadiazole-2-yl) methoxy)phenyl)-4,5,6,7-tetrahydro-1H-isoindole-1,3(2H)-dione (Corresponding to Compound B8) was Performed According to the Following Procedures: a Reaction Equation was as Follows

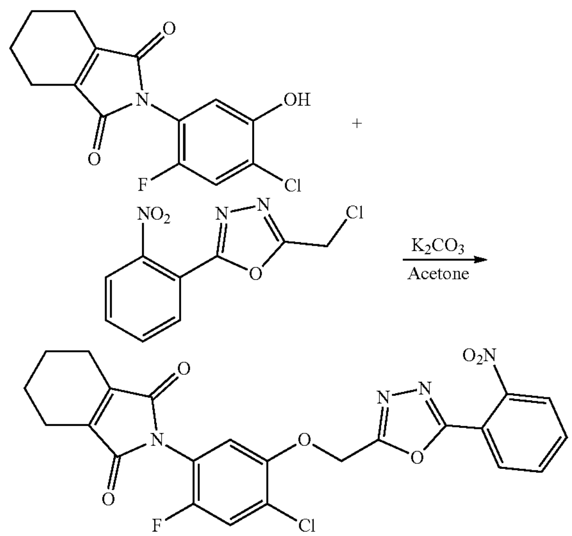

Steps (1) to (4) were the same as those in Example 28.

(5) Preparation of 2-(4-chloro-2-fluoro-5-(5-(2-nitrophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(2-nitrophenyl)-1,3,4-oxadiazole (0.28 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.30 g, 65%).

Example 36: A Preparation Method of 2-(4-chloro-2-fluoro-5-((5-(2-tolyl)-1,3,4-oxadiazole-2-yl) methoxy)phenyl)-4,5,6,7-tetrahydro-1H-isoindole-1,3(2H)-dione (Corresponding to Compound B9) was Performed According to the Following Procedures: a Reaction Equation was as Follows

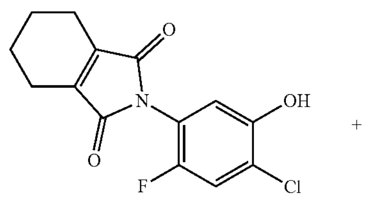

+

-continued

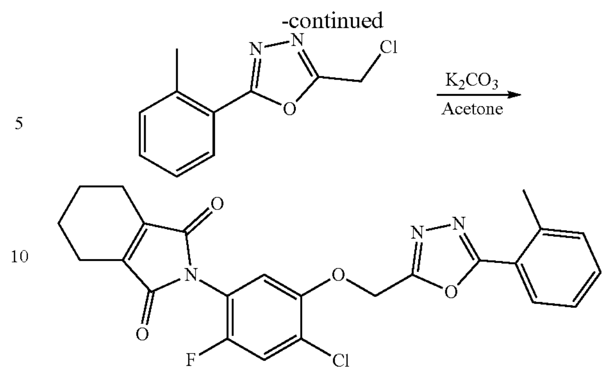

Steps (1) to (4) were the same as those in Example 28.

(5) Preparation of 2-(4-chloro-2-fluoro-5-((5-(o-tolyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) added stirred was and for 30 min, 2-(chloromethyl)-5-(2-tolyl)-1,3,4-oxadiazole (0.24 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.37 g, 78%).

Example 37: A Preparation Method of 2-(5-(5-(3-bromophenyl)-1,3,4-oxadiazole-2-yl)methoxy)-4-chloro-2-fluorophenyl)-4,5,6,7-tetrahydro-1H-isoindole-1,3(2H)-dione (Corresponding to Compound B10) was Performed According to the Following Procedures: a Reaction Equation was as Follows

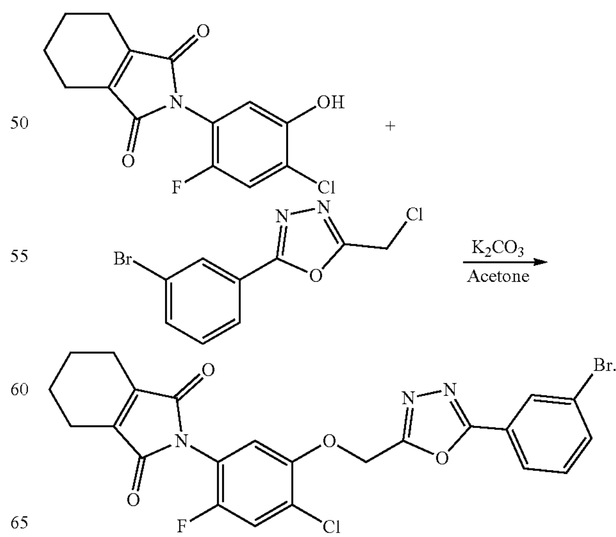

Steps (1) to (4) were the same as those in Example 28.

(5) Preparation of 2-(5-(5-(3-bromophenyl)-1,3,4-oxadiazole-2-yl)methoxy)-4-chloro-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(3-bromophenyl)-5-(chloromethyl)-1,3,4-oxadiazole (0.31 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.39 g, 79%).

Example 38: A Preparation Method of 2-(4-chloro-2-fluoro-5-(5-(3-iodophenyl)-1,3,4-oxadiazole-2-yl)methoxy)phenyl)-4,5,6,7-tetrahydro-1H-isoindole-1,3(2H)-dione (Corresponding to Compound B11) was Performed According to the Following Procedures: a Reaction Equation was as Follows

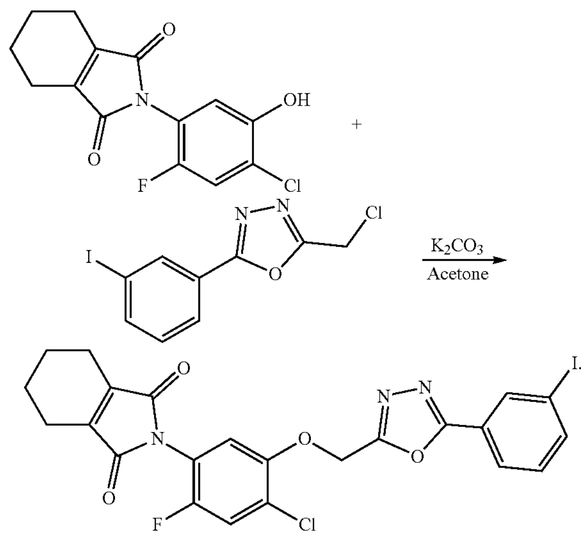

Steps (1) to (4) were the same as those in Example 28.

(5) Preparation of 2-(4-chloro-2-fluoro-5-(5-(3-iodophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(3-iodophenyl)-1,3,4-oxadiazole (0.37 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.34 g, 76%).

Example 39: A Preparation Method of 2-(4-chloro-2-fluoro-5-(5-(3-nitrophenyl)-1,3,4-oxadiazole-2-yl)methoxy)phenyl)-4,5,6,7-tetrahydro-1H-isoindole-1,3(2H)-dione (Correspond to Compound B12) was Performed According to the Following Procedures: a Reaction Equation was as Follows

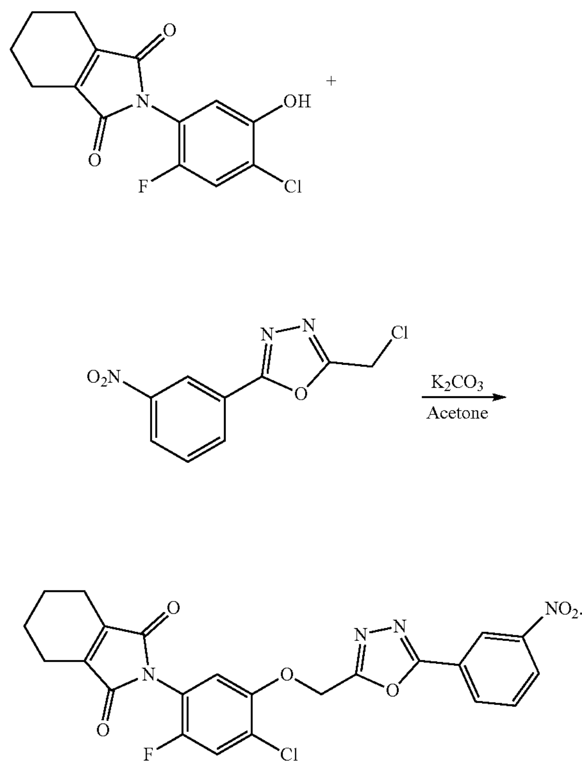

Steps (1) to (4) were the same as those in Example 28.

(5) Preparation of 2-(4-chloro-2-fluoro-5-(5-(3-nitrophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred 30 min, 2-(chloromethyl)-5-(3-nitromethyl)-1,3,4-oxadiazole (0.28 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.36 g, 74%).

Example 40: A Preparation Method of 2-(4-chloro-2-fluoro-5-((5-(4-tolyl)-1,3,4-oxadiazole-2-yl) methoxy)phenyl)-4,5,6,7-tetrahydro-1H-isoindole-1,3(2H)-dione (Corresponding to Compound B13) was Performed According to the Following Procedures: a Reaction Equation was as Follows

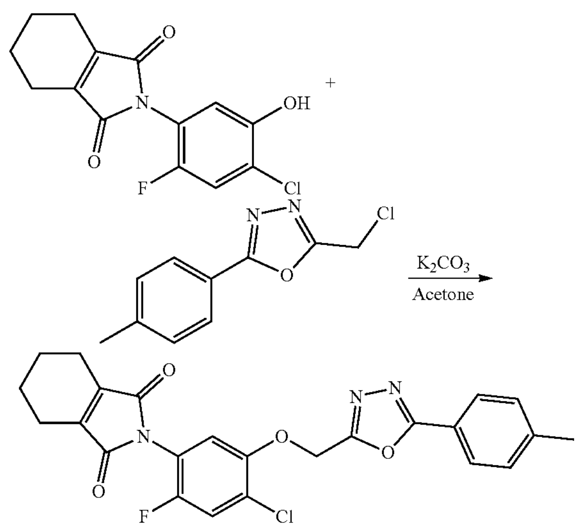

Steps (1) to (4) were the same as those in Example 28.

(5) Preparation of 2-(4-chloro-2-fluoro-5-((5-(4-tolyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(4-tolyl)-1,3,4-oxadiazole (0.24 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.36 g, 81%).

Example 41: A Preparation Method of 2-(4-chloro-2-fluoro-5-(5-(4-fluorophenyl)-1,3,4-oxadiazole-2-yl)methoxy)phenyl)-4,5,6,7-tetrahydro-1H-isoindole-1,3(2H)-dione (Corresponding to Compound B14) was Performed According to the Following Procedures: a Reaction Equation was as Follows

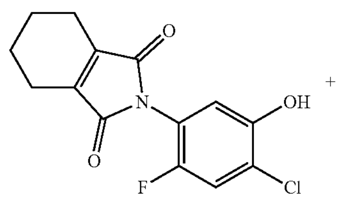

-continued

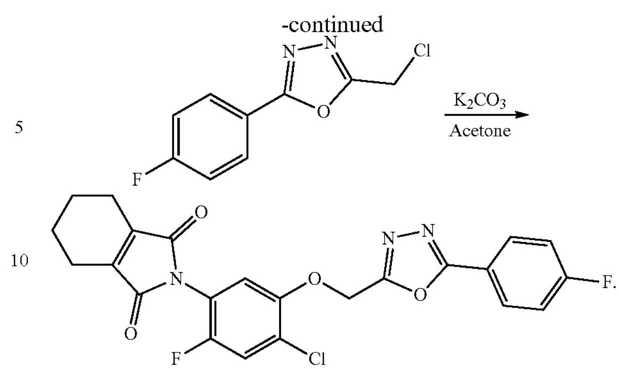

Steps (1) to (4) were the same as those in Example 28.

(5) Preparation of 2-(4-chloro-2-fluoro-5-(5-(4-fluorophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(4-fluorophenyl)-1,3,4-oxadiazole (0.24 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.32 g, 76%).

Example 42: A Preparation Method of 2-(4-chloro-5-(5-(4-chlorophenyl)-1,3,4-oxadiazole-2-yl) methoxy)-2-fluorophenyl)-4,5,6,7-tetrahydro-1H-isoindole-1,3(2H)-dione (Corresponding to Compound B15) was Performed According to the Following Procedures: a Reaction Equation was as Follows

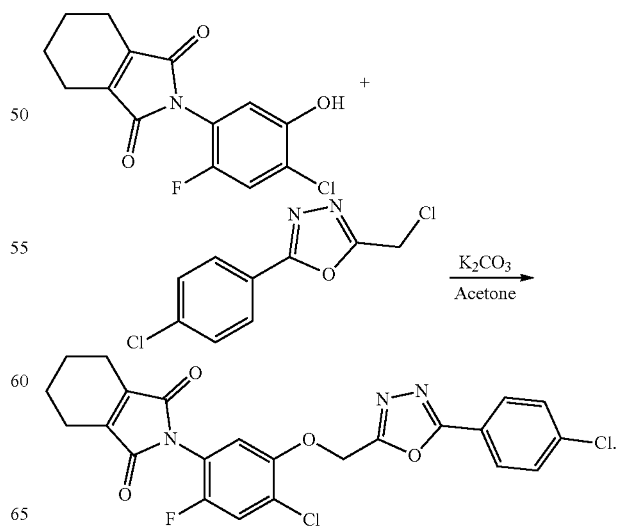

Steps (1) to (4) were the same as those in Example 28.

(5) Preparation of 2-(4-chloro-5-(5-(4-chlorophenyl)-1,3,4-oxadiazole-2-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(4-chlorophenyl)-1,3,4-oxadiazole (0.26 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.35 g, 75%).

Example 43: A Preparation Method of 2-(4-chloro-2-fluoro-5-(5-(4-bromophenyl)-1,3,4-oxadiazole-2-yl)methoxy)phenyl)-4,5,6,7-tetrahydro-1H-isoindole-1,3(2H)-dione (Corresponding to Compound B16) was Performed According to the Following Procedures: a Reaction Equation was as Ffollows

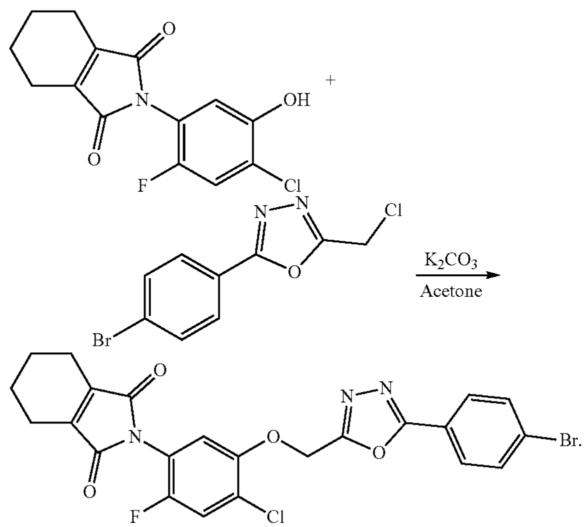

Steps (1) to (4) were the same as those in Example 28.

(5) Preparation of 2-(4-chloro-2-fluoro-5-(5-(4-bromophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(4-bromophenyl)-1,3,4-oxadiazole (0.31 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.33 g, 71%).

Example 44: A Preparation Method of 2-(4-chloro-2-fluoro-5-(5-(4-iodophenyl)-1,3,4-oxadiazole-2-yl)methoxy)phenyl)-4,5,6,7-tetrahydro-1H-isoindole-1,3(2H)-dione (Corresponding to Compound B17) was Performed According to the Following Procedures: a Reaction Equation was as Follows

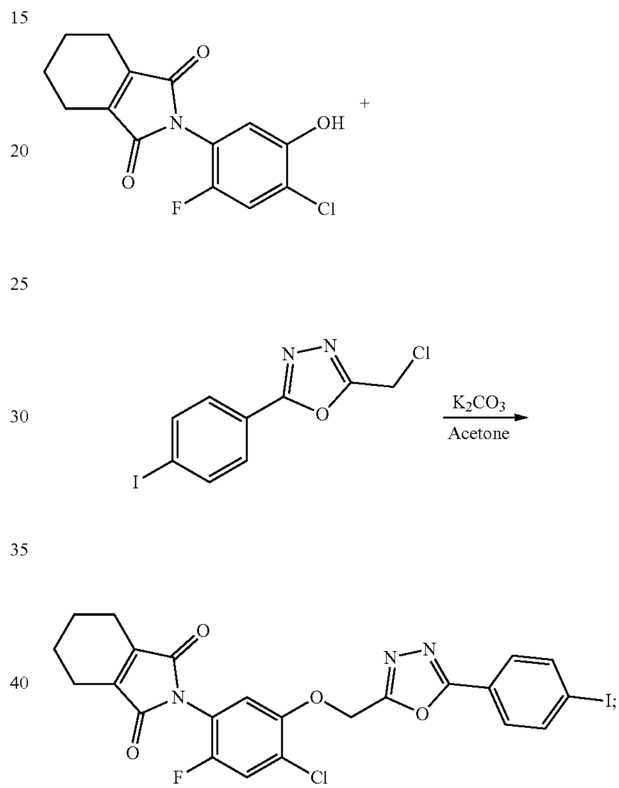

Steps (1) to (4) were the same as those in Example 28.

(5) Preparation of 2-(4-chloro-2-fluoro-5-(5-(4-iodophenyl)-1,3,4-oxadiazole-2-yl)methoxy)phenyl)-4,5,6,7-tetrahydro-1H-isoindole-1,3(2)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(4-iodophenyl)-1,3,4-oxadiazole (0.37 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.36 g, 79%).

Example 45: A Preparation Method of 2-(4-chloro-2-fluoro-5-(5-(4-nitrophenyl)-1,3,4-oxadiazole-2-yl)methoxy)phenyl)-4,5,6,7-tetrahydro-1H-isoindole-1,3(2H)-dione (Corresponding to Compound B18) was Performed According to the Following Procedures: a Reaction Equation was as Follows

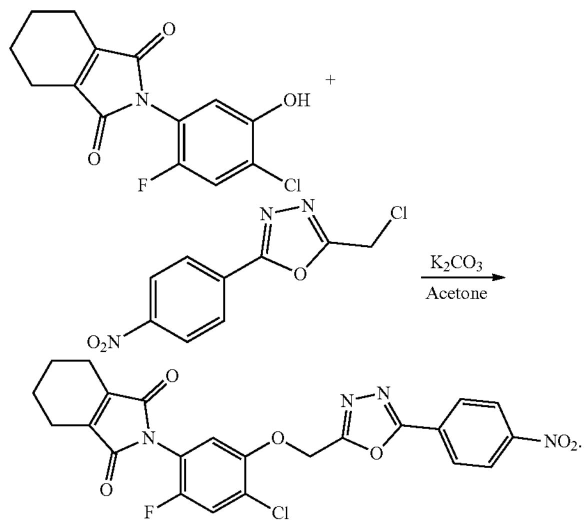

Steps (1) to (4) were the same as those in Example 28.

(5) Preparation of 2-(4-chloro-2-fluoro-5-(5-(4-nitrophenyl)-1,3,4-oxadiazole-2-yl)methoxy)phenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(4-nitrophenyl)-1,3,4-oxadiazole (0.28 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.35 g, 78%).

Example 46: A Preparation Method of 2-(4-chloro-5-(5-(4-chloro-2-fluorophenyl)-1,3,4-oxadiazole-2-yl)methoxy)-2-fluorophenyl)-4,5,6,7-tetrahydro-1H-isoindole-1,3(2H)-dione (Corresponding to Compound B19) was Performed According to the Following Procedures: a Reaction Equation was as Follows

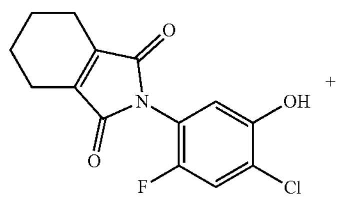

-continued

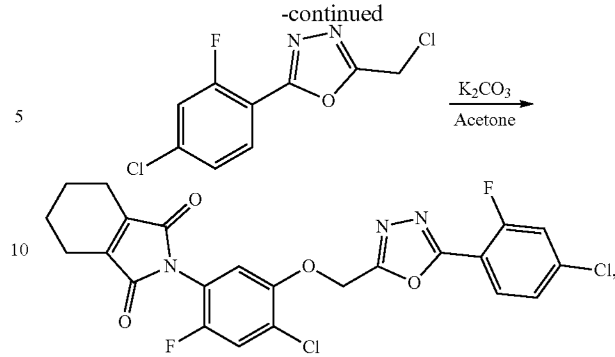

Steps (1) to (4) were the same as those in Example 28.

(5) Preparation of 2-(4-chloro-5-(5-(4-chloro-2-fluorophenyl)-1,3,4-oxadiazole-2-yl)methoxy)-2-fluorophenyl)-4,5,6,7-tetrahydro-1H-isoindole-1,3(2H)-dione At ambient temperature, 2-(4-chloro-2-fluoro-5-hydroxybenzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(4-chloro-2-fluorophenyl)-5-(chloromethyl)-1,3,4-oxadiazole (0.28 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.31 g, 65%).

Example 47: A Preparation Method of 2-(4-chloro-2-fluoro-5-(5-(2-fluoro-4-nitrophenyl)-1,3,4-oxadiazole-2-yl)methoxy)phenyl)-4,5,6,7-tetrahydro-1H-isoindole-1,3(2H)-dione (Corresponding to Compound B20) was Performed According to the Following Procedures: a Reaction Equation was as Follows

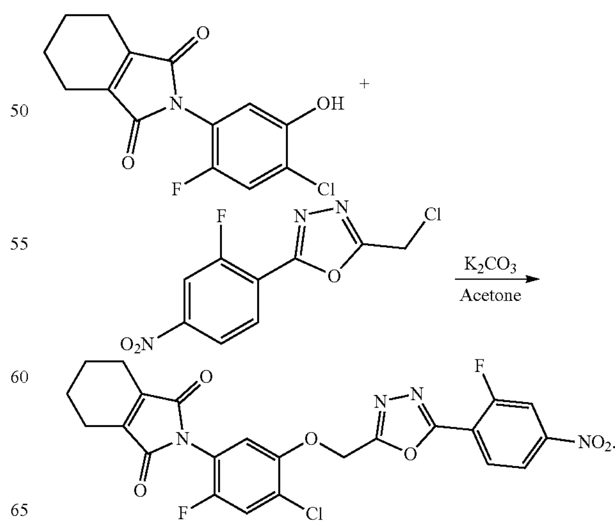

Steps (1) to (4) were the same as those in Example 28.

(5) Preparation of 2-(4-chloro-2-fluoro-5-(5-(2-fluoro-4-nitrophenyl)-1,3,4-oxadiazole-2-yl) methoxy)phenyl)-4,5,6,7-tetrahydro-1H-isoindole-1,3(2H)-dione At ambient temperature, 2-(4-chloro-2-fluoro-5-hydroxy-benzene)-4,5,6,7-tetrahydro-1H-isoindole-1,3(2H)-dione (0.30 g, 1.17 mM) was dissolved in 15 mL of acetone in a 25 mL three-necked flask, potassium carbonate (0.49 g, 3.52 mM) was added and stirred for 30 min, 2-(chloromethyl)-5-(2-fluoro-4-nitrophenyl)-1,3,4-oxadiazole (0.30 g, 1.17 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.33 g, 75%).

Example 48: A Preparation Method of 2-(4-chloro-2-fluoro-5-(2-oxo-2-phenylethoxy)phenyl)-4,5,6,7-tetrahydro-1H-isoindole-1,3(2H)-dione (Corresponding to Compound C1) was Performed According to the Following Procedures (1) Preparation of α-bromo(chloro)acetophenone: a Reaction Equation was as Follows

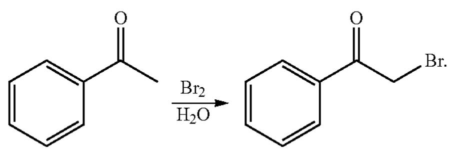

Acetophenone (12 g, 100 mM) and 50 mL of water as a solvent were added into a three-necked flask, stirred slowly and heated to 90° C. Liquid bromine (16.8 g, 105 mM) was slowly added dropwise to obtain a mixture, the mixture was hold at 60° C., and stirred for 4 h, then cooled to ambient temperature, filtered, and then recrystallized with methanol to obtain a product. The compound was characterized by: $^1$H NMR (500 MHz, $CDCl_3$) δ 8.0-7.9 (m, 2H), 7.6-7.5 (m, 3H), 4.7 (s, 2H).

(2) Preparation of 2-(4-chloro-2-fluoro-5-hydroxy-benzene)-4,5,6,7-tetrahydro-1H-isoindole-1,3(2H)-dione This step was the same as that in Example 1.

(3) Preparation of 2-(4-chloro-2-fluoro-5-(2-oxo-2-phenylethoxy)phenyl)-4,5,6,7-tetrahydro-1H-isoindole-1,3(2H)-dione: a Reaction Equation was as Follows

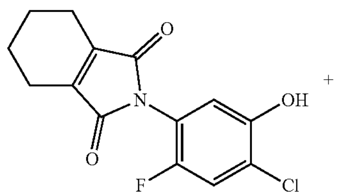

-continued

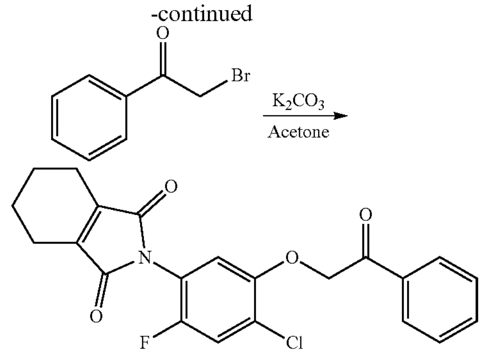

At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 2-bromoacetophenone (0.20 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.38 g, 81%).

Example 49: A Preparation Method of 2-(4-chloro-2-fluoro-5-(2-oxo-2-(4-methyl)ethoxy)phenyl)-4,5,6,7-tetrahydro-1H-isoindole-1,3(2H)-dione (Corresponding to Compound C2) was Performed According to the Following Procedures: a Reaction Equation was as Follows

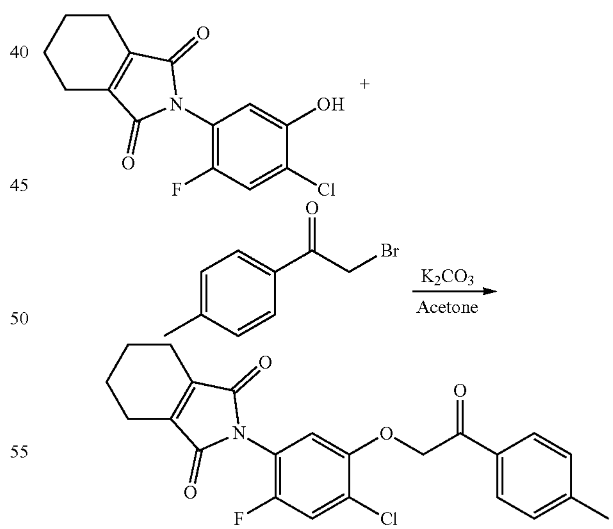

At ambient temperature, 2-(4-chloro-2-fluoro-5-hydroxy-benzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 2-bromo-1-(4-methylphenyl)ethyl ketone (0.22 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.35 g, 83%).

Example 50: A Preparation Method of 2-(4-chloro-2-fluoro-5-(2-oxo-2-(4-cyanophenyl)ethoxy)phenyl)-4,5,6,7-tetrahydro-1H-isoindole-1,3(2H)-dione (Corresponding to Compound C3) was Performed According to the Following Procedures: a Reaction Equation was as Follows

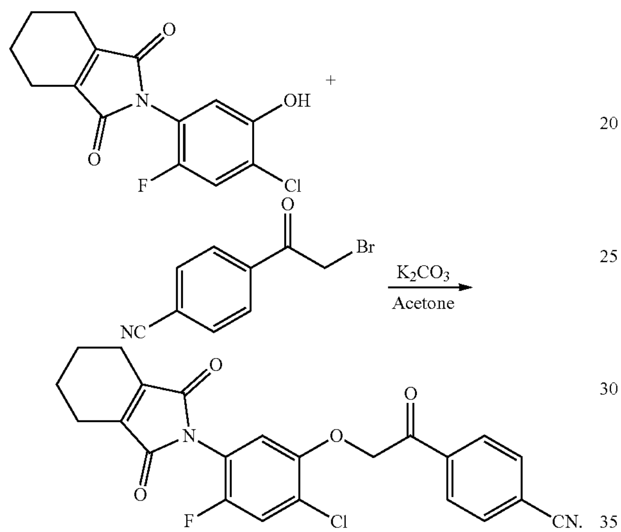

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.04 mM) was added and stirred for 30 min, 2-bromo-1-(4-cyanophenyl)ethyl ketone (0.24 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.34 g, 75%).

Example 51: A Preparation Method of 2-(4-chloro-2-fluoro-5-(2-oxo-2-(2-fluorophenyl)ethoxy)phenyl)-4,5,6,7-tetrahydro-1H-isoindole-1,3(2H)-dione (Corresponding to Compound C4) was Performed According to the Following Procedures: a Reaction Equation was as Follows

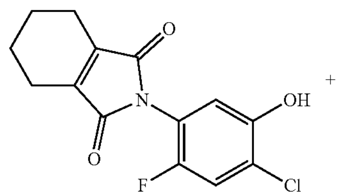

-continued

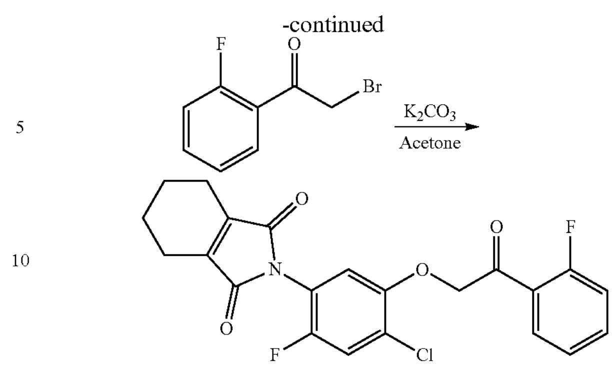

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(2-fluorophenyl)ethyl ketone (0.20 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.35 g, 78%).

Example 52: A Preparation Method of 2-(4-chloro-2-fluoro-5-(2-oxo-2-(3,5-difluorophenyl)ethoxy)phenyl)-4,5,6,7-tetrahydro-1H-isoindole-1,3(2H)-dione (Corresponding to Compound C5) was Performed According to the Following Procedures: a Reaction Equation was as Follows

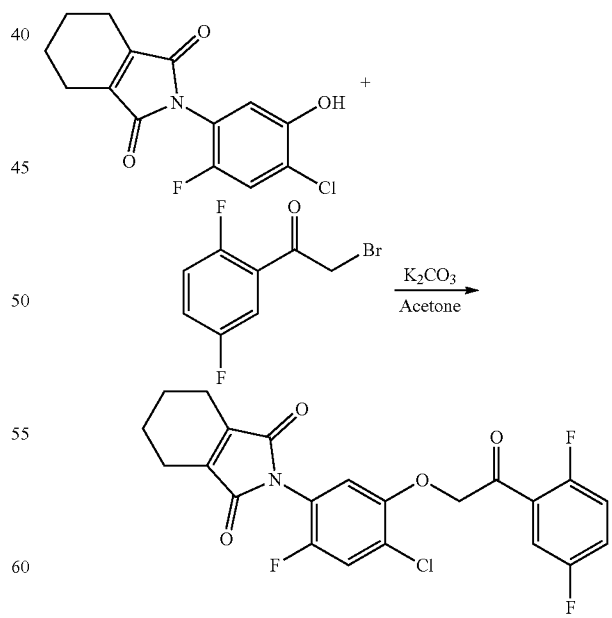

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(3,5-difluorophenyl)ethyl ketone (0.24 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.32 g, 74%).

Example 53: A Preparation Method of 2-(4-chloro-2-fluoro-5-(2-oxo-2-(2-methoxyphenyl)ethoxy)phenyl)-4,5,6,7-tetrahydro-1H-isoindole-1,3(2H)-dione (Corresponding to Compound C6) was Performed According to the Following Procedures: a Reaction Equation was as Follows

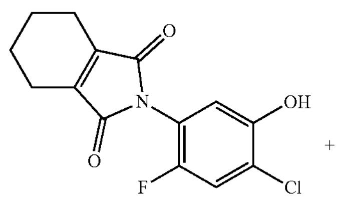

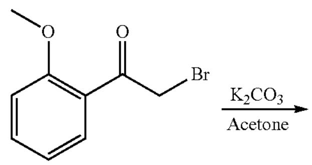

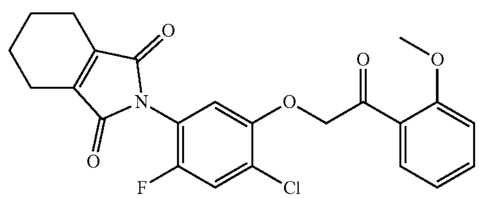

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(2-methoxyphenyl)ethyl ketone (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.33 g, 70%).

Example 54: A Preparation Method of 2-(4-chloro-2-fluoro-5-(2-oxo-2-(3-fluorophenyl)ethoxy)phenyl)-4,5,6,7-tetrahydro-1H-isoindole-1,3(2H)-dione (Corresponding to Compound C7) was Performed According to the Following Procedures: a Reaction Equation was as Follows

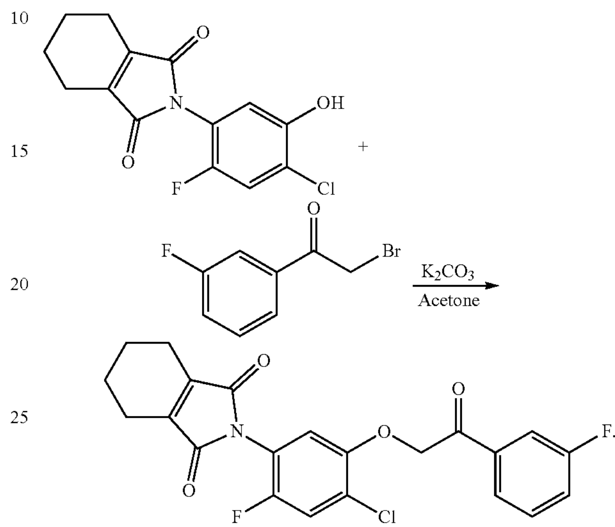

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(3-fluorophenyl)ethyl ketone (0.22 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.32 g, 79%).

Example 55: A Preparation Method of 2-(4-chloro-2-fluoro-5-(2-oxo-2-(4-fluorophenyl)ethoxy)phenyl)-4,5,6,7-tetrahydro-1H-isoindole-1,3(2H)-dione (Corresponding to Compound C8) was Performed According to the Following Procedures: a Reaction Equation was as Follows

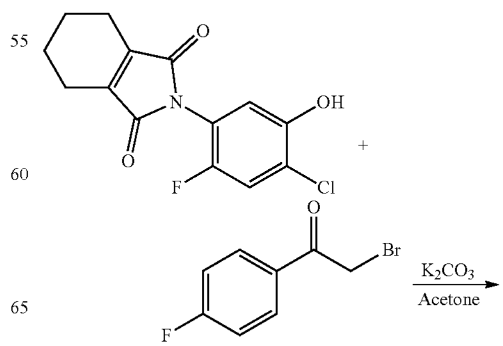

-continued

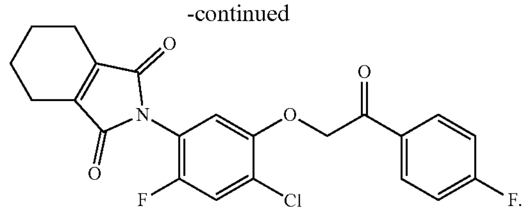

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(4-fluorophenyl)ethyl ketone (0.22 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.36 g, 82%).

Example 56: A Preparation Method of 2-(4-chloro-2-fluoro-5-(2-oxo-2-(4-nitrophenyl)ethoxy)phenyl)-4,5,6,7-tetrahydro-1H-isoindole-1,3(2H)-dione (Corresponding to Compound C9) was Performed According to the Following Procedures: a Reaction Equation was as Follows

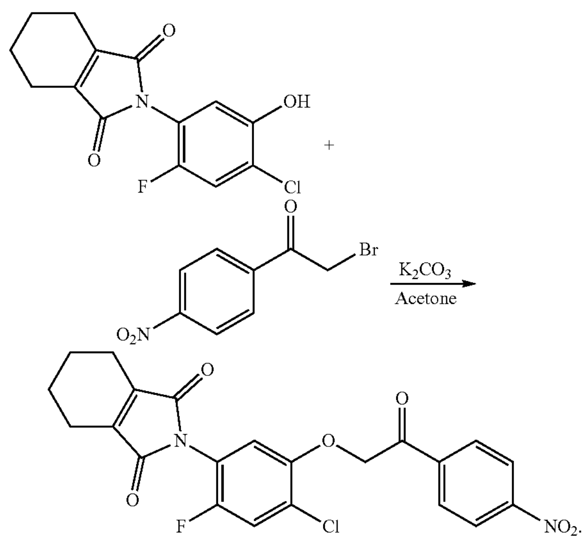

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(4-nitrophenyl)ethyl ketone (0.25 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.34 g, 75%).

Example 57: A Preparation Method of 2-(4-chloro-2-fluoro-5-((4-fluorobenzyl)oxy)phenyl)-4,5,6,7-tetrahydro-1H-isoindole-1,3(2H)-dione (Corresponding to Compound C10) was Performed According to the Following Procedures: a Reaction Equation was as Follows

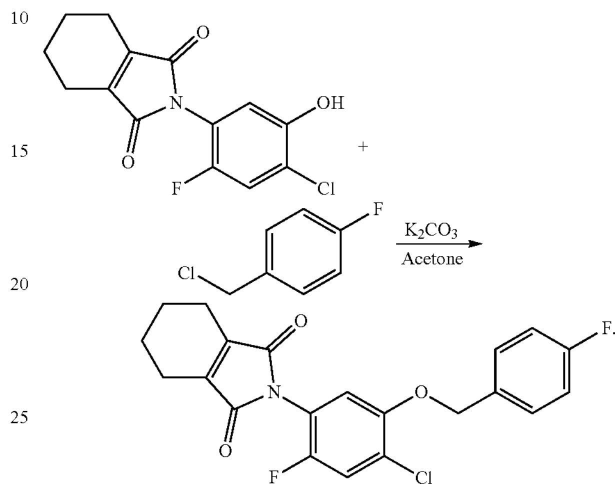

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 1-(chloromethyl)-4-fluorobenzene (0.15 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.35 g, 75%).

Example 58: A Preparation Method of 2-(4-chloro-2-fluoro-5-(2-oxo-2-(4-chlorophenyl)ethoxy)phenyl)-4,5,6,7-tetrahydro-1H-isoindole-1,3(2H)-dione (Corresponding to Compound C11) was Performed According to the Following Procedures: a Reaction Equation was as Follows

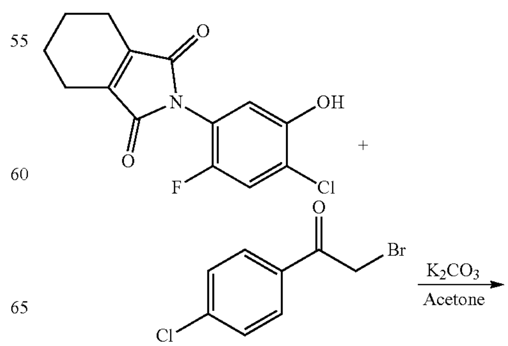

-continued

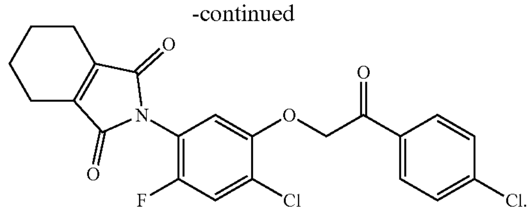

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(4-chlorophenyl)ethyl ketone (0.24 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.31 g, 68%).

Example 59: A Preparation Method of 2-(4-chloro-2-fluoro-5-(2-oxo-2-(2,4-difluorophenyl)ethoxy)phenyl)-4,5,6,7-tetrahydro-1H-isoindole-1,3(2H)-dione (Corresponding to Compound C12) was Performed According to the Following Procedures: a Reaction Equation was as Follows

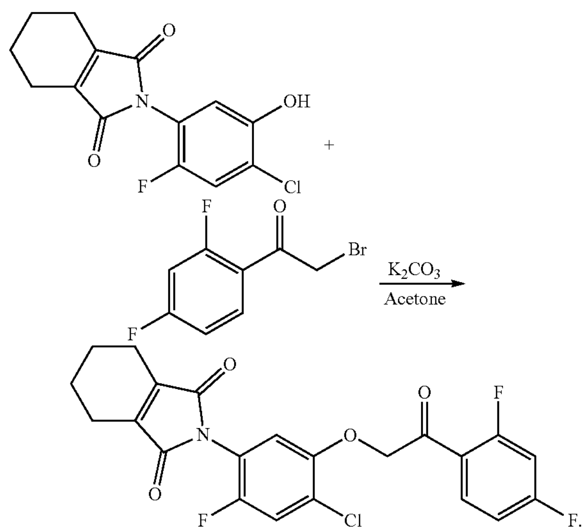

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(2,4-fluorophenyl)ethyl ketone (0.24 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.32 g, 69%).

Example 60: A Preparation Method of 2-(4-chloro-2-fluoro-5-(2-oxo-2-(4-methoxyphenyl)ethoxy)phenyl)-4,5,6,7-tetrahydro-1H-isoindole-1,3(2H)-dione (Corresponding to Compound C13) was Performed According to the Following Procedures: a Reaction Equation was as Follows

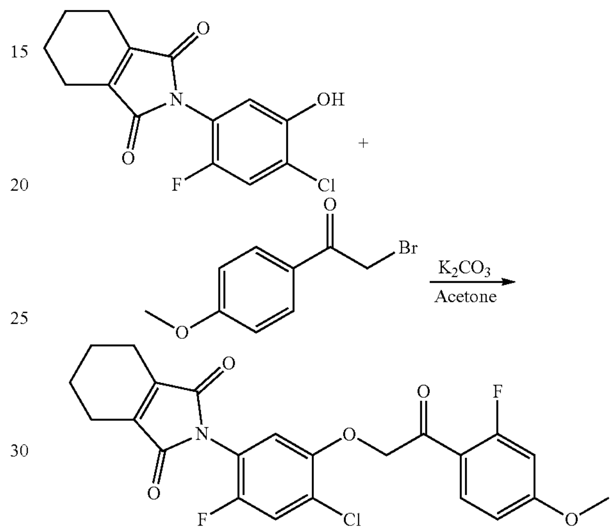

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(4-methoxyphenyl)ethyl ketone (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.35 g, 75%).

Example 61: A Preparation Method of 2-(4-chloro-2-fluoro-5-(2-oxo-2-(4-bromophenyl)ethoxy)phenyl)-4,5,6,7-tetrahydro-1H-isoindole-1,3(2H)-dione (Corresponding to Compound C14) was Performed According to the Following Procedures: a Reaction Equation was as Follows

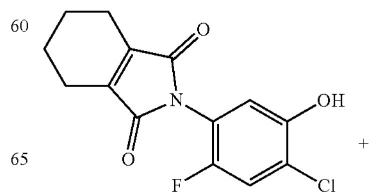

-continued

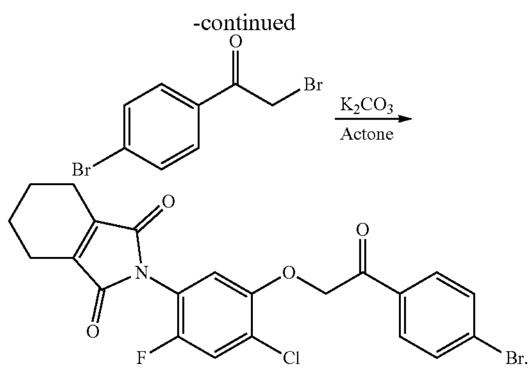

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(4-bromophenyl)ethyl ketone (0.23 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.34 g, 73%).

Example 62: A Preparation Method of 2-(2-fluoro-4-(2-oxo-2-(4-tolyl)ethoxy)phenyl)-4,5,6,7-tetrahydro-1H-isoindole-1,3(2H)-dione (Corresponding to Compound C15) was Performed According to the Following Procedures: a Reaction Equation was as Follows

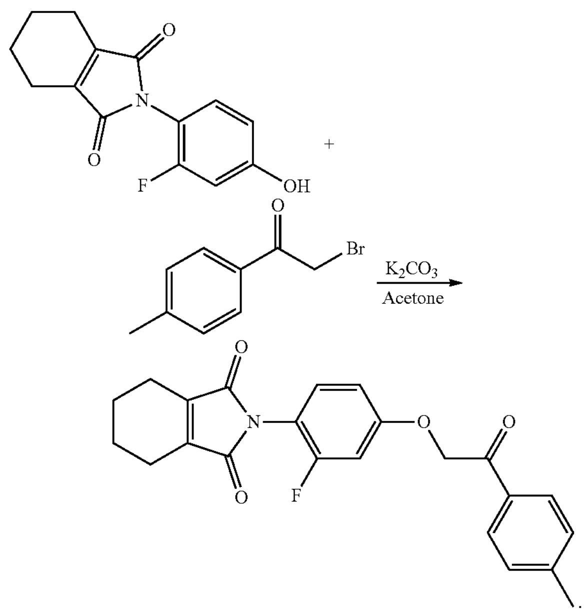

At ambient temperature, 2-(4-chloro-2-fluoro-5-hydroxybenzene)-4,5,6,7-tetrahydro-1H-isoindole-1,3(2H)-dione (0.30 g, 1.01 mM) was dissolved in 15 mL of acetone in a 25 mL three-necked flask, potassium carbonate (0.42 g, 3.01 mM) was added and stirred for 30 min, 2-bromo-1-(4-methylphenyl)ethyl ketone (0.22 g, 1.01 mM) was added, and a resulting mixture was heated to 60° C. and then subjected to reaction under reflux. After the reaction was completed, a resulting reaction solution was filtered to remove potassium carbonate, and extracted to obtain an organic phase, and the organic phase was dried with anhydrous sodium sulfate, concentrated, and purified with silica gel chromatography to obtain a target compound (0.32 g, 73%).

Example 63: A Preparation Method of N-(2-chloro-5-(1,3-dioxo-1,3,4,5,6,7-hexahydro-2H-isoindole-2-yl)-4-fluorophenyl)acetamide (Corresponding to Compound D1) was Performed According to the Following Procedures (1) Preparation of 2-(4-chloro-2-fluorophenyl)-4,5,6,7-tetrahydro-1H-isoindole-1,3(2H)-dione: a Reaction Equation was as Follows

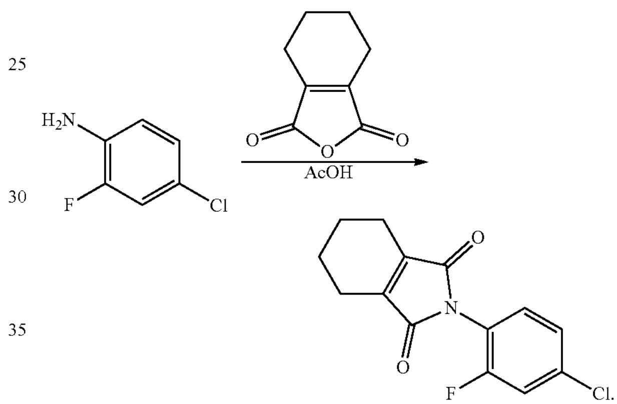

(1) 4-chloro-2-fluoroaniline (10.0 g, 68.7 mM) was dissolved in glacial acetic acid, 4,5,6,7-tetrahydroisobenzofuran-1,3-dione (10.45 g, 68.7 mM) was added thereto under stirring, and a resulting mixture was heated and then subjected to reaction under reflux. After the reaction was completed, a resulting reaction system was poured into ice water and stirred continuously, such that a large amount of solid was precipitated. A resulting system was subjected to suction filtration to obtain a filter cake. The filter cake was washed three times with a saturated sodium bicarbonate solution, and dried for subsequent use. The compound was characterized by: $^1H$ NMR (400 MHz, $CDCl_3$) δ 7.6 (dd, J=7.9, 5.1 Hz, 1H), 7.3 (ddd, J=8.2, 4.3, 2.0 Hz, 2H), 2.4 (m, J=3.1 Hz, 4H), 1.9-1.6 (m, 4H).

(2) Preparation of 2-(4-chloro-2-fluoro-5-nitrophenyl)-4,5,6,7-tetrahydro-1H-isoindole-1,3(2H)-dione: a Reaction Equation was as Follows

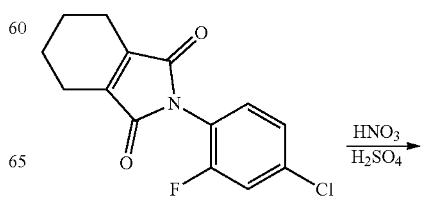

-continued

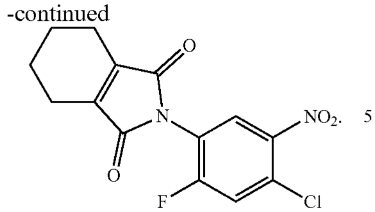

2-(4-chloro-2-fluorophenyl)-4,5,6,7-tetrahydro-1H-isoindole-1,3(2H)-dione (15 g, 53.63 mM) was dissolved in 80 wt % sulfuric acid (50 mL), concentrated nitric acid (7.0 g, 107.3 mM) was slowly added dropwise at −15° C., and a resulting mixture was hold at a constant temperature until a reaction was completed. After the reaction was completed, a resulting reaction system was poured into ice water and stirred continuously, such that a large amount of a yellow solid was precipitated. The resulting system was subjected to suction filtration to obtain a filter cake, and the filter cake was washed three times with a saturated sodium bicarbonate solution, and dried for subsequent use. The compound was characterized by: $^{1}H$ NMR (400 MHz, $CDCl_3$) δ 8.5 (d, J=5.0 Hz, 1H), 7.7 (d, J=8.0 Hz, 1H), δ 2.4 (p, J=3.4 Hz, 4H), 1.8 (p, J=3.3 Hz, 4H).

(3) Preparation of 2-(5-amino-4-chloro-2-fluorophenyl)-4,5,6,7-tetrahydro-1H-isoindole-1,3(2H)-dione: a Reaction Equation was as Follows

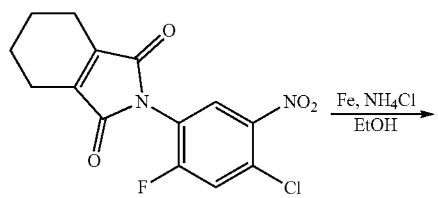

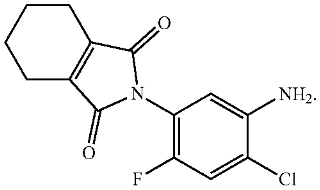

2-(4-chloro-2-fluoro-5-nitrophenyl)-4,5,6,7-tetrahydro-1H-isoindole-1,3(2H)-dione (15.0 g, 46.20 mM) was dissolved in 90 vol % ethanol, and added with ammonium chloride (12.9 g, 230.99 mM), and a resulting mixture was heated to reflux under stirring and then subjected to reaction. An iron powder (12.36 g, 230.99 mM) was slowly added and the reaction under reflux was continued. After the reaction was completed, a resulting reaction system was subjected to suction filtration to obtain a filtrate, and the filtrate was subjected to concentration and recrystallization to obtain a compound, namely the 2-(5-amino-4-chloro-2-fluorophenyl)-4,5,6,7-tetrahydro-1H-isoindole-1,3(2H)-dione. The compound was characterized by: $^{1}H$ NMR (400 MHz, $CDCl_3$) δ 7.5 (d, J=8.0 Hz, 1H), 7.2 (d, J=4.9 Hz, 1H), 4.8 (s, 2H), 2.4 (m, J=2.9 Hz, 4H), 1.9-1.3 (m, 4H).

(4) Preparation of N-(2-chloro-5-(1,3-dioxo-1,3,4,5,6,7-hexahydro-2H-isoindole-2-yl)-4-fluorophenyl)acetamide: a Reaction Equation was as Follows

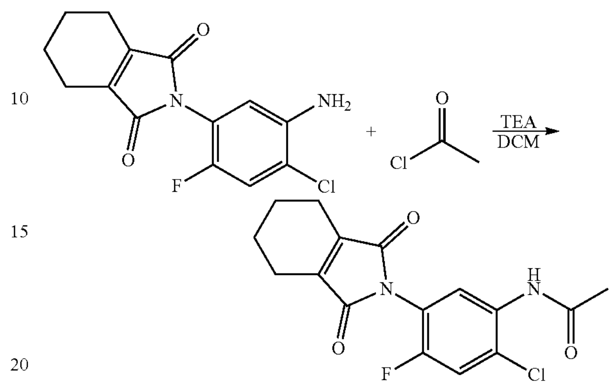

Acyl chloride (0.15 g, 1.87 mM) and triethylamine (0.18 g, 1.70 mM) as a catalyst were added into 2-(5-amino-4-chloro-2-fluorophenyl)-4,5,6,7-tetrahydro-1H-isoindole-1,3(2H)-dione (0.5 g, 1.70 mM) in dichloromethane under ice bath, and then a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.48 g, 80%).

Example 64: A Preparation Method of 2-chloro-N-(2-chloro-5-(1,3-dioxo-1,3,4,5,6,7-hexahydro-2H-isoindole-2-yl)-4-fluorophenyl)acetamide (Corresponding to Compound D2) was Performed According to the Following Procedures: a Reaction Equation was as Follows

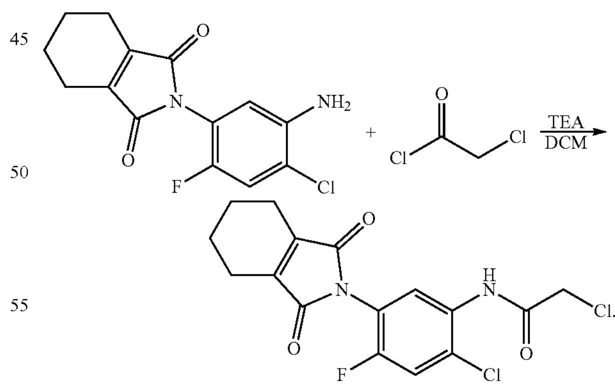

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, chloryl chloride (0.21 g, 1.87 mM) and triethylamine (0.17 g, 1.70 mM) were added, and stirred for 10 min, the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.35 g, 74%).

Example 65: A Preparation Method of 2-bromo-N-(2-chloro-5-(1,3-dioxo-1,3,4,5,6,7-hexahydro-2H-isoindol-2-yl)-4-fluorophenyl)propionamide (Corresponding to Compound D3) was Performed According to the Following Procedures: a Reaction Equation was as Follows

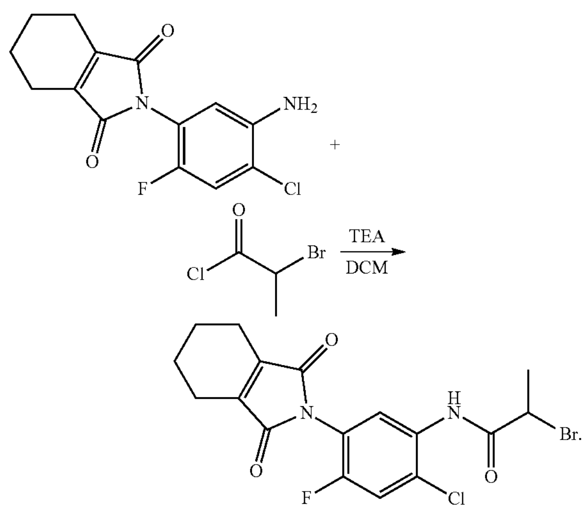

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, 2-bromopropionyl chloride (0.32 g, 1.87 mM) and triethylamine (0.08 g, 0.85 mM) were added, and stirred for 10 min, the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.33 g, 72%).

Example 66: A Preparation Method of 3-chloro-N-(2-chloro-5-(1,3-dioxo-1,3,4,5,6,7-hexahydro-2H-isoindole-2-yl)-4-fluorophenyl)-2,2-dimethylpropionamide (Corresponding to Compound D4) was Performed According to the Following Procedures: a Reaction Equation was as Follows

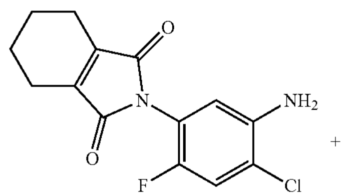

-continued

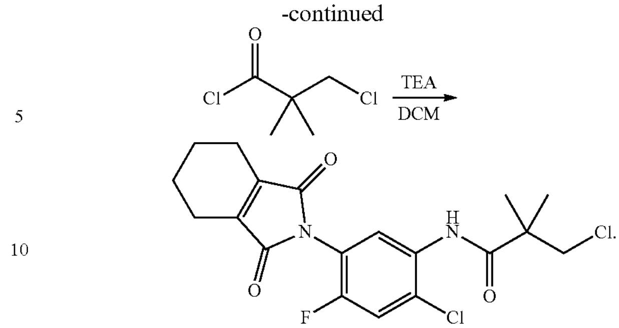

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, 3-chloro-2,2-dimethylpropionyl chloride (0.29 g, 1.87 mM) and triethylamine (0.08 g, 0.85 mM) were added, and stirred for 10 min, the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.34 g, 70%).

Example 67: A Preparation Method of (E)-N-(2-chloro-5-(1,3-dioxo-1,3,4,5,6,7-hexahydro-2H-isoindole-2-yl)-4-fluorophenyl)but-2-enamide (Corresponding to Compound D5) was Performed According to the Following Procedures: a Reaction Equation was as Follows

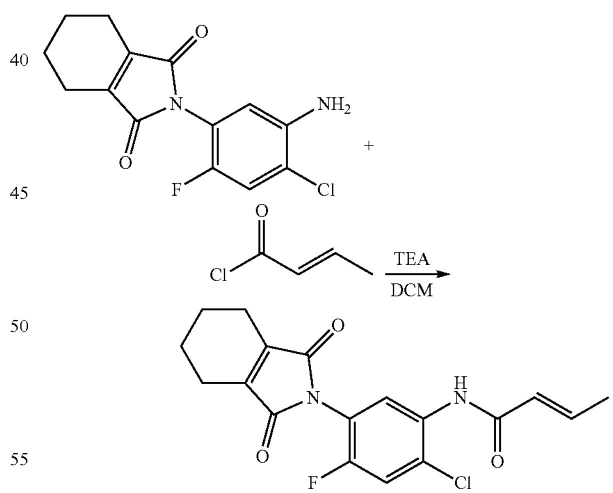

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, (E)-but-2-enoyl chloride (0.20 g, 1.87 mM) and triethylamine (0.08 g, 0.85 mM) were added, and stirred for 10 min, the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.31 g, 80%).

Example 68: A Preparation Method of 3-((2-chloro-5-(1,3-dioxo-1,3,4,5,6,7-hexahydro-2H-isoindole-2-yl)-4-fluorophenyl)amino)-ethyl 3-oxopropanoate (Corresponding to Compound D6) was Performed According to the Following Procedures: a Reaction Equation was as Follows

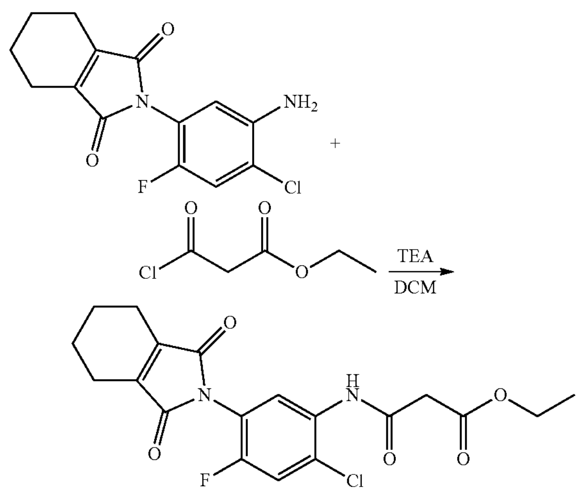

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, ethyl 3-chloro-3-oxo-propanoate (0.28 g, 1.87 mM) and triethylamine (0.08 g, 0.85 mM) were added, and stirred for 10 min, and the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.31 g, 76%).

Example 69: A Preparation Method of N-(2-chloro-5-(1,3-dioxo-1,3,4,5,6,7-hexahydro-2H-isoindole-2-yl)-4-fluorophenyl)nonanamide (Corresponding to Compound D7) was Performed According to the Following Procedures: a Reaction Equation was as Follows

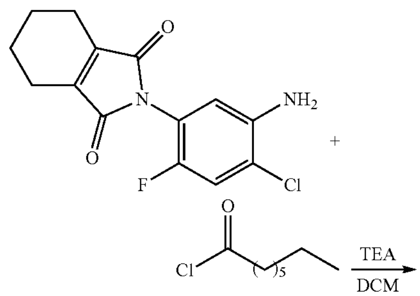

-continued

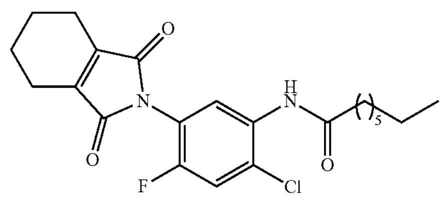

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, nonanoyl chloride (0.33 g, 1.87 mM) and triethylamine (0.08 g, 0.85 mM) were added were added, and stirred for 10 min, and the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.32 g, 74%).

Example 70: A Preparation Method of N-(2-chloro-5-(1,3-dioxo-1,3,4,5,6,7-hexahydro-2H-isoindole-2-yl)-4-fluorophenyl)cyclopropanecarboxamide (Corresponding to Compound D8) was Performed According to the Following Procedures: a Reaction Equation was as Follows

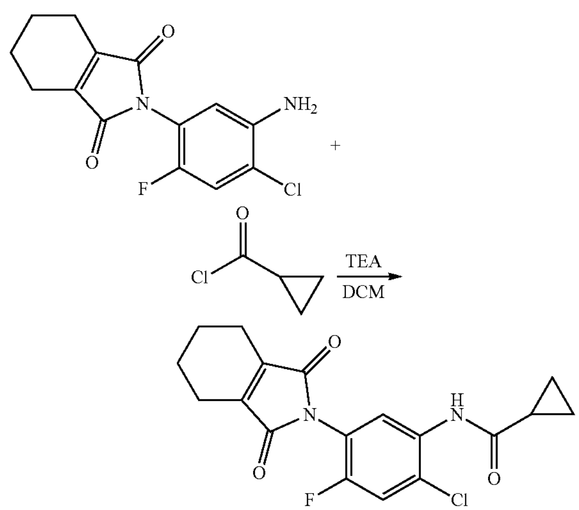

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, cyclopropanoyl chloride (0.20 g, 1.87 mM) and triethylamine (0.08 g, 0.85 mM) were added, and stirred for 10 min, the ice bath was removed, and a resulting mixture was subjected to reaction under stirring at ambient temperature. After the reaction was completed, an obtained reaction system was extracted with ethyl acetate to obtain an organic phase, and the organic phase was dried with anhydrous sodium sulfate, and purified with silica gel column chromatography to obtain a target compound (0.31 g, 71%).

Example 71: A Preparation Method of N-(2-chloro-5-(1,3-dioxo-1,3,4,5,6,7-hexahydro-2H-isoindole-2-yl)-4-fluorophenyl)cyclobutanecarboxamide (Corresponding to Compound D9) was Performed According to the Following Procedures: a Reaction Equation was as Follows

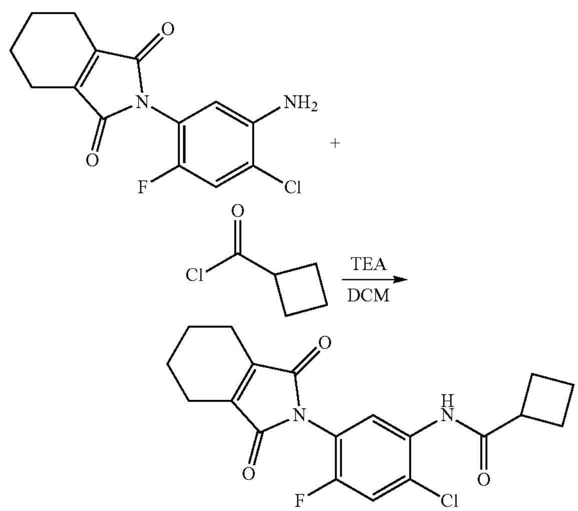

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, cyclobutyryl chloride (0.22 g, 1.87 mM) and triethylamine (0.08 g, 0.85 mM) were added, and stirred for 10 min, the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.32 g, 73%).

Example 72: A Preparation Method of N-(2-chloro-5-(1,3-dioxo-1,3,4,5,6,7-hexahydro-2H-isoindole-2-yl)-4-fluorophenyl)cyclohexanecarboxamide (Corresponding to Compound D10) was Performed According to the Following Procedures: a Reaction Equation was as Follows

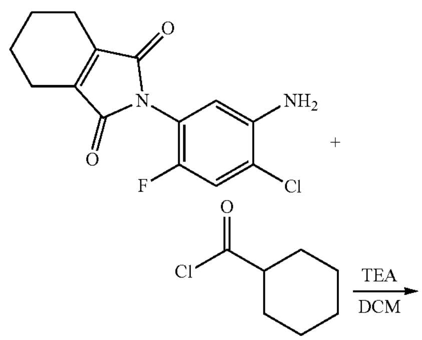

-continued

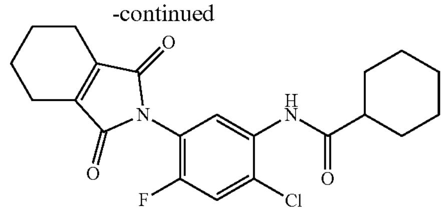

2-(5-amino-4-chloro-2-fluorophenyl)-4,5,6,7-tetrahydro-1H-isoindole-1,3(2H)-dione (0.5 g, 1.70 mM) was dissolved in dichloromethane. Under ice bath, cyclohexanoyl chloride (0.27 g, 1.87 mM) and triethylamine (0.08 g, 0.85 mM) were added, and stirred for 10 min, the ice bath was removed, and a resulting mixture was subjected to reaction under stirring at ambient temperature. After the reaction was completed, an obtained reaction system was extracted with dichloromethane to obtain an organic phase, and the organic phase was dried with anhydrous sodium sulfate, and purified with silica gel column chromatography to obtain a target compound (0.32 g, 75%).

Example 73: A Preparation Method of 2-(4-chlorophenyl)-2-oxoethyl-2-chloro-5-(1,3-dioxo-1,3,4,5,6,7-hexahydro-2H-isoindole-2-yl)-4-fluorobenzoate (Corresponding to Compound E1) was Performed According to the Following Procedures (1) Preparation of 2-(4-chlorophenyl)-2-oxoethyl-2-chloro-4-fluoro-5-nitrobenzoate: a Reaction Equation was as Follows

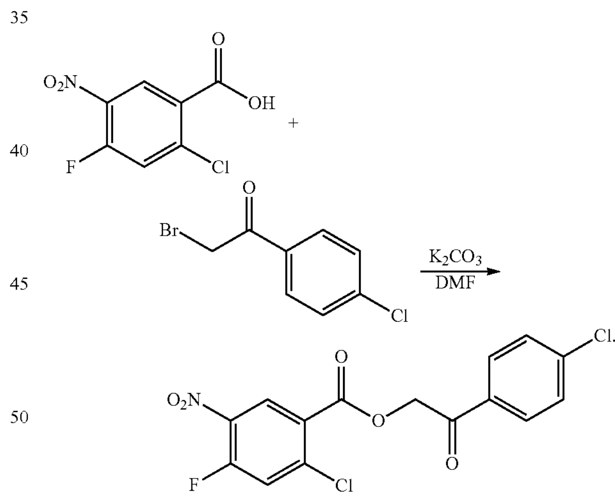

2-chloro-4-fluoro-5-nitrobenzoic acid (1.0 g, 4.55 mM) was dissolved in 15 mL of DMF, then added with potassium carbonate (1.89 g, 13.66 mM), and stirred at ambient temperature for 10 min, and 2-bromo-1-(4-chlorophenyl)ethan-1-one (1.06 g, 4.55 mM) was added to conduct reaction. After the reaction was completed, an obtained reaction system was subjected to suction filtration to remove potassium carbonate, followed by extraction with ethyl acetate, concentration, and purification with silica gel column chromatography to obtain a white solid (1.26 g, 80%). The compound was characterized by: $^1$H NMR (400 MHz, $CDCl_3$) δ 8.5 (d, J=4.9 Hz, 1H), 8.1 (dd, J=8.6, 5.0 Hz, 2H), 7.7 (d, J=7.9 Hz, 1H), 7.3 (t, J=8.3 Hz, 2H), 5.7 (s, 2H).

(2) Preparation of 2-(4-chlorophenyl)-2-oxoethyl-5-amino-2-chloro-4-fluorobenzoate: a Reaction Equation was as Follows

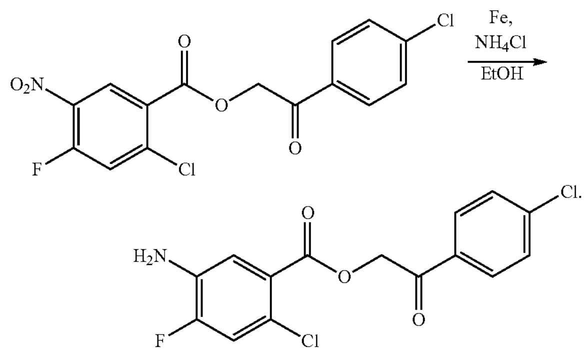

2-(4-chlorophenyl)-2-oxoethyl-2-chloro-4-fluoro-5-nitrobenzoate (1.0 g, 2.69 mM) was dissolved in 15 mL of 90% ethanol, then added with ammonium chloride (0.75 g, 13.44 mM), and heated under stirring and then subjected to reaction under reflux. Then an iron powder (0.72 g, 13.44 mM) was slowly added thereto and the reaction under reflux was continued. After the reaction was completed, a resulting reaction system was subjected to suction filtration to obtain a filtrate, and the filtrate was concentrated to obtain a solid, and the solid was recrystallized to obtain a product. The compound was characterized by: $^1$H NMR (400 MHz, $CDCl_3$) δ 8.1 (dd, J=8.6, 5.0 Hz, 2H), 7.5 (d, J=7.9 Hz, 1H), 7.4 (d, J=4.9 Hz, 1H), 7.3 (t, J=8.3 Hz, 2H), 5.7 (s, 2H), 4.5 (s, 2H).

(3) Preparation of 2-(4-chlorophenyl)-2-oxoethyl-2-chloro-5-(1,3-dioxo-1,3,4,5,6,7-hexahydro-2H-isoindole-2-yl)-4-fluorobenzoate: a Reaction Equation was as Follows

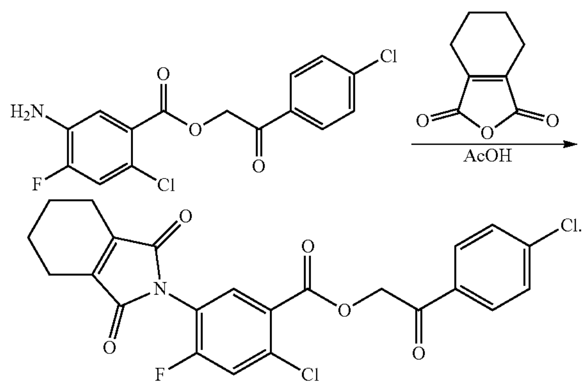

2-(4-chlorophenyl)-2-oxoethyl-5-amino-2-chloro-4-fluorobenzoate (0.50 g, 1.46 mM) was dissolved in 15 ml of glacial acetic acid, and added with 4,5,6,7-tetrahydroisobenzofuran-1,3-dione (0.22 g, 1.46 mM) under stirring, and a resulting mixture was heated and then subjected to reaction under reflux. After the reaction was completed, an obtained reaction system was extracted with ethyl acetate to obtain an organic phase, and the organic phase was dried, concentrated, and purified with silica gel column chromatography to obtain a target compound (0.56 g, 81%).

Example 74: A Preparation Method of 2-oxo-2-phenylethyl-2-chloro-5-(1,3-dioxo-1,3,4,5,6,7-hexahydro-2H-isoindole-2-yl)-4-fluorobenzoate (Corresponding to Compound E2) was Performed According to the Following Procedures: a Reaction Equation was as Follows

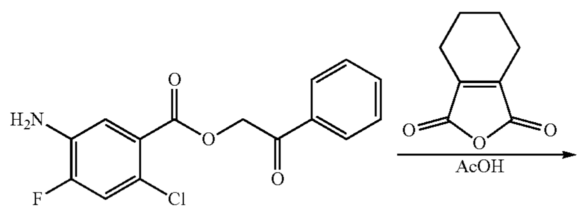

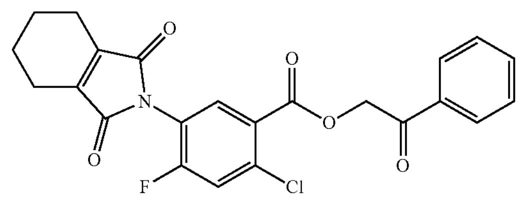

2-phenyl-2-oxoethyl-5-amino-2-chloro-4-fluorobenzoate (0.50 g, 1.62 mM) was dissolved in 15 mL of glacial acetic acid, and added with 4,5,6,7-tetrahydroisobenzofuran-1,3-dione (0.25 g, 1.62 mM) under stirring, and a resulting mixture was heated and then subjected to reaction under reflux. After the reaction was completed, an obtained reaction system was extracted with ethyl acetate to obtain an organic phase, and the organic phase was dried, concentrated, and purified with silica gel column chromatography to obtain a target compound (0.54 g, 78%).

The physicochemical properties and spectrogram data of the target compounds obtained in the above examples were shown in Table 1:

TABLE 1

Physicochemical properties and spectral data of the target compounds prepared in Examples 1 to 74

| SN | State | Melting point (° C.) | $^1$H NMR, $^{13}$C NMR |
| --- | --- | --- | --- |
| A1 | White solid | 101-105 | $^1$H NMR (500 MHz, $CDCl_3$) δ 8.14 (d, J = 2.2 Hz, 1H), 7.47 (dd, J = 8.2, 2.2 Hz, 1H), 7.30 (d, J = 9.0 Hz, 1H), 7.16 (d, J = 8.2 Hz, 1H), 7.03 (d, J = 6.3 |

TABLE 1-continued

Physicochemical properties and spectral data of the target compounds prepared in Examples 1 to 74

| SN | State | Melting point (° C.) | $^1$H NMR, $^{13}$C NMR |
|---|---|---|---|
| | | | Hz, 1H), 5.37 (s, 2H), 2.54 (s, 3H), 2.40 (t, J = 3.0 Hz, 4H), 1.79 (t, J = 3.0 Hz, 4H). $^{13}$C NMR (126 MHz, $CDCl_3$) δ 173.1, 168.6, 168.2, 152.9 (d, J = 252.0 Hz), 149.8 (d, J = 3.0 Hz), 142.7, 137.5, 133.8, 133.2, 132.9, 127.4, 125.0 (d, J = 9.5 Hz), 119.6, 118.9 (d, J = 24.6 Hz), 118.6 (d, J = 14.8 Hz), 116.2, 63.0, 21.9, 21.3, 20.4. |
| A2 | White solid | 161-167 | $^1$H NMR (500 MHz, $CDCl_3$) δ 7.9 (d, J = 8.4 Hz, 1H), 7.5 (d, J = 2.1 Hz, 1H), 7.4 (d, J = 2.1 Hz, 1H), 7.4 (d, J = 2.1 Hz, 1H), 7.3 (d, J = 8.9 Hz, 1H), 5.4 (s, 2H), 2.4 (t, J = 2.9 Hz, 7H), 1.8 (t, J = 2.6 Hz, 4H). $^{13}$C NMR (126 MHz, $CDCl_3$) δ 173.5, 168.7, 166.9, 152.9 (d, J = 252.0 Hz), 142.7, 137.7, 134.4, 132.8, 131.0, 127.6, 125.2 (d, J = 9.5 Hz), 124.1, 119.0 (d, J = 24.6 Hz), 118.6 (d, J = 14.8 Hz), 116.4, 63.0, 21.3, 20.4. |
| A3 | White powder | 122-125 | $^1$H NMR (500 MHz, $CDCl_3$) δ 8.1 (ddd, J = 2.1, 1.5, 0.5 Hz, 1H), 8.0 (dt, J = 7.7, 1.4 Hz, 1H), 7.5 (ddd, J = 8.1, 2.1, 1.1 Hz, 1H), 7.4-7.4 (m, 1H). 7.3 (d, J = 8.9 Hz, 1H), 7.0 (d, J = 6.3 Hz, 1H), 5.4 (s, 2H), 2.4 (t, J = 3.0 Hz, 4H), 1.8 (t, J = 2.5 Hz, 4H). $^{13}$C NMR (126 MHz, $CDCl_3$) δ 174.1, 168.6, 167.8, 153.0(d, J = 252.0 Hz), 149.8 (d, J = 3.0 Hz), 142.7, 135.1, 131.7, 130.4, 128.0, 127.8, 125.8, 125.1 (d, J = 9.5 Hz), 119.0 (d, J = 24.4 Hz), 118.6 (d, J = 14.8 Hz), 116.3, 63.1, 21.3, 20.4. |
| A4 | White solid | 131-133 | $^1$H NMR (500 MHz, $CDCl_3$) δ 7.8 (dd, J = 7.7, 1.8 Hz, 1H), 7.7 (dd, J = 8.0, 1.2 Hz, 1H), 7.4 (td, J = 7.6, 1.2 Hz, 1H), 7.3 (ddd, J = 8.0, 7.5, 1.8 Hz, 1H), 7.3 (d, J = 9.0 Hz, 1H), 7.0 (d, J = 6.3 Hz, 1H), 5.4 (s, 2H), 2.4 (t, J = 2.7 Hz, 4H), 1.8 (t, J = 2.7 Hz, 4H). $^{13}$C NMR (126 MHz, $CDCl_3$) δ 173.5, 168.7, 168.3, 153.0(d, J = 252.0 Hz), 149.9 (d, J = 3.1 Hz), 142.7, 134.3, 132.2 (d, J = 4.6 Hz), 127.6 (d, J = 3.7 Hz), 125.2 (d, J = 9.6 Hz), 122.3, 119.0 (d, J = 24.5 Hz), 118.6 (d, J = 14.8 Hz), 116.4, 63.1, 21.3, 20.4. |
| A5 | White solid | 147-150 | $^1$H NMR (500 MHz, $CDCl_3$) δ 8.1-8.0 (m, 2H), 7.5-7.4 (m, 2H), 7.3 (d, J = 9.0 Hz, 1H), 7.0 (d, J = 6.3 Hz, 1H), 5.4 (s, 2H), 2.4 (t, J = 2.7 Hz, 4H), 2.1-1.2 (m, 4H). $^{13}$C NMR (126 MHz, $CDCl_3$) δ 173.8, 168.8, 168.7, 153.0(d, J = 252.0 Hz), 149.9 (d, J = 3.0 Hz), 142.7, 131.6, 129.0, 127.7, 126.3, 125.2 (d, J = 9.5 Hz), 118.9 (d, J = 24.5 Hz), 118.5 (d, J = 14.7 Hz), 116.2, 63.2, 21.3, 20.4 |
| A6 | Yellow oil | — | — |
| A7 | White solid | 109-112 | $^1$H NMR (500 MHz, $CDCl_3$) δ 8.0 (ddd, J = 8.9, 8.1, 6.5 Hz, 1H), 7.3 (d, J = 9.0 Hz, 1H), 7.0 (ddd, J = 9.3, 7.5, 2.4 Hz, 1H), 6.9 (ddd, J = 11.0, 8.5, 2.4 Hz, 1H), 6.7 (d, J = 6.3 Hz, 1H), 5.2 (d, J = 3.4 Hz, 2H), 2.4 (t, J = 3.0 Hz, 4H), 1.9-1.7 (m, 4H). $^{13}$C NMR (126 MHz, $CDCl_3$) δ 190.4, 190.3, 168.7, 166.6 (d, J = 246.9 Hz), 163.1 (d, J = 244.4 Hz), 152.4(d, J = 250.7 Hz), 150.4 (d, J = 2.9 Hz), 142.6, 133.1 (dd, J = 10.9, 4.8 Hz), 124.6 (d, J = 9.7 Hz), 119.3 (d, J = 11.9 Hz), 118.7 (d, J = 24.4 Hz), 118.3 (d, J = 14.6 Hz), 115.4, 113.0 (dd, J = 21.6, 3.2 Hz), 105.7-103.9 (m), 75.1 (d, J = 12.5 Hz), 21.3, 20.3 |
| A8 | White solid | 126-131 | $^1$H NMR (500 MHz, $CDCl_3$) δ 7.9 (dd, J = 7.8, 1.8 Hz, 1H), 7.5 (dd, J = 7.9, 1.3 Hz, 1H), 7.4 (td, J = 7.7, 1.8 Hz, 1H), 7.4 (td, J = 7.4, 1.4 Hz, 1H), 7.3 (d, J = 9.0 Hz, 1H), 7.0 (d, J = 6.4 Hz, 1H), 5.4 (s, 2H), 2.4 (h, J = 2.7, 2.1 Hz, 4H), 1.8 (q, J = 3.1 Hz, 4H). $^{13}$C NMR (126 MHz, $CDCl_3$) δ 173.4, 168.6, 167.6, 152.4(d, J = 250.7 Hz), 149.9 (d, J = 3.0 Hz), 142.7, 133.6, 132.0 (d, J = 8.3 Hz), 131.1, 127.1, 125.6, 125.2 (d, J = 9.7 Hz), 119.0 (d, J = 24.5 Hz), 118.6 (d, J = 14.9 Hz), 116.5, 63.1, 21.3, 20.4. |
| A9 | White powder | 153-155 | $^1$H NMR (500 MHz, $CDCl_3$) δ 7.8 (dd, J = 7.8, 1.7 Hz, 1H), 7.7 (dd, J = 10.1, 1.7 Hz, 1H), 7.3-7.3 (m, 1H), 7.3 (dd, J = 7.8, 0.9 Hz, 1H), 7.0 (d, J = 6.3 Hz, 1H), 5.4 (s, 2H), 2.4 (p, J = 3.1 Hz, 4H), 2.3 (d, J = 1.9 Hz, 3H), 1.8 (m, J = 6.1, 3.3, 2.9 Hz, 4H). $^{13}$C NMR (126 MHz, $CDCl_3$) δ 173.9, 168.7, 168.0 (d, J = 2.9 Hz), 161.4(d, J = 252.0 Hz), 153.0(d, J = 250.0 Hz), 149.9 (d, J = 2.9 Hz), 142.7, 132.1 (d, J = 5.3 Hz), 128.9 (d, J = 17.2 Hz), 125.6 (d, J = 8.5 Hz), 125.1 (d, J = 9.5 Hz), 123.1 (d, J = 3.4 Hz), 119.0 (d, J = 24.5 Hz), 118.6 (d, J = 14.8 Hz), 116.3, 114.3 (d, J = 24.8 Hz), 63.1, 21.3, 20.4, 14.9 (d, J = 3.5 Hz). |
| A10 | Gray solid | 165-167 | $^1$H NMR (500 MHz, $CDCl_3$) δ 9.0-8.8 (m, 1H), 8.1 (d, J = 2.0 Hz, 1H), 7.3 (d, J = 9.0 Hz, 1H), 7.0 (d, J = 6.3 Hz, 1H), 5.4 (s, 2H), 2.4 (t, J = 2.7 Hz, 4H), 2.1-1.5 (m, 4H). $^{13}$C NMR (126 MHz, $CDCl_3$) δ 174.4, 168.6, 166.3, 153.0(d, J = 250.0 Hz), 149.7 (d, J = 2.9 Hz), 146.8, 145.9-143.7 (m), 142.7, 137.7-134.9 (m), 132.7, 129.9-128.1 (m), 125.3 (d, J = 9.6 Hz), 123.3, 121.1, 119.0 (d, J = 24.6 Hz), 118.6 (d, J = 14.8 Hz), 116.3, 63.1, 21.3, 20.4. |
| A11 | Yellow powder | 117-122 | $^1$H NMR (500 MHz, $CDCl_3$) δ 8.2 (d, J = 1.8 Hz, 1H), 7.8 (t, J = 1.8 Hz, 1H), 7.3 (d, J = 8.9 Hz, 1H), 7.0 (d, J = 6.3 Hz, 1H), 5.4 (s, 1H), 2.4 (p, J = 3.2 Hz, 4H), 1.8 (p, J = 3.3 Hz, 4H). $^{13}$C NMR (126 MHz, $CDCl_3$) δ 174.4, 168.6, 166.7, 153.0(d, J = 250.0 Hz), 149.7 (d, J = 2.9 Hz), 142.7, 137.0, 129.5, 129.4, 125.1 (d, J = 9.6 Hz), 123.6, 119.0 (d, J = 24.6 Hz), 118.6 (d, J = 14.8 Hz), 116.4, 63.0, 21.3, 20.4. |
| A12 | White solid | 175-177 | $^1$H NMR (500 MHz, $CDCl_3$) δ 8.1 (ddd, J = 7.8, 7.1, 1.8 Hz, 1H), 7.5-7.4 (m, 1H). 7.3-7.2 (m, 3H), 7.0 (d, J = 6.3 Hz, 1H), 5.4 (s, 2H), 2.4 (p, J = 3.2 Hz, 4H), 1.8 (m, J = 6.2, 3.5, 2.9 Hz, 4H). $^{13}$C NMR (126 MHz, $CDCl_3$) δ 173.5, 168.6, 165.6, 160.8(d, J = 252.0 Hz), 153.0(d, J = 252.0 Hz), 149.9, |

TABLE 1-continued

Physicochemical properties and spectral data of the target compounds prepared in Examples 1 to 74

| SN | State | Melting point (° C.) | $^{1}H$ NMR, $^{13}C$ NMR |
|---|---|---|---|
| | | | 142.6, 133.2 (d, J = 8.5 Hz), 131.0, 125.2 (d, J = 9.6 Hz), 124.6 (d, J = 3.8 Hz), 118.9 (d, J = 24.6 Hz), 118.6 (d, J = 15.2 Hz), 116.8 (d, J = 21.1 Hz), 116.4, 114.6 (d, J = 11.9 Hz), 63.1, 21.3, 20.3. |
| A13 | White solid | 120-125 | $^{1}H$ NMR (500 MHz, $CDCl_3$) δ 8.0 (t, J = 1.7 Hz, 1H), 7.8-7.7 (m, 1H), 7.4 (m, J = 7.9, 2.1 Hz, 1H), 7.3 (d, J = 8.9 Hz, 1H), 7.0 (d, J = 6.2 Hz, 1H), 5.4 (s, 2H), 2.4 (t, J = 3.0 Hz, 4H), 1.8 (t, J = 2.9 Hz, 4H). $^{13}C$ NMR (126 MHz, $CDCl_3$) δ 174.4, 168.6, 166.9 (d, J = 3.3 Hz), 162.7(d, J = 252 Hz), 153.0(d, J = 252.0 Hz), 149.7 (d, J = 3.0 Hz), 142.7, 129.5 (d, J = 9.2 Hz), 126.7 (d, J = 3.4 Hz), 125.1 (d, J = 9.5 Hz), 123.4 (d, J = 9.6 Hz), 122.1 (d, J = 24.4 Hz), 119.0 (d, J = 24.5 Hz), 118.6 (d, J = 14.7 Hz), 116.4, 113.7 (d, J = 23.7 Hz), 63.0, 21.3, 20.4 |
| A14 | White solid | 147-150 | $^{1}H$ NMR (500 MHz, $CDCl_3$) δ 7.9 (dd, J = 10.8, 7.6, 2.1 Hz, 1H), 7.9-7.8 (m, 1H), 7.3-7.2 (m, 2H), 7.0 (d, J = 6.2 Hz, 1H), 5.4 (s, 2H), 2.4 (t, J = 3.0 Hz, 4H), 1.8 (t, J = 2.7 Hz, 4H). $^{13}C$ NMR (126 MHz, $CDCl_3$) δ 174.2, 168.7, 167.3, 153.6 (d, J = 12.6 Hz), 153.0(d, J = 252.0 Hz), 151.6 (t, J = 12.5 Hz). 150.4-149.0 (m), 142.7, 125.1 (d, J = 9.6 Hz), 124.4 (dd, J = 7.0, 3.9 Hz), 123.3 (d, J = 6.8 Hz), 119.0 (d, J = 24.6 Hz), 118.6 (d, J = 14.8 Hz), 118.2 (d, J = 18.0 Hz), 117.1 (d, J = 19.3 Hz), 116.4, 63.0, 21.3, 20.4. |
| A15 | White solid | 117-121 | $^{1}H$ NMR (400 MHz, $CDCl_3$) δ 7.9 (d, J = 1.8 Hz, 1H), 7.9 (dd, J = 7.5, 1.7 Hz, 1H), 7.4 (t, J = 7.6 Hz, 1H), 7.4-7.3 (m, 2H), 7.0 (d, J = 6.3 Hz, 1H), 5.4 (s, 2H), 2.4 (d, J = 2.8 Hz, 7H), 1.8 (q, J = 3.0 Hz, 4H). $^{13}C$ NMR (126 MHz, $CDCl_3$) δ 173.7, 168.9, 168.7, 153.0(d, J = 252.0 Hz), 149.9 (d, J = 3.0 Hz), 142.6, 138.9, 132.4, 128.9, 128.3, 126.1, 125.1 (d, J = 9.6 Hz), 124.8, 118.9 (d, J = 24.4 Hz), 118.6 (d, J = 14.8 Hz), 116.3, 63.2, 21.4, 21.3, 20.4. |
| A16 | White solid | 169-175 | $^{1}H$ NMR (400 MHz, $CDCl_3$) δ 8.2 (d, J = 8.1 Hz, 1H), 7.4 (d, J = 8.1 Hz, 1H), 7.3 (d, J = 9.0 Hz, 1H), 7.0 (d, J = 6.3 Hz, 1H), 5.3 (s, 2H), 2.4 (t, J = 3.1 Hz, 4H), 1.8-1.7 (m, 4H). $^{13}C$ NMR (126 MHz, $CDCl_3$) δ 167.4, 162.0, 159.0, 146.4(d, J = 252.0 Hz), 145.8, 143.0 (d, J = 3.0 Hz), 142.6, 136.0 (d, J = 3.7 Hz), 118.5 (d, J = 9.6 Hz), 116.6, 114.9, 112.3 (d, J = 24.5 Hz), 111.9 (d, J = 14.8 Hz), 109.9, 56.3, 14.6, 13.7. |
| A17 | White solid | 193-200 | $^{1}H$ NMR (500 MHz, $CDCl_3$) δ 9.1-9.0 (m, 1H), 8.3 (dt, J = 8.2, 0.8 Hz, 1H), 8.2-8.1 (m, 1H), 7.3 (d, J = 8.9 Hz, 1H), 7.0 (d, J = 6.3 Hz, 1H), 5.4 (s, 2H), 2.4 (p, J = 3.4 Hz, 4H), 1.8 (p, J = 3.3 Hz, 4H). $^{13}C$ NMR (126 MHz, $CDCl_3$) δ 175.1, 168,6, 167.7, 153.1 (d, J = 252.0 Hz), 149.7, 149.0, 147.4 (d, J = 4.3 Hz), 142.7, 134.9, 134.7 (d, J = 3.8 Hz), 128.5 (d, J = 33.3 Hz), 125.2 (d, J = 9.6 Hz), 124.2, 123.3, 122.0, 119.0 (d, J = 24.5 Hz), 118.6 (d, J = 14.7 Hz), 116.2, 63.0, 21.3, 20.4. |
| A18 | White solid | 111-116 | $^{1}H$ NMR (500 MHz, $CDCl_3$) δ 8.4-8.3 (m, 1H), 8.3 (dd, J = 7.9, 1.5 Hz, 1H), 7.8 (dd, J = 7.8, 1.9, 0.9 Hz, 1H), 7.6 (t, J = 7.8 Hz, 1H), 7.3 (d, J = 9.0 Hz, 1H), 7.0 (d, J = 6.3 Hz, 1H), 5.4 (s, 2H), 2.4 (t, J = 3.0 Hz, 4H), 1.8 (p, J = 3.1 Hz, 4H). $^{13}C$ NMR (126 MHz, $CDCl_3$) δ 174.3, 168.6, 167.8, 154.0, 152.0, 149.8 (d, J = 3.1 Hz), 142.7, 131.6 (q, J = 33.0 Hz), 130.8, 129.6, 128.2 (q, J = 3.8 Hz), 127.0, 125.1 (d, J = 9.6 Hz), 124.8-124.4 (m), 123.8(d, J = 554.4 Hz), 119.0 (d, J = 24.5 Hz), 118.6 (d, J = 14.6 Hz), 116.4, 63.0, 21.3, 20.3. |
| A19 | White solid | 128-136 | $^{1}H$ NMR (400 MHz, $CDCl_3$) δ 7.8 (dd, J = 3.7, 1.2 Hz, 1H), 7.5 (dd, J = 5.1, 1.2 Hz, 1H), 7.3 (d, J = 9.0 Hz, 1H), 7.2 (dd, J = 5.0, 3.7 Hz, 1H), 7.0 (d, J = 6.3 Hz, 1H), 5.4 (s, 2H), 2.8-2.3 (m, 4H), 2.1-1.4 (m, 4H). $^{13}C$ NMR (126 MHz, $CDCl_3$) δ 167.1, 161.9, 158.1, 146.3(d, J = 252.0 Hz), 143.2 (d, J = 3.0 Hz), 135.9, 123.6, 123.2, 121.5, 120.9, 118.4 (d, J = 9.6 Hz), 112.2 (d, J = 24.4 Hz), 111.9 (d, J = 14.9 Hz), 109.6, 56.4, 14.6, 13.7. |
| A20 | White solid | 132-138 | $^{1}H$ NMR (500 MHz, $CDCl_3$) δ 8.1 (d, J = 8.9 Hz, 1H), 7.3 (dd, J = 8.9, 1.5 Hz, 2H), 7.0 (d, J = 6.3 Hz, 1H), 5.4 (s, 2H), 2.4 (p, J = 3.3 Hz, 4H), 1.8 (dq, J = 6.2, 3.3, 2.8 Hz, 4H). $^{13}C$ NMR (126 MHz, $CDCl_3$) δ 174.1, 168.7, 167.8, 154.0, 152.0, 151.6, 149.8 (d, J = 3.1 Hz), 142.7, 129.5, 125.2 (d, J = 9.6 Hz), 124.9, 121.5, 120.7(d, J = 544.4 Hz), 119.0 (d, J = 24.5 Hz), 118.6 (d, J = 14.7 Hz), 116.3, 63.1, 21.3, 20.4. |
| A21 | White solid | 104-110 | $^{1}H$ NMR (400 MHz, $CDCl_3$) δ 7.7 (dd, J = 8.9, 3.1 Hz, 1H), 7.5 (dd, J = 8.9, 5.0 Hz, 1H), 7.3 (d, J = 9.0 Hz, 1H), 7.2 (ddd, J = 8.9, 7.5, 3.1 Hz, 1H), 7.1 (d, J = 6.3 Hz, 1H), 5.4 (s, 2H), 2.4 (q, J = 2.3, 1.7 Hz, 4H), 1.8 (t, J = 2.6 Hz, 4H). $^{13}C$ NMR (126 MHz, $CDCl_3$) δ 167.0, 162.0, 160.0 (d, J = 2.3 Hz), 154.3(d, J = 239.4 Hz), 146.3(d, J = 252.0 Hz), 143.1 (d, J = 3.0 Hz), 136.0, 125.9 (d, J = 8.1 Hz), 122.0 (d, J = 3.5 Hz), 120.3 (d, J = 8.5 Hz), 118.4 (d, J = 9.6 Hz), 112.6 (d, J = 22.8 Hz), 112.4 (d, J = 4.8 Hz), 112.2 (d, J = 5.7 Hz), 111.9 (d, J = 14.6 Hz), 109.7, 56.3, 14.6, 13.7. |
| A22 | White solid | 150-156 | $^{1}H$ NMR (400 MHz, $CDCl_3$) δ 7.6 (dd, J = 1.8, 0.8 Hz, 1H), 7.3 (d, J = 9.0 Hz, 1H), 7.2 (dd, J = 3.5, 0.8 Hz, 1H), 7.0 (d, J = 6.3 Hz, 1H), 6.6 (dd, J = 3.5, 1.8 Hz, 1H), 5.4 (s, 2H), 2.4 (t, J = 3.1 Hz, 4H), 1.8-1.8 (m, 4H). $^{13}C$ NMR (126 MHz, $CDCl_3$) δ 167.2, 162.0, 154.9, 146.3(d, J = 252.0 Hz), 143.1 (d, J = 3.1 Hz), 139.0, 136.0, 135.0, 122.0, 118.5 (d, J = 9.6 Hz), 112.3 (d, J = 24.6 Hz), 111.9 (d, J = 14.9 Hz), 109.6, 108.0, 105.4, 56.3, 14.6, 13.7. |
| A23 | White solid | 146-153 | $^{1}H$ NMR (500 MHz, $CDCl_3$) δ 7.8 (d, J = 1.8 Hz, 1H), 7.8 (dd, J = 7.7, 1.9 Hz, 1H), 7.3 (d, J = 9.0 Hz, 1H), 7.3-7.2 (m, 1H), 7.0 (d, J = 6.2 Hz, 1H), 5.3 (s, 2H), 2.4 (p, J = 3.2 Hz, 4H), 2.3 (d, J = 4.2 Hz, 6H), 1.8 (p, J = 3.2 Hz, 4H). |

TABLE 1-continued

Physicochemical properties and spectral data of the target compounds prepared in Examples 1 to 74

| SN | State | Melting point (° C.) | $^1$H NMR, $^{13}$C NMR |
|---|---|---|---|
| A24 | White solid | 131-136 | $^1$H NMR (400 MHz, $CDCl_3$) δ 7.5 (tt, J = 8.5, 6.2 Hz, 1H), 7.3 (d, J = 9.0 Hz, 1H), 7.1-7.0 (m, 3H), 5.4 (s, 2H), 2.4 (h, J = 2.5, 2.0 Hz, 4H), 1.9-1.8 (m, 4H). $^{13}$C NMR (126 MHz, $CDCl_3$) δ 167.4, 162.0, 155.4 (d, J = 5.8 Hz), 154.7 (t, J = 2.9 Hz), 153.3 (d, J = 5.7 Hz), 146.4(d, J = 252.0 Hz), 143.2 (d, J = 3.1 Hz), 136.0, 126.5 (t, J = 10.4 Hz), 118.6 (d, J = 9.6 Hz), 112.3 (d, J = 24.6 Hz), 111.9 (d, J = 14.8 Hz), 109.8, 105.7 (d, J = 4.1 Hz), 105.5 (d, J = 4.0 Hz), 98.5 (t, J = 17.1 Hz), 56.5, 14.6, 13.7. |
| A25 | White solid | 163-170 | $^1$H NMR (500 MHz, $CDCl_3$) δ 8.0 (dd, J = 8.5, 6.0 Hz, 1H), 7.3 (d, J = 9.0 Hz, 1H), 7.0-6.9 (m, 3H), 5.4 (s, 2H), 2.6 (s, 3H), 2.4 (h, J = 2.7 Hz, 4H), 1.8 (p, J = 3.2 Hz, 4H), $^{13}$C NMR (126 MHz, $CDCl_3$) δ 172.8, 168.7, 168.6, 164.1(d, J = 252.0 Hz), 153.0(d, J = 252.0 Hz), 149.9 (d, J = 3.1 Hz), 142.7, 141.6 (d, J = 8.5 Hz), 132.6 (d, J = 9.1 Hz), 125.1 (d, J = 9.6 Hz), 121.8 (d, J = 3.0 Hz), 119.0 (d, J = 24.7 Hz), 118.5 (d, J = 14.7 Hz), 118.3 (d, J = 21.6 Hz), 116.2, 113.3 (d, J = 21.6 Hz), 63.1, 22.4, 21.3, 20.4. |
| A26 | White solid | 181-185 | $^1$H NMR (400 MHz, $CDCl_3$) δ 8.0-8.0 (m, 1H), 7.5 (d, J = 8.5 Hz, 1H), 7.3 (d, J = 9.0 Hz, 1H), 7.0 (d, J = 6.3 Hz, 1H), 5.4 (s, 1H), 2.4 (t, J = 3.1 Hz, 4H), 1.8 (d, J = 3.1 Hz, 4H), 1.4 (s, 9H). $^{13}$C NMR (126 MHz, $CDCl_3$) δ 167.0, 162.0 (d, J = 3.1 Hz), 147.9(d, J = 138.6 Hz), 145.3, 143.3 (d, J = 3.0 Hz), 136.0, 120.8, 119.3, 118.5 (d, J = 9.6 Hz), 116.7, 112.2 (d, J = 24.5 Hz), 111.9 (d, J = 14.8 Hz), 109.6, 56.6, 28.4, 24.6, 14.6, 13.7. |
| A27 | White solid | 131-134 | $^1$H NMR (500 MHz, $CDCl_3$) δ 7.9 (d, J = 8.1 Hz, 1H), 7.8 (d, J = 8.2 Hz, 1H), 7.4 (d, J = 7.9 Hz, 1H), 7.2 (d, J = 5.0 Hz, 1H), 5.3 (s, 1H), δ 2.4 (p, J = 3.4 Hz, 4H), 1.8 (p, J = 3.3 Hz, 4H)$^{13}$C NMR (126 MHz, $CDCl_3$) δ 172.9, 168.6, 167.8, 155.5(d, J = 252.0 Hz), 154.7 (d, J = 3.1 Hz), 154.2, 139.1 (d, J = 8.1 Hz), 130.4 (d, J = 20.0 Hz), 129.8, 125.1, 121.8 (d, J = 7.9 Hz), 120.7 (d, J = 20.0 Hz), 108.4 (d, J = 7.9 Hz), 96.7, 63.1, 21.3, 20.4. |
| B1 | Pale yellow solid | 211-218 | $^1$H NMR (500 MHz, $CDCl_3$) δ 7.9 (m, J = 9.7, Hz, 1H), 7.6 (dt, J = 8.0, 2.2 Hz, 1H), 7.5 (m, J = 9.8, 7.8, 4.9 Hz, 1H), 7.4 (d, J = 7.9 Hz, 1H), 7.2 (d, J = 5.0 Hz, 1H), 7.1 (m, J = 7.8, 2.2, 1.1 Hz, 1H), 5.4 (s, 2H), 2.4 (m, J = 5.9, 4.5, 3.1, 1.7 Hz, 4H), 1.8 (m, J = 3.1, 4H). $^{13}$C NMR (101 MHz, $CDCl_3$) δ 166.2, 166.1, 163.9 (d, J = 3.1 Hz), 163.6(d, J = 202.0 Hz), 161.7, 155.6 (d, J = 252.1 Hz), 154.4 (d, J = 2.9 Hz), 135.8, 129.8 (d, J = 7.9 Hz), 126.0 (d, J = 19.8 Hz), 124.2 (d, J = 7.9 Hz), 122.1 (d, J = 8.1 Hz), 120.6 (d, J = 20.0 Hz), 117.8 (d, J = 20.0 Hz), 113.5 (d, J = 20.0 Hz), 109.9 (d, J = 8.1 Hz), 61.4, 21.7, 21.6, 21.3. |
| B2 | Pale yellow solid | 158-162 | $^1$H NMR (500 MHz, $CDCl_3$) δ 8.0 (dt, J = 8.8, 1.9 Hz, 2H), 7.5-7.4 (m, 2H), 7.2 (d, J = 5.0 Hz, 2H), 5.4 (s, 2H), 2.4 (tq, J = 4.5, 1.5 Hz, 4H), 1.8 (ddd, J = 4.9, 3.7, 2.3 Hz, 4H). $^{13}$C NMR (101 MHz, $CDCl_3$) δ 166.2, 166.1, 163.8, 161.7, 155.6 (d, J = 252.1 Hz), 154.4 (d, J = 2.9 Hz), 135.8, 135.0, 132.0, 130.3, 126.9, 126.0 (d, J = 19.8 Hz), 125.3, 125.2, 122.1 (d, J = 8.1 Hz), 120.6 (d, J = 20.0 Hz), 109.9 (d, J = 8.1 Hz), 61.4, 21.7, 21.6, 21.3. |
| B3 | White solid | 147-153 | $^1$H NMR (500 MHz, $CDCl_3$) δ 7.9 (m, J = 9.7, 2.2, 1.2 Hz, 1H), 7.8-7.8 (m, 1H), 7.5-7.4 (m, 2H), 7.3 (ddt, J = 7.7, 2.0, 0.9 Hz, 1H), 7.2 (d, J = 5.0 Hz, 1H), 2.4-2.4 (m, 6H), 2.5 (q, J = 3.1 Hz, 4H), 1.9 (p, J = 2.9 Hz, 4H), $^{13}$C NMR (101 MHz, $CDCl_3$) δ 166.2, 166.1, 163.8, 161.7, 155.6 (d, J = 252.1 Hz), 154.4 (d, J = 2.9 Hz), 139.1, 135.8, 132.4, 129.6, 127.7, 126.0 (d, J = 19.8 Hz), 124.9, 124.9, 122.1 (d, J = 8.1 Hz), 120.6 (d, J = 20.0 Hz), 109.9 (d, J = 8.1 Hz), 61.4, 21.7, 21.6, 21.4, 21.3. |
| B4 | White solid | 197-199 | $^1$H NMR, (500 MHz, $CDCl_3$) δ 8.0 (m, J = 11.0, 5.1, 1.4 Hz, 1H), 7.4 (d, J = 8.0 Hz, 1H), 7.3 (m, J = 8.8, 5.9, 1.5 Hz, 2H), 7.2 (d, J = 5.0 Hz, 1H), 5.4 (s, 2H), 2.4 (m, J = 5.9, 4.5, 3.1, 1.7 Hz, 4H), 1.8 (m, J = 6.2, 5.2, 3.1, 1.8 Hz, 4H). $^{13}$C NMR (101 MHz, $CDCl_3$) δ 166.2, 166.1, 162.9 (d, J = 8.1 Hz). 162.7, 161.5, 160.7, 155.6 (d, J = 252.1 Hz), 154.4 (d, J = 2.9 Hz), 135.8, 132.3 (d, J = 7.9 Hz), 128.8 (d, J = 7.9 Hz), 126.0 (d, J = 19.8 Hz), 124.7 (d, J = 3.1 Hz), 122.1 (d, J = 8.1 Hz), 120.6 (d, J = 20.0 Hz), 116.5 (d, J = 20.0 Hz), 114.3 (d, J = 20.0 Hz), 109.9 (d, J = 8.1 Hz), 61.6, 21.7, 21.6, 21.3. |
| B5 | White solid | 138-140 | H NMR (500 MHz, $CDCl_3$) δ 7.9-7.8 (m, 1H), 7.7 (dd, J = 6.1, 3.0 Hz, 1H), 7.5-7.4 (m, 3H), 7.2 (d, J = 5.0 Hz, 1H), 5.4 (s, 2H), 2.4 (m, J = 5.9, 4.5, 3.1, 1.7 Hz, 4H), 2.0-1.5 (m, 4H). $^{13}$C NMR (101 MHz, $CDCl_3$) δ 166.2, 166.1, 162.3, 161.4, 155.6 (d, J = 252.1 Hz), 154.4 (d, J = 2.9 Hz), 135.8, 134.2, 131.0, 129.8, 128.5, 127.1, 126.0 (d, J = 19.8 Hz), 124.3, 122.1 (d, J = 8.1 Hz), 120.6 (d, J = 20.0 Hz), 109.9 (d, J = 8.1 Hz), 61.6, 21.7, 21.6, 21.3 |
| B6 | White solid | 121-124 | $^1$H NMR (500 MHz, $CDCl_3$) δ 7.9 (dd, J = 9.6, 1.5 Hz, 1H), 7.7 (dd, J = 7.7, 1.5 Hz, 1H), 7.5-7.4 (m, 3H), 7.2 (d, J = 5.0 Hz, 1H), 5.4 (s, 2H), 2.4 (d J = 7.0, 4.5, 3.1, 1.7 Hz, 4H), 2.0-1.4 (m, 4H). $^{13}$C NMR (101 MHz, $CDCl_3$) δ 166.2, 166.1, 164.2, 161.1, 155.6 (d, J = 252.1 Hz), 154.4 (d, J = 2.9 Hz), 135.8, 132.7, 131.8, 129.3, 127.7, 126.0 (d, J = 19.8 Hz), 125.8, 124.0, 122.1 (d, J = 8.1 Hz), 120.6 (d, J = 20.0 Hz), 109.9 (d, J = 8.1 Hz), 61.6, 21.7, 21.6, 21.3. |
| B7 | White solid | 123-130 | $^1$H NMR (500 MHz, $CDCl_3$) δ 8.0 (dd, J = 9.7, 1.2 Hz, 1H), 7.9 (dd, J = 7.3, 1.3 Hz, 1H), 7.5-7.4 (m, 2H), 7.2 (d, J = 5.0 Hz, 1H), 7.1 (td, J = 7.2, 1.3 Hz, 1H), 5.4 (s, 2H), 2.4 (m, J = 5.9, 2.9, 1.4 Hz, 4H), 2.1-1.6 (m, 4H). |

TABLE 1-continued

Physicochemical properties and spectral data of the target compounds prepared in Examples 1 to 74

| SN | State | Melting point (° C.) | $^1$H NMR, $^{13}$C NMR |
|---|---|---|---|
| B8 | Yellow solid | 155-159 | $^1$H NMR (500 MHz, $CDCl_3$) δ 8.1-8.0 (m, 2H), 7.7 (m, J = 7.0 Hz, 1H), 7.7 (m, J = 8.3 Hz, 1H), 7.4 (d, J = 7.9 Hz, 1H), 7.2 (d, J = 5.0 Hz, 1H), 5.4 (s, 2H), 2.4 (m, J = 3.1 Hz, 4H), 1.9-1.5 (m, 4H). |
| B9 | White solid | 144-147 | $^1$H NMR (500 MHz, $CDCl_3$) δ 8.0 (dd, J = 10.0, 1.2 Hz, 1H), 7.4 (d, J = 7.9 Hz, 1H), 7.4 (m, J = 10.1, 7.1, 1.7 Hz, 1H), 7.3-7.3 (m, 2H), 7.2 (d, J = 5.0 Hz, 1H), 5.4 (s, 2H), 2.6 (d, J = 0.7 Hz, 3H), 2.4 (m, J = 5.9, 4.5, 3.1, 1.7 Hz, 4H), 1.8 (m, J = 4.6, 3.2, 2.0 Hz, 4H). |
| B10 | Pale yellow solid | 166-168 | $^1$H NMR (500 MHz, $CDCl_3$) δ 8.1-7.9 (m, 2H), 7.6 (d, J = 7.9 Hz, 1H), 7.5-7.4 (m, 2H), 7.2 (d, J = 5.0 Hz, 1H), 5.4 (s, 2H), 2.4 (m, J = 4.5 Hz, 4H), 1.8 (m, J = 3.2 Hz, 4H). |
| B11 | Pale yellow solid | 133-135 | $^1$H NMR (500 MHz, $CDCl_3$) δ 8.3 (t, J = 2.2 Hz, 1H), 8.0 (m, J = 9.7 Hz, 1H), 7.7 (m, J = 2.2 Hz, 1H), 7.4 (d, J = 7.9 Hz, 1H), 7.4-7.3 (m, 1H), 7.2 (d, J = 5.0 Hz, 1H), 5.4 (s, 2H), 2.4 m, J = 4.5 Hz, 4H), 1.9-1.5 (m, 4H). |
| B12 | White solid | 137-139 | $^1$H NMR (500 MHz, $CDCl_3$) δ 8.8 (t, J = 2.2 Hz, 1H), 8.4 (d, J = 10.3 Hz, 1H), 8.2 (d, J = 7.7 Hz, 1H), 7.7 (dd, J = 10.2, 7.8 Hz, 1H), 7.4 (d, J = 7.9 Hz, 1H), 7.2 (d, J = 5.0 Hz, 1H), 5.4 (s, 2H), 2.4 (m, J = 3.1 Hz, 4H), 1.8 (m, J = 3.2 Hz, 4H). |
| B13 | White solid | 104-106 | $^1$H NMR (500 MHz, $CDCl_3$) δ 8.0 (d, J = 8.4 Hz, 2H), 7.4 (d, J = 8.1 Hz, 1H), 7.4-7.3 (m, 2H), 7.2 (d, J = 5.0 Hz, 1H), 5.4 (s, 2H), 2.4 (d, J = 1.0 Hz, 4H), 1.8 (m, J = 3.6 Hz, 3H). |
| B14 | White solid | 136-139 | $^1$H NMR (500 MHz, $CDCl_3$) δ 8.1-8.1 (m, 2H), 7.4 (d, J = 7.9 Hz, 1H), 7.3-7.2 (m, 2H), 7.2 (d, J = 5.0 Hz, 1H), 5.4 (s, 2H), 2.4 (m, J = 3.1 Hz, 4H), 1.9-1.6 (m, 4H). |
| B15 | White solid | 97-99 | $^1$H NMR (500 MHz, $CDCl_3$) δ 8.1-8.0 (m, 2H), 7.5-7.4 (m, 3H), 7.2 (d, J = 5.0 Hz, 1H), 5.4 (s, 2H), 2.4 (m, J = 3.1 Hz, 4H), 1.9-1.6 (m, 4H). |
| B16 | White solid | 96-99 | $^1$H NMR (500 MHz, $CDCl_3$) δ 8.0 (d, J = 8.6 Hz, 2H), 7.7 (d, J = 8.6 Hz, 2H), 7.4 (d, J = 7.9 Hz, 1H), 7.2 (d, J = 5.0 Hz, 1H), 5.4 (s, 2H), 2.4 (m, J = 2.8 Hz, 4H), 1.9-1.6 (m, 4H). |
| B17 | White solid | 171-175 | $^1$H NMR (500 MHz, $CDCl_3$) δ 8.0 (d, J = 8.2 Hz, 2H), 7.8 (d, J = 8.2 Hz, 2H), 7.4 (d, J = 7.9 Hz, 1H), 7.2 (d, J = 5.0 Hz, 1H), 5.4 (s, 2H), 2.4 (m, J = 3.1 Hz, 4H), 2.0-1.4 (m, 4H). |
| B18 | Yellow solid | 124-126 | $^1$H NMR (500 MHz, $CDCl_3$) δ 8.3 (d, J = 9.4 Hz, 2H), 8.2 (d, J = 9.5 Hz, 2H), 7.4 (d, J = 7.9 Hz, 1H), 7.2 (d, J = 5.0 Hz, 1H), 5.4 (s, 2H), 2.4 (m, J = 3.0 Hz, 4H), 1.8 (m, J = 3.2 Hz, 4H). |
| B19 | White solid | 151-153 | $^1$H NMR (400 MHz, $CDCl_3$) δ 8.0 (t, J = 8.0 Hz, 1H), 7.5 (d, J = 9.8 Hz, 2H), 7.3 (d, J = 9.0 Hz, 1H), 7.1 (d, J = 6.3 Hz, 1H), 5.4 (s, 2H), 2.5 (q, J = 3.1 Hz, 4H), 1.9 (p, J = 2.9 Hz, 4H) |
| B20 | White solid | 142-146 | $^1$H NMR (500 MHz, $CDCl_3$) δ 8.2-8.1 (m, 2H), 8.1 (dd, J = 9.2 Hz, 1H), 7.4 (d, J = 7.9 Hz, 1H), 7.2 (d, J = 5.0 Hz, 1H), 5.4 (s, 2H), 2.4 (m, J = 2.8 Hz, 4H), 2.0-1.2 (m, 4H). |
| C1 | Light brown solid | 124-131 | H NMR (400 MHz, $CDCl_3$) δ 8.0 (dd, J = 8.1 Hz, 2H), 7.6 (t, J = 7.5 Hz, 1H), 7.5 (t, J = 7.7 Hz, 2H), 7.3-7.2 (m, 1H), 6.8 (d, J = 6.3 Hz, 1H), 5.3 (s, 2H), 2.4 (d, J = 3.3 Hz, 4H), 1.8 (t, J = 3.1 Hz, 4H). $^{13}$C NMR (101 MHz, $CDCl_3$) δ 193.5, 168.7, 152.3 (d, J = 249.3 Hz), 150.3 (d, J = 2.9 Hz), 142.5, 134.2 (d, J = 7.1 Hz), 128.9, 128.3, 124.4 (d, J = 9.5 Hz), 118.6 (d, J = 24.2 Hz), 118.2 (d, J = 14.6 Hz), 115.2, 72.5, 21.2, 20.3. |
| C2 | Yellow solid | 151-160 | $^1$H NMR (400 MHz, $CDCl_3$) δ 7.9 (d, J = 8.0 Hz, 2H), 7.4-7.2 (m, 3H), 6.8 (d, J = 6.3 Hz, 1H), 5.3 (s, 2H), 2.4 (d, J = 7.3 Hz, 7H), 1.8 (t, J = 3.2 Hz, 4H). $^{13}$C NMR (101 MHz, $CDCl_3$) δ 193.1, 168.7, 152.2 (d, J = 249.3 Hz), 150.4 (d, J = 2.9 Hz), 145.2, 142.5, 131.7, 129.6, 128.4, 124.3 (d, J = 9.4 Hz), 118.6 (d, J = 24.6 Hz), 118.2 (d, J = 14.6 Hz), 115.1, 72.5, 21.8, 21.2, 20.3. |
| C3 | White solid | 171-178 | $^1$H NMR (400 MHz, $CDCl_3$) δ 8.1 (d, J = 8.2 Hz, 2H), 7.8 (d, J = 8.3 Hz, 2H), 7.4-7.2 (m, 1H), 6.8 (d, J = 6.2 Hz, 1H), 5.3 (s, 2H), 2.4 (q, J = 3.0 Hz, 4H), 1.8 (p, J = 2.9 Hz, 4H). $^{13}$C NMR (101 MHz, $CDCl_3$) δ 193.1, 168.6, 152.5 (d, J = 250.6 Hz), 149.9 (d, J = 2.9 Hz), 142.6, 137.2, 132.7, 129.0, 124.4 (d, J = 9.5 Hz), 118.8 (d, J = 24.6 Hz), 118.4 (d, J = 14.7 Hz), 117.5 (d, J = 43.6 Hz), 115.2, 77.1-69.0 (m), 21.2, 20.3 |
| C4 | White solid | 141-143 | $^1$H NMR (400 MHz, $CDCl_3$) δ 8.0 (t, J = 7.5 Hz, 1H), 7.7-7.6 (m, 1H), 7.4-7.3 (m, 2H), 7.2 (dd, J = 8.3 Hz, 1H), 6.8 (d, J = 6.3 Hz, 1H), 5.3 (d, J = 3.3 Hz, 2H), 2.4 (q, J = 3.0 Hz, 4H), 1.8 (p, J = 2.9 Hz, 4H). $^{13}$C NMR (101 MHz, $CDCl_3$) δ 191.5 (d, J = 5.1 Hz), 168.7, 162.3 (d, J = 253.8 Hz), 152.3 (d, J = 249.3 Hz), 150.4 (d, J = 3.2 Hz), 142.5, 135.8 (d, J = 9.0 Hz), 130.9 (d, J = 3.3 Hz), 125.0 (d, J = 3.0 Hz), 124.5 (d, J = 9.5 Hz), 122.6 (d, J = 14.6 Hz), 118.6 (d, J = 24.6 Hz), 118.2 (d, J = 14.6 Hz), 116.6 (d, J = 23.4 Hz), 115.3, 75.1 (d, J = 13.0 Hz), 21.2, 20.3. |
| C5 | White solid | 135-137 | $^1$H NMR (400 MHz, $CDCl_3$) δ 7.7 (m, J = 8.4 Hz, 1H), 7.4-7.3 (m, 2H), 7.2 (m, J = 9.5 Hz, 1H), 6.8 (d, J = 6.3 Hz, 1H), 5.3 (d, J = 3.4 Hz, 2H), 2.4 (t, J = 3.2 Hz, 4H), 1.8 (p, J = 2.9 Hz, 4H). $^{13}$C NMR (101 MHz, $CDCl_3$) δ 190.5 (d, J = 5.7 Hz), 168.7, 159.8 (d, J = 69.1 Hz), 157.3 (d, J = 73.9 Hz), 152.4 (d, J = 249.7 Hz), 150.3 (d, J = 2.9 Hz), 142.5, 124.6 (d, J = 9.5 Hz), 123.8 (d, J = 6.4 Hz), 123.6 (d, J = 6.6 Hz), 122.7 (d, J = 9.5 Hz), 122.4 (d, J = 9.5 Hz), 118.6 (d, J = 24.5 Hz), 118.4 (d, J = 8.2 Hz), 118.2-118.0 (m), 116.8 (d, J = 4.2 Hz), 116.6 (d, J = 4.2 Hz), 75.1 (d, J = 13.1 Hz), 21.2, 20.3. |

TABLE 1-continued

Physicochemical properties and spectral data of the target compounds prepared in Examples 1 to 74

| SN | State | Melting point (° C.) | $^{1}H$ NMR, $^{13}C$ NMR |
|---|---|---|---|
| C6 | Yellow oil | — | $^{1}H$ NMR (400 MHz, $CDCl_3$) δ 7.9 (dd, J = 7.8 Hz, 1H), 7.6 (m, J = 8.8 Hz, 1H), 7.3-7.3 (m, 1H), 7.1-7.0 (m, 2H), 6.7 (d, J = 6.3 Hz, 1H), 5.3 (d, J = 2.5 Hz, 2H), 4.0 (s, 3H), 2.4 (q, J = 3.0 Hz, 4H), 1.8 (p, J = 3.0 Hz, 4H) $^{13}C$ NMR (101 MHz, $CDCl_3$) δ 194.4, 168.7, 159.4, 153.2, 150.8 (d, J = 2.9 Hz). 150.7, 142.4, 135.0, 131.1, 124.5, 124.1 (d, J = 9.5 Hz), 121.2, 118.4 (d, J = 24.6 Hz), 118.1 (d, J = 14.8 Hz), 114.9, 111.5, 75.8, 55.7, 21.2, 20.3. |
| C7 | Brownish yellow oil | — | $^{1}H$ NMR (400 MHz, $CDCl_3$) δ 7.8 (d, J = 7.8 Hz, 1H), 7.7 (dt, J = 9.2, 2.0 Hz, 1H), 7.5 (td, J = 8.0, 5.4 Hz, 1H), 7.4-7.3 (m, 2H), 6.8 (d, J = 6.3 Hz, 1H), 5.3 (s, 2H), 2.4 (q, J = 3.1 Hz, 4H), 2.2-1.4 (m, 4H). $^{13}C$ NMR (101 MHz, $CDCl_3$) δ 192.5 (d, J = 2.2 Hz), 168.7, 162.9 (d, J = 248.6 Hz), 152.4 (d, J = 249.9 Hz), 150.1 (d, J = 2.9 Hz), 142.5, 136.1 (d, J = 6.5 Hz), 130.6 (d, J = 7.9 Hz), 124.5 (d, J = 9.5 Hz), 124.1 (d, J = 3.5 Hz), 121.2 (d, J = 21.1 Hz), 118.7 (d, J = 24.3 Hz), 118.3 (d, J = 14.5 Hz), 115.2, 115.0, 72.6, 21.2, 20.3. |
| C8 | White solid | 126-128 | $^{1}H$ NMR (400 MHz, $CDCl_3$) δ 8.0 (d, J = 8.6 Hz, 2H), 7.5-7.4 (m, 2H), 7.4-7.2 (m, 1H), 6.8 (d, J = 6.3 Hz, 1H), 5.3 (s, 2H), 2.4 (q, J = 3.0 Hz, 4H), 1.8 (p, J = 3.0 Hz, 4H). $^{13}C$ NMR (101 MHz, $CDCl_3$) δ 192.7, 168.6, 152.4 (d, J = 250.0 Hz), 150.1 (d, J = 2.9 Hz), 142.5, 140.7, 132.5, 129.8, 129.2, 124.4 (d, J = 9.5 Hz), 118.7 (d, J = 24.7 Hz), 118.3 (d, J = 14.6 Hz), 115.1, 72.6, 21.2, 20.3. |
| C9 | Yellow solid | 148-150 | $^{1}H$ NMR (400 MHz, $CDCl_3$) δ 8.4 (d, J = 8.8 Hz, 2H), 8.2 (d, J = 8.8 Hz, 2H), 7.3 (d, J = 8.9 Hz, 1H), 6.8 (d, J = 6.2 Hz, 1H), 5.3 (s, 2H), 2.4 (q, J = 3.0 Hz, 4H), 1.8 (t, J = 3.1 Hz, 4H). $^{13}C$ NMR (101 MHz, $CDCl_3$) δ 193.0, 168.6, 152.5 (d, J = 250.7 Hz), 150.8, 149.8 (d, J = 3.0 Hz), 142.6, 138.7, 129.7, 124.4 (d, J = 9.5 Hz), 124.0, 118.8 (d, J = 24.6 Hz), 118.4 (d, J = 14.6 Hz), 115.2, 72.9, 21.2, 20.3. |
| C10 | Pale yellow solid | 119-121 | $^{1}H$ NMR (400 MHz, Chloroform-d) δ 7.5-7.4 (m, 2H), 7.3 (d, J = 9.1 Hz, 1H), 7.1 (t, J = 8.7 Hz, 2H), 6.9 (d, J = 6.4 Hz, 1H), 5.1 (s, 1H), 2.4 (q, J = 3.1 Hz, 4H), 1.8 (p, J = 2.9 Hz, 4H). $^{13}C$ NMR (101 MHz, Chloroform-d) δ 168.8, 163.9, 161.4, 152.5 (d, J = 250.7 Hz), 150.7 (d, J = 2.9 Hz), 150.6, 142.5, 131.6 (d, J = 3.4 Hz), 129.3 (d, J = 8.5 Hz), 124.3 (d, J = 9.5 Hz), 118.5 (d, J = 24.4 Hz), 118.2 (d, J = 14.5 Hz), 115.6 (d, J = 21.8 Hz), 114.7, 71.1, 21.3, 20.3. |
| C11 | Pale yellow solid | 148-150 | $^{1}H$ NMR (400 MHz, $CDCl_3$) δ 8.0 (d, J = 8.6 Hz, 2H), 7.5 (dd, J = 12.7, 8.5 Hz, 3H), 7.0 (dd, J = 8.5, 2.2 Hz, 1H), 6.9 (d, J = 2.2 Hz, 1H), 5.3 (s, 2H), 2.4 (t, J = 3.1 Hz, 4H), 1.8 (t, J = 3.1 Hz, 4H). $^{13}C$ NMR (101 MHz, $CDCl_3$) δ 192.9, 169.5, 152.5 (d, J = 250.7 Hz), 142.0, 140.5, 132.7, 131.5, 130.6, 129.9, 129.2, 121.9, 119.5, 111.4, 71.9, 21.3, 20.2. |
| C12 | Yellow solid | 158-160 | $^{1}H$ NMR (400 MHz, $CDCl_3$) δ 8.1 (td, J = 8.4, 6.5 Hz, 1H), 7.5 (d, J = 8.5 Hz, 1H), 7.1-7.0 (m, 2H), 7.0-6.9 (m, 2H), 5.3 (d, J = 3.3 Hz, 2H), 2.4 (d, J = 3.3 Hz, 4H), 1.8 (p, J = 2.9 Hz, 4H). $^{13}C$ NMR (101 MHz, $CDCl_3$) δ 190.5 (d, J = 5.8 Hz), 169.5, 153.7, 141.9, 133.0 (dd, J = 10.8, 5.0 Hz), 131.4, 130.5, 129.5, 128.4, 122.0, 119.4, 112.9 (dd, J = 21.7, 3.3 Hz), 111.5, 104.9 (d, J = 27.2 Hz), 104.5, 74.2 (d, J = 12.4 Hz), 21.3, 20.2. |
| C13 | White solid | 151-153 | $^{1}H$ NMR (400 MHz, $CDCl_3$) δ 8.0 (d, J = 8.9 Hz, 2H), 7.3-7.2 (m, 1H), 7.0 (d, J = 8.9 Hz, 2H), 6.8 (d, J = 6.3 Hz, 1H), 5.3 (s, 2H), 3.9 (s, 2H), 2.4 (q, J = 3.0 Hz, 4H), 1.8 (p, J = 2.9 Hz, 4H). $^{13}C$ NMR (101 MHz, $CDCl_3$) δ 192.0, 168.7, 164.2, 152.2 (d, J = 249.3 Hz), 150.4 (d, J = 2.9 Hz), 142.5, 130.7, 127.2, 124.3 (d, J = 9.4 Hz), 118.5 (d, J = 24.6 Hz), 118.2 (d, J = 14.6 Hz), 115.0, 114.1, 72.4, 55.6, 21.2, 20.3. |
| C14 | White solid | 183-185 | $^{1}H$ NMR (400 MHz, $CDCl_3$) δ 8.1 (d, J = 8.1 Hz, 2H), 7.8 (d, J = 8.2 Hz, 2H), 7.4-7.2 (m, 1H), 6.8 (d, J = 6.2 Hz, 1H), 5.3 (s, 2H), 2.5-2.3 (m, 4H), 1.8 (p, J = 2.9 Hz, 4H). $^{13}C$ NMR (101 MHz, $CDCl_3$) δ 193.1, 168.6, 152.5 (d, J = 250.7 Hz), 149.9 (d, J = 2.9 Hz), 142.6, 137.2, 132.7, 129.0, 124.4 (d, J = 9.5 Hz), 118.8 (d, J = 24.6 Hz), 118.4 (d, J = 14.9 Hz), 117.7, 117.3, 115.2, 72.8, 21.2, 20.3. |
| C15 | Yellow solid | 144-146 | $^{1}H$ NMR (400 MHz, $CDCl_3$) δ 7.9 (d, J = 8.0 Hz, 2H), 7.3 (d, J = 8.5 Hz, 3H), 6.8 (d, J = 6.3 Hz, 1H), 5.3 (s, 2H), 2.4 (d, J = 6.9 Hz, 7H), 1.8 (t, J = 3.1 Hz, 4H), $^{13}C$ NMR (101 MHz, $CDCl_3$) δ 193.1, 168.7, 152.2 (d, J = 249.4 Hz), 150.4 (d, J = 2.8 Hz), 145.2, 142.5, 131.7, 129.6, 128.4, 124.4 (d, J = 9.5 Hz), 118.6 (d, J = 24.3 Hz), 118.2 (d, J = 14.7 Hz), 115.1, 72.5, 21.8, 21.2, 20.3. |
| D1 | White solid | 155-157 | $^{1}H$ NMR (500 MHz, $CDCl_3$) δ 8.3 (d, J = 7.4 Hz, 1H), 7.7 (s, 1H), 7.2 (d, J = 8.9 Hz, 1H), 2.4 (h, J = 2.5, 2.0 Hz, 4H), 2.2 (s, 3H), 1.8 (dq, J = 6.1, 3.2, 2.8 Hz, 4H). $^{13}C$ NMR (126 MHz, $CDCl_3$) δ 168.9, 168.4, 153.5 (d, J = 252.4 Hz), 142.6, 131.7 (d, J = 3.5 Hz), 123.1 (d, J = 9.2 Hz), 122.3, 118.7 (d, J = 13.8 Hz), 117.2 (d, J = 24.3 Hz), 45.9, 24.8, 21.3, 20.4, 8.7. |
| D2 | Brown oil | — | $^{1}H$ NMR (500 MHz, $CDCl_3$) δ 9.3 (s, 1H), 7.7 (d, J = 8.1 Hz, 1H), 7.1 (d, J = 4.9 Hz, 1H), 4.2 (s, 2H), 2.4 (h, J = 2.5, 2.1 Hz, 4H), 1.8 (p, J = 3.3 Hz, 4H). $^{13}C$ NMR (126 MHz, $CDCl_3$) δ 165.9 (d, J = 11.9 Hz), 165.1, 155.7 (d, J = 251.8 Hz), 125.5 (d, J = 20.0 Hz), 123.1 (d, J = 8.1 Hz), 122.7 (d, J = 20.0 Hz), 114.7 (d, J = 8.1 Hz), 43.0, 21.7 (d, J = 1.4 Hz), 21.3. |
| D3 | Brown oil | — | $^{1}H$ NMR (500 MHz, $CDCl_3$) δ 9.0 (s, 1H), 7.7 (d, J = 8.1 Hz, 1H), 7.1 (d, J = 5.0 Hz, 1H), 4.7 (q, J = 5.9 Hz, 1H), 2.4 (h, J = 2.5, 2.1 Hz, 4H), 1.8 (p, J = 3.3 Hz, 4H). $^{13}C$ NMR (126 MHz, $CDCl_3$) δ 168.9, 165.9, 165.8, 155.6 (d, J = |

TABLE 1-continued

| Physicochemical properties and spectral data of the target compounds prepared in Examples 1 to 74 | | | |
|---|---|---|---|
| SN | State | Melting point (° C.) | $^1$H NMR, $^{13}$C NMR |
| | | | 251.8 Hz), 137.0 (d, J = 3.1 Hz), 135.8, 125.6 (d, J = 20.0 Hz), 123.7 (d, J = 8.1 Hz), 122.6 (d, J = 20.0 Hz), 114.9 (d, J = 8.1 Hz), 54.9, 21.7 (d, J = 1.4 Hz), 21.3, 21.2. |
| D4 | Yellow oil | — | $^1$H NMR (500 MHz, $CDCl_3$) δ 8.6 (s, 1H), 7.7 (d, J = 8.1 Hz, 1H), 7.2 (d, J = 5.0 Hz, 1H), 3.8-3.7 (m, 2H), 2.4 (ddd, J = 5.4, 2.8, 1.5 Hz, 4H), 1.8-1.7 (m, 4H), 1.3 (s, 6H). $^{13}$C NMR (126 MHz, $CDCl_3$) δ 178.2, 165.9, 165.8, 155.6 (d, J = 251.8 Hz), 137.5 (d, J = 3.1 Hz), 135,8, 125.8 (d, J = 20.0 Hz), 123.5 (d, J = 7.9 Hz), 122.5 (d, J = 20.0 Hz), 114.6 (d, J = 8.1 Hz), 51.9, 45.7, 24.1, 21.7 (d, J = 1.4 Hz), 21.3. |
| D5 | White solid | 133-138 | $^1$H NMR (500 MHz, $CDCl_3$) δ 8.8 (s, 1H), 7.7 (d, J = 8.1 Hz, 1H), 7.2 (d, J = 5.0 Hz, 1H), 6.8 (dq, J = 14.1, 5.7 Hz, 1H), 6.2 (dd, J = 14.0, 1.6 Hz, 1H), 2.4 (dtd, J = 5.4, 2.8, 1.4 Hz, 4H), 1.9 (dd, J = 5.7, 1.6 Hz, 4H), 1.8 (tq, J = 3.2, 2.0 Hz, 5H). $^{13}$C NMR (126 MHz, $CDCl_3$) δ 165.9, 165.8, 165.4, 155.6 (d, J = 251.8 Hz), 142.4, 136.6 (d, J = 2.9 Hz), 135.8, 125.6 (d, J = 20.0 Hz), 123.1 (d, J = 8.1 Hz), 122.6 (d, J = 20.0 Hz), 122.3, 115.6 (d, J = 7.9 Hz), 21.7 (d, J = 1.4 Hz), 21.3, 17.6. |
| D6 | Yellow oil | — | $^1$H NMR (500 MHz, $CDCl_3$) δ 9.9 (s, 1H), 8.4 (d, J = 7.4 Hz, 1H), 7.3-7.1 (m, 1H), 4.3 (q, J = 7.2 Hz, 2H), 3.5 (s, 2H), 2.4 (h, J = 2.5, 2.1 Hz, 4H), 1.8 (p, J = 3.3 Hz, 4H), 1.3 (t, J = 7.2 Hz, 3H). $^{13}$C NMR (126 MHz, $CDCl_3$) δ 163.1, 162.2, 156.5, 147.1 (d, J = 252.7 Hz), 135.9, 124.9 (d, J = 3.5 Hz), 117.2 (d, J = 9.2 Hz), 115.8, 112.0 (d, J = 13.9 Hz), 110.8 (d, J = 24.4 Hz), 55.6, 34.8, 14.7, 13.7, 7.5. |
| D7 | Yellow oil | — | $^1$H NMR (500 MHz, $CDCl_3$) δ 8.8 (s, 1H), 7.7 (d, J = 8.1 Hz, 1H), 7.1 (d, J = 4.9 Hz, 1H), 2.4 (h, J = 2.5, 2.1 Hz, 4H), 2.3 (t, J = 8.3 Hz, 3H), 1.8 (p, J = 3.3 Hz, 4H), 1.6 (p, J = 8.0 Hz, 3H), 1.4-1.2 (m, 13H), 0.9-0.8 (m, 3H). $^{13}$C NMR (126 MHz, $CDCl_3$) δ 172.5, 165.9, 165.8, 155.7 (d, J = 251.8 Hz), 137.0 (d, J = 2.9 Hz), 135.8, 125.5 (d, J = 20.0 Hz), 123.1, 122.5 (d, J = 20.0 Hz), 114.6 (d, J = 8.1 Hz), 36.6, 30.8, 29.2, 28.6, 27.8, 25.5, 22.7, 21.7 (d, J = 1.4 Hz), 21.3, 14.1. |
| D8 | White solid | 208-210 | $^1$H NMR (500 MHz, $CDCl_3$) δ 8.7 (s, 1H), 7.7 (d, J = 8.1 Hz, 1H), 7.1 (d, J = 5.0 Hz, 1H), 2.4 (h, J = 2.5, 2.1 Hz, 4H), 2.1 (p, J = 5.5 Hz, 1H), 1.8 (p, J = 3.3 Hz, 4H). $^{13}$C NMR (126 MHz, $CDCl_3$) δ 172.4, 165.9, 165.8, 155.6 (d, J = 251.8 Hz), 137.4 (d, J = 3.1 Hz), 135.8, 125.6 (d, J = 20.0 Hz), 123.8 (d, J = 7.9 Hz), 122.5 (d, J = 20.0 Hz), 114.6 (d, J = 7.9 Hz), 21.7 (d, J = 1.4 Hz), 21.3, 17.1, 8.0. |
| D9 | White solid | 145-147 | $^1$H NMR (500 MHz, $CDCl_3$) δ 8.6 (s, 1H), 7.7 (d, J = 8.1 Hz, 1H), 7.1 (d, J = 5.0 Hz, 1H), 2.8 (p, J = 5.1 Hz, 1H), 2.4 (tdd, J = 5.8, 3.1, 1.7 Hz, 4H), 2.3-2.2 (m, 2H), 2.2-2.1 (m, 2H), 1.9 (dt, J = 12.4, 8.3 Hz, 1H), 1.8 (dt, J = 12.4, 8.4 Hz, 1H), 1.8 (dtt, J = 5.1, 3.7, 1.9 Hz, 4H). $^{13}$C NMR (126 MHz, $CDCl_3$) δ 173.3, 165.9, 165.8, 155.6 (d, J = 251.8 Hz), 137.5 (d, J = 3.1 Hz), 135.8, 125.6 (d, J = 20.0 Hz), 123.8 (d, J = 7.9 Hz), 122.5 (d, J = 20.0 Hz), 114.6 (d, J = 7.9 Hz), 39.7, 28.1, 21.7 (d, J = 1.4 Hz), 21.3, 19.4. |
| D10 | Pale yellow solid | 93-97 | $^1$H NMR (500 MHz, $CDCl_3$) δ 8.6 (s, 1H), 7.7 (d, J = 8.1 Hz, 1H), 7.1 (d, J = 5.0 Hz, 1H), 2.5 (p, J = 5.7 Hz, 1H), 2.4 (dtd, J = 5.4, 2.8, 1.4 Hz, 5H), 1.9 (ddt, J = 12.0, 8.6, 5.7 Hz, 3H), 1.8 (ddt, J = 4.1, 2.5, 1.5 Hz, 4H), 1.7-1.6 (m, 2H), 1.6-1.5 (m, 4H), 1.5-1.4 (m, 3H). $^{13}$C NMR (126 MHz, $CDCl_3$) δ 174.8, 165.9, 165.8, 155.6 (d, J = 251.8 Hz), 137.5 (d, J = 3.1 Hz), 135.8, 125.6 (d, J = 20.0 Hz), 123.8 (d, J = 7.9 Hz), 122.5 (d, J = 20.0 Hz), 114.6 (d, J = 7.9 Hz), 45.6, 29.1, 25.5, 25.4, 21.7 (d, J = 1.4 Hz), 21.3. |
| E1 | Pale yellow solid | 138-141 | $^1$H NMR (500 MHz, $CDCl_3$) δ 8.2-7.9 (m, 1H), 7.4 (d, J = 9.3 Hz, 0H), 7.0 (ddd, J = 9.2, 7.3, 2.4 Hz, 1H), 6.9 (ddd, J = 11.0, 8.4, 2.3 Hz, 0H), 5.4 (d, J = 3.8 Hz, 1H), 2.4 (h, J = 2.5, 2.0 Hz, 2H), 1.8 (p, J = 3.3 Hz, 2H). $^{13}$C NMR (126 MHz, $CDCl_3$) δ 188.4 (d, J = 5.6 Hz), 168.5, 163.0, 159.6 (d, J = 262.6 Hz), 142.8, 136.3 (d, J = 10.4 Hz), 133.8 (d, J = 2.7 Hz), 133.0 (dd, J = 10.8, 4.8 Hz), 125.6 (d, J = 3.8 Hz), 120.0 (d, J = 23.5 Hz), 119.0 (d, J = 11.4 Hz), 118.7 (d, J = 13.6 Hz), 113.0 (dd, J = 21.6, 3.1 Hz), 104.9, 104.9 (d, J = 52.9 Hz), 69.7 (d, J = 14.8 Hz), 21.3, 20.4. |
| E2 | White solid | 133-136 | $^1$H NMR (500 MHz, $CDCl_3$) δ 8.2 (d, J = 5.1 Hz, 1H), 8.0-7.9 (m, 2H), 7.7 (d, J = 8.0 Hz, 1H), 7.6-7.5 (m, 3H), 5.7 (s, 2H), 2.4 (dtd, J = 5.4, 2.8, 1.4 Hz, 4H), 1.9-1.3 (m, 4H). $^{13}$C NMR (126 MHz, $CDCl_3$) δ 193.1, 166.3, 166.2, 159.0 (d, J = 252.1 Hz), 135.8, 134.5, 133.3, 131.7 (d, J = 7.9 Hz), 128.8, 128.5, 127.9 (d, J = 2.9 Hz), 127.5 (d, J = 7.9 Hz), 125.3 (d, J = 20.0 Hz), 121.1 (d, J = 20.0 Hz), 66.9, 21.7 (d, J = 1.4 Hz), 21.3. |

Post-Emergence Herbicidal Activity Test of the Target Compounds Obtained in the Examples (1) Post-Emergence Stem and Leaf Spray Treatment:

The weeds were cultivated in a 180 mm×140 mm plastic nutrient pot by a pot-culture method, placed in an enamel tray, and the plastic nutrient pots were filled with surface soil (⅘ of a depth) collected from a farmland and air-dried and sieved, and a soil humidity was controlled at 20% in the initial stage. Weed seeds with plump and uniform grains were selected, soaked in warm water at 25° C. for 6 h, and germinated in a biochemical incubator (dark) at 28° C. The freshly exposed weed seeds were evenly placed on the soil surface, and then covered with 0.5 cm to 1 cm of soil according to the size of the seeds. The weeds are cultivated in a controlled sunlight greenhouse at 20° C. to 30° C., under natural light, and a relative humidity of 57% to 72%. The soil was loam, including 1.63% of organic matters, with a pH value of 7, 84.3 mg/kg of alkaline nitrogen, 38.5 mg/kg of available phosphorus, and 82.1 mg/kg of available potassium.

Each treatment was repeated 2 times, each treatment included 12 pots, and 20 weed seeds were sown in each pot. Pesticide was applied in the test for 1 time in total. When the weeds grew to 1.5- to 2-leaf stage, thinning was conducted, with 10 weeds in each pot, and 30 weeds were kept in each treatment.

The cultivated weeds were placed on trays with an area of 0.1 $m^2$, and stems and leaves were sprayed with a sprayer. After applying a pesticide, the pesticide applied weeds were moved into a greenhouse for routine cultivation.

2 weeks after sowing, the test plants were treated at the 2- to 3-leaf stage: the compounds of the present disclosure for testing were dissolved in acetone separately, and added with Tween 80, an emulsifiable oil of 1.5 liters/ha methyl oleate was added as a synergist, and an obtained mixture was diluted with certain water to a certain concentration solution. The solution was sprayed onto the plants using a spray tower. After spraying, the weeds were cultivated in the greenhouse for 3 weeks, and the experimental effects on the weeds were counted. The effective concentrations of the compounds were 10 g/mu, 5 g/mu, and 2.5 g/mu, the experiment was repeated three times, and an average result was taken. Representative data are listed in Table 2.

TABLE 2

Post-emergence herbicidal activity test results of target compounds obtained in examples (g/mu)

| SN | Dosage | *E. crusgalli* | *S. viridis* | *Trifoliumre pensL.* | *A. theophrasti* | *A. retroflexus* | *P. oleracea* |
|---|---|---|---|---|---|---|---|
| A1 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A2 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A3 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A4 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A5 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| A6 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A7 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A8 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A9 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A10 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A11 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A12 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A13 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A14 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A15 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| A16 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A17 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A18 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |

TABLE 2-continued

Post-emergence herbicidal activity test results of target compounds obtained in examples (g/mu)

| SN | Dosage | *E. crusgalli* | *S. viridis* | *Trifoliumre pensL.* | *A. theophrasti* | *A. retroflexus* | *P. oleracea* |
|---|---|---|---|---|---|---|---|
| A19 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A20 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A21 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A22 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A23 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A24 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A25 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A26 | 10 | 3 | 4 | 5 | 5 | 5 | 5 |
| | 5 | 2 | 3 | 5 | 5 | 5 | 5 |
| | 2.5 | 1 | 2 | 4 | 5 | 5 | 4 |
| A27 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B1 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B2 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B3 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B4 | 10 | 3 | 4 | 5 | 5 | 5 | 5 |
| | 5 | 2 | 3 | 5 | 5 | 5 | 5 |
| | 2.5 | 1 | 2 | 5 | 4 | 5 | 4 |
| B5 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B6 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B7 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B8 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B9 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B10 | 10 | 3 | 4 | 5 | 5 | 5 | 5 |
| | 5 | 2 | 3 | 5 | 5 | 5 | 5 |
| | 2.5 | 1 | 2 | 5 | 4 | 4 | 5 |
| B11 | 10 | 3 | 4 | 5 | 5 | 5 | 5 |
| | 5 | 2 | 3 | 5 | 5 | 5 | 5 |
| | 2.5 | 1 | 2 | 5 | 4 | 4 | 5 |
| B12 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B13 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B14 | 10 | 3 | 4 | 5 | 5 | 5 | 5 |
| | 5 | 2 | 3 | 5 | 5 | 5 | 5 |
| | 2.5 | 1 | 2 | 5 | 4 | 5 | 4 |
| B15 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B16 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |

TABLE 2-continued

Post-emergence herbicidal activity test results of target compounds obtained in examples (g/mu)

| SN | Dosage | *E. crusgalli* | *S. viridis* | *Trifoliumre pensL.* | *A. theophrasti* | *A. retroflexus* | *P. oleracea* |
|---|---|---|---|---|---|---|---|
| B17 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B18 | 10 | 3 | 4 | 5 | 5 | 5 | 5 |
| | 5 | 2 | 3 | 5 | 5 | 5 | 5 |
| | 2.5 | 1 | 2 | 5 | 4 | 5 | 4 |
| B19 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| B20 | 10 | 3 | 4 | 5 | 5 | 5 | 5 |
| | 5 | 2 | 3 | 5 | 5 | 5 | 5 |
| | 2.5 | 1 | 2 | 4 | 5 | 4 | 5 |
| C1 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C2 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C3 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C4 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C5 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C6 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C7 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C8 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C9 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C10 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C11 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C12 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C13 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C14 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| C15 | 10 | 3 | 4 | 5 | 5 | 5 | 5 |
| | 5 | 2 | 3 | 5 | 5 | 5 | 5 |
| | 2.5 | 1 | 2 | 5 | 5 | 5 | 5 |
| D1 | 10 | 3 | 4 | 5 | 5 | 5 | 5 |
| D2 | 10 | 3 | 3 | 5 | 5 | 5 | 5 |
| D3 | 10 | 3 | 3 | 5 | 5 | 5 | 5 |
| D4 | 10 | 3 | 3 | 5 | 5 | 5 | 5 |
| D5 | 10 | 3 | 4 | 5 | 5 | 5 | 5 |
| D6 | 10 | 3 | 3 | 5 | 5 | 5 | 5 |
| D7 | 10 | 3 | 4 | 5 | 5 | 5 | 5 |
| D8 | 10 | 3 | 3 | 5 | 5 | 5 | 5 |
| D9 | 10 | 3 | 3 | 5 | 5 | 5 | 5 |
| D10 | 10 | 3 | 4 | 5 | 5 | 5 | 5 |
| E1 | 10 | 3 | 4 | 5 | 5 | 5 | 5 |
| E2 | 10 | 3 | 4 | 4 | 5 | 5 | 5 |

Biological Activity Evaluation:

The activity level criteria for plant destruction (i.e. growth control rate) are as follows:

Grade 5: the growth control rate is greater than or equal to 85%;

Grade 4: the growth control rate is greater than or equal to 60% and less than 85%;

Grade 3: the growth control rate is greater than or equal to 40% and less than 60%;

Grade 2: the growth control rate is greater than or equal to 20% and less than 40%;

Grade 1: the growth control rate is greater than or equal to 5% and less than 20%; and Grade 0: the growth control rate is less than 5%.

The growth control rate is a fresh weight control rate.

The above described are merely preferred embodiments of the present disclosure and are not intended to limit the present disclosure in any form. Although the present disclosure is described in detail in conjunction with the foregoing embodiments, they are only a part of, not all of, the embodiments of the present disclosure. Other embodiments can be obtained based on these examples without creative efforts, and all of these embodiments shall fall within the protection scope of the present disclosure.

What is claimed is:

1. An N-phenylimine derivative, being selected from the group consisting of: 1,2,4-oxadiazole-N-phenylimine derivative represented by formula 1 or 1,3,4-oxadiazole-N-phenylimine derivative represented by formula 2, formula 1

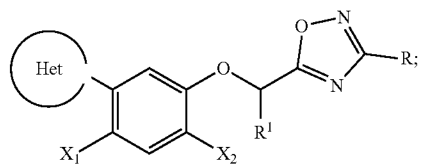

formula 2

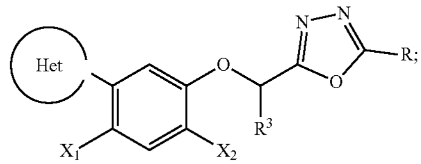

Het is selected from the group consisting of:

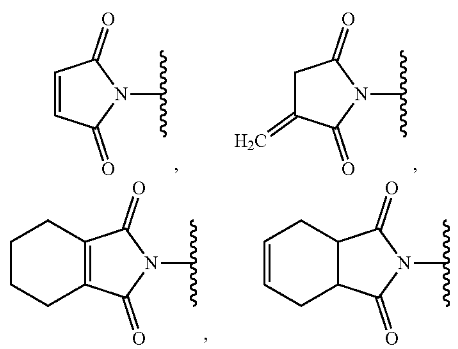

-continued

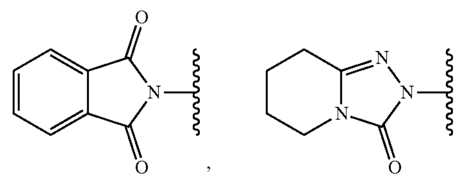

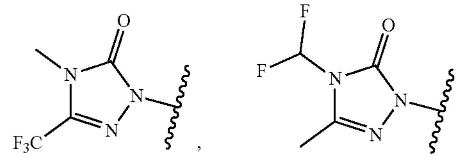

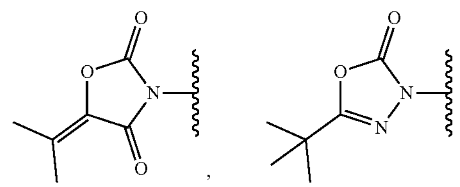

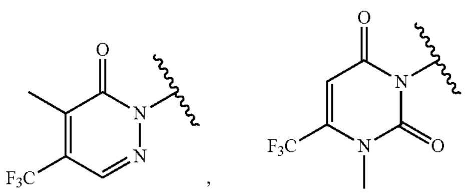

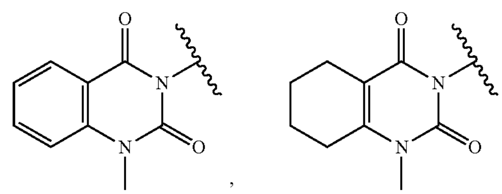

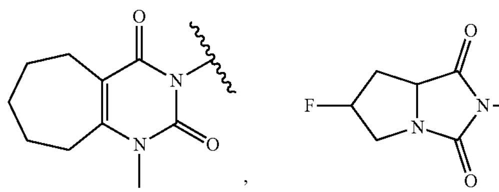

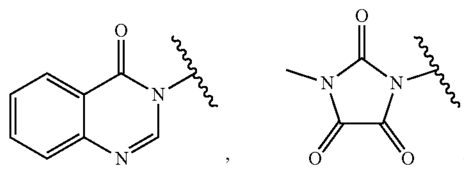

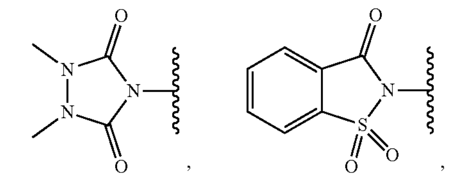

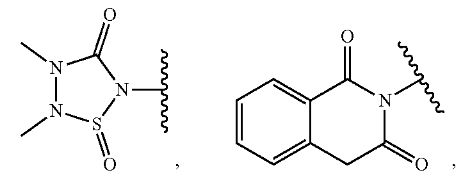

-continued
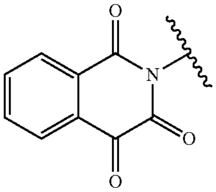,
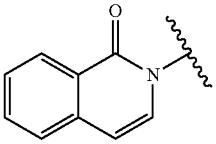,
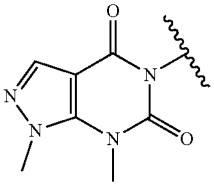,
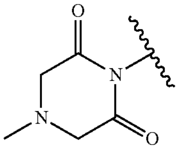,
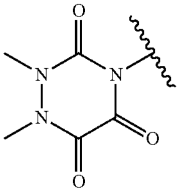,
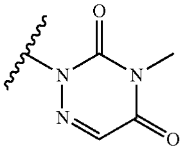,
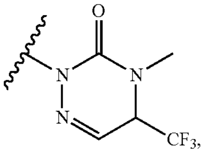,
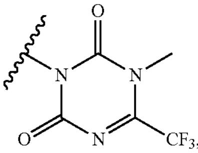,
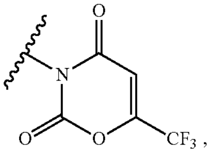,
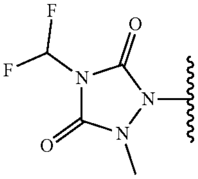,
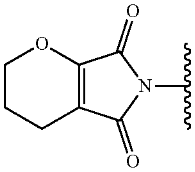,
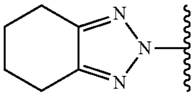,
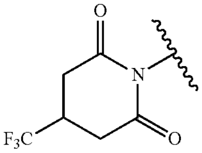,
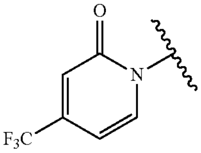,
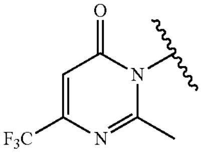,
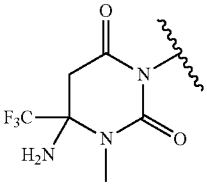,
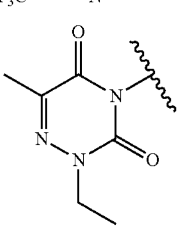,
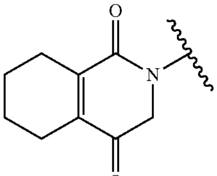,
-continued
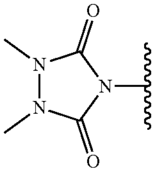,
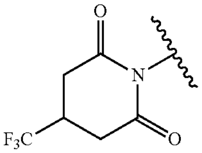,
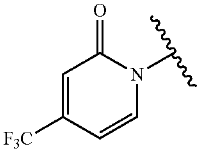,
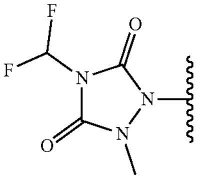,
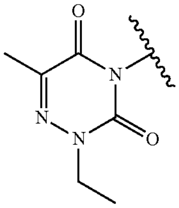,
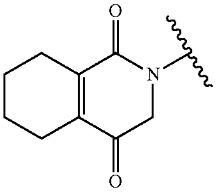,
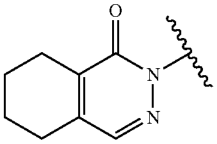,
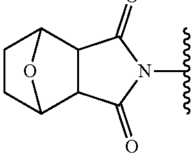,
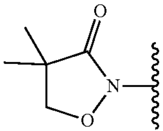,
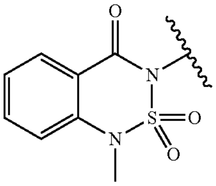,
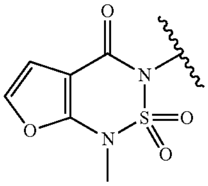,
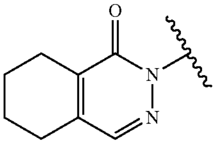,
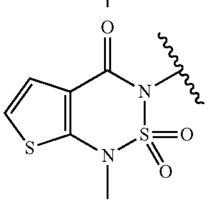,
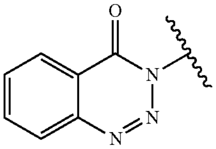,
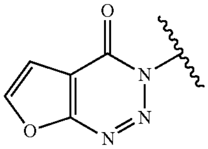,
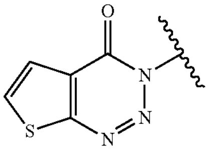,
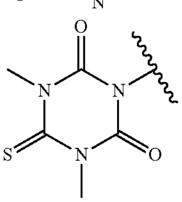, -continued

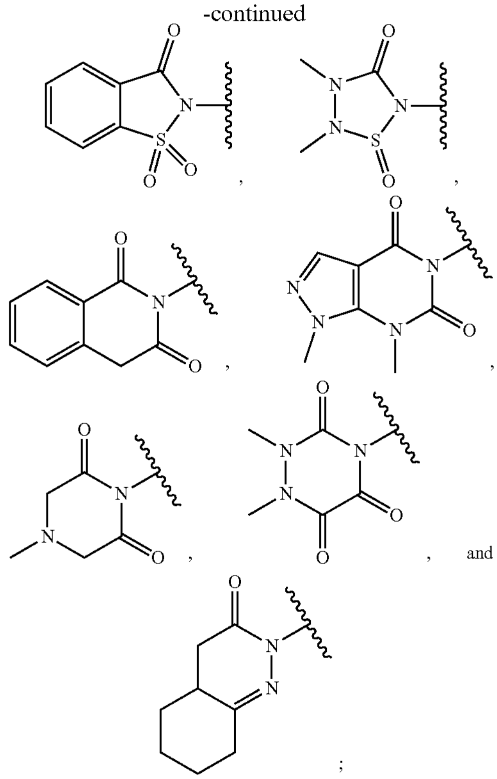

each of $X_1$ and $X_2$ is independently selected from the group consisting of F, Cl, H, Br, —CN, methyl, carboxyl, aldehyde group, hydroxyl, ester group, and amido;

wherein in formula 1 and formula 2, R1 and R3 are selected from the group consisting of H and —$CH_3$; and wherein in formula 1 and formula 2, R is selected from the group consisting of:

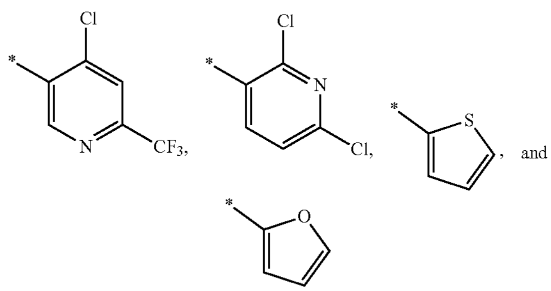

2. The N-phenylimine derivative of claim 1, Het is selected from the group consisting of:

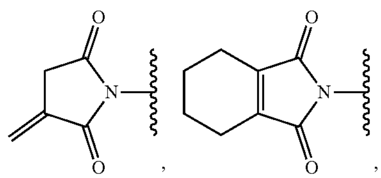

-continued

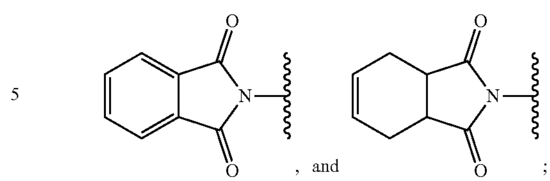

each of $X_1$ and $X_2$ is independently selected from the group consisting of F and Cl;

in formula 1, $R^1$ is H.

3. The N-phenylimine derivative of claim 1, wherein the N-phenylimine derivative is any one selected from the group consisting of compounds represented by formula 1-10, formula 1-16, formula 1-19, and formula 1-22, formula 1-10

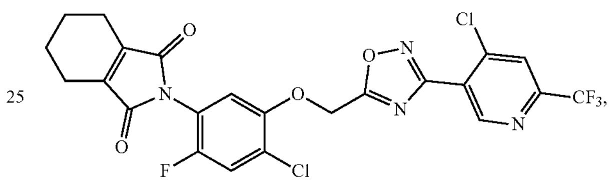

formula 1-16

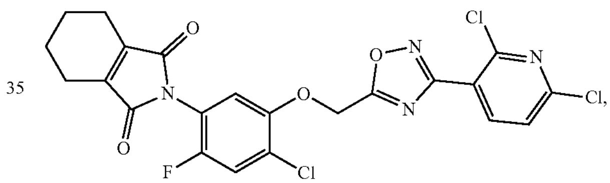

formula 1-19

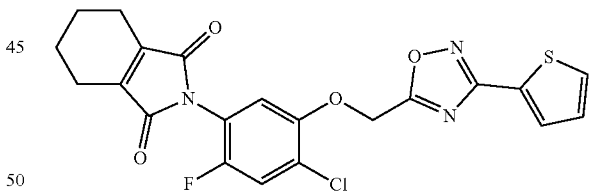

formula 1-22

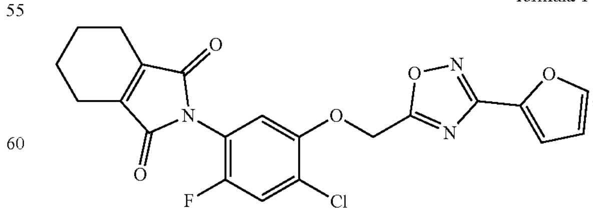

* * * * *